United States Patent
Zhang et al.

(10) Patent No.: US 12,331,110 B2
(45) Date of Patent: Jun. 17, 2025

(54) MONOCLONAL ANTIBODIES AGAINST ENDOTROPHIN AND THE USE THEREOF

(71) Applicant: THE BOARD OF REGENTS OF THE UNIVERSITY OF TEXAS SYSTEM, Austin, TX (US)

(72) Inventors: Ningyan Zhang, Houston, TX (US); Dawei Bu, Dallas, TX (US); Zhiqiang An, Houston, TX (US); Hui Deng, Houston, TX (US); Philipp E. Scherer, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 1096 days.

(21) Appl. No.: 17/273,538

(22) PCT Filed: Sep. 5, 2019

(86) PCT No.: PCT/US2019/049653
§ 371 (c)(1),
(2) Date: Mar. 4, 2021

(87) PCT Pub. No.: WO2020/051275
PCT Pub. Date: Mar. 12, 2020

(65) Prior Publication Data
US 2022/0056124 A1 Feb. 24, 2022

Related U.S. Application Data

(60) Provisional application No. 62/727,140, filed on Sep. 5, 2018.

(51) Int. Cl.
| C07K 16/26 | (2006.01) |
| A61K 39/00 | (2006.01) |
| A61P 35/00 | (2006.01) |
| C07K 16/18 | (2006.01) |

(52) U.S. Cl.
CPC .............. *C07K 16/26* (2013.01); *A61P 35/00* (2018.01); *C07K 16/18* (2013.01); *A61K 2039/505* (2013.01); *C07K 2317/24* (2013.01); *C07K 2317/73* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 7,935,340 | B2 * | 5/2011 | Garcia-Martinez ..... A61P 13/12 |
| | | | 435/69.7 |
| 9,605,057 | B1 | 3/2017 | Scherer et al. |
| 9,868,777 | B2 | 1/2018 | Fu et al. |

| 2015/0259430 | A1 | 9/2015 | Fischer et al. |
| 2016/0130327 | A1 | 5/2016 | Fu et al. |
| 2017/0073416 | A1 | 3/2017 | Couto et al. |

FOREIGN PATENT DOCUMENTS

| CN | 103396491 A | 11/2013 |
| WO | WO 2008/053330 | 5/2008 |
| WO | WO 2017/158097 | 9/2017 |
| WO | WO 2018/098363 | 5/2018 |

OTHER PUBLICATIONS

Bedouelle et al. Fees J. Jan. 2006;273(1):34-46. (Year: 2006).*
Stanford Medicine. Fibroids. May 10, 2015. Retrieved online on Apr. 9, 2024 from URL: <https://stanfordhealthcare.org/content/shc/en/medical-conditions/womens-health/fibroids.html> (Year: 2024).*
Vajdos et al. J Mol Biol. Jul. 5, 2002;320(2):415-28 (Year: 2002).*
Shen. Cell & Bioscience. 2013. 3:6. (Year: 2013).*
Office Communication issued in corresponding Chinese Application No. 201980072262.X, dated Jan. 26, 2024. English Translation.
Bu et al., "Human endotrophin as a driver of malignant tumor growth", *JCI Insight*, 4(9): XP055688306, 2019.
International Preliminary Report on Patentability issued in corresponding PCT Application No. PCT/US2019/049653, mailed on Mar. 18, 2021.
International Search Report and Written Opinion issued in corresponding PCT Application No. PCT/US2019/049653, mailed on Jan. 27, 2020.
Park et al., "Adipocyte-derived Endotrophin promotes malignant tumor progression", *The Journal of clinical Investigation*, 122(11):4243-4256, 2012.
Park et al., "Endotrophin in the tumor stroma: a new therapeutic target for breast cancer?", *Expert Review of Anticancer Therapy*, 13(2):111-113, 2013.
Park et al., "Inhibition of endotrophin, a cleavage product of collagen VI, confers cisplatin sensitivity to tumors", *EMBO Molecular Medicine*, 5(6):935-948, 2013.
Rudikoff et al., "Single amino acid substitution altering antigen-binding specificity", *Proceedings of the National Academy of Sciences*, 79(6):1979-1983, 1982.

(Continued)

*Primary Examiner* — Zachary S Skelding
*Assistant Examiner* — Brianna K Swartwout
(74) *Attorney, Agent, or Firm* — Parker Highlander PLLC

(57) ABSTRACT

Aspects of the present invention relate to methods and reagents for increasing chemosensitivity to platinum-based chemotherapy. In one aspect, a method of increasing chemosensitivity to platinum-based chemotherapy is provided, comprising administering to a patient in need thereof an effective amount of an endotrophin-neutralizing agent. The agent can be a monoclonal antibody, or fragment thereof, capable of binding to the C5 domain of the alphas chain of collagen VI. In some embodiments, the method can further include administering an effective amount of thiazolidinedione to said patient.

14 Claims, 19 Drawing Sheets
(19 of 19 Drawing Sheet(s) Filed in Color)
Specification includes a Sequence Listing.

(56) References Cited

OTHER PUBLICATIONS

Sun et al., "Endotrophin triggers adipose tissue fibrosis and metabolic dysfunction." *Nature Communications*. 2014; 5:3485.
Supplemental Partial Search Report and Invitation to Pay issued in European Application No. 19857330.5, dated May 6, 2022.
Winkler et al., "Changing the antigen binding specificity by single point mutations of an anti-p24 (HIV-1) antibody", *The Journal of Immunology, Williams & Wilkins Co.*, 165(8): 4505-4514, 2000.

* cited by examiner

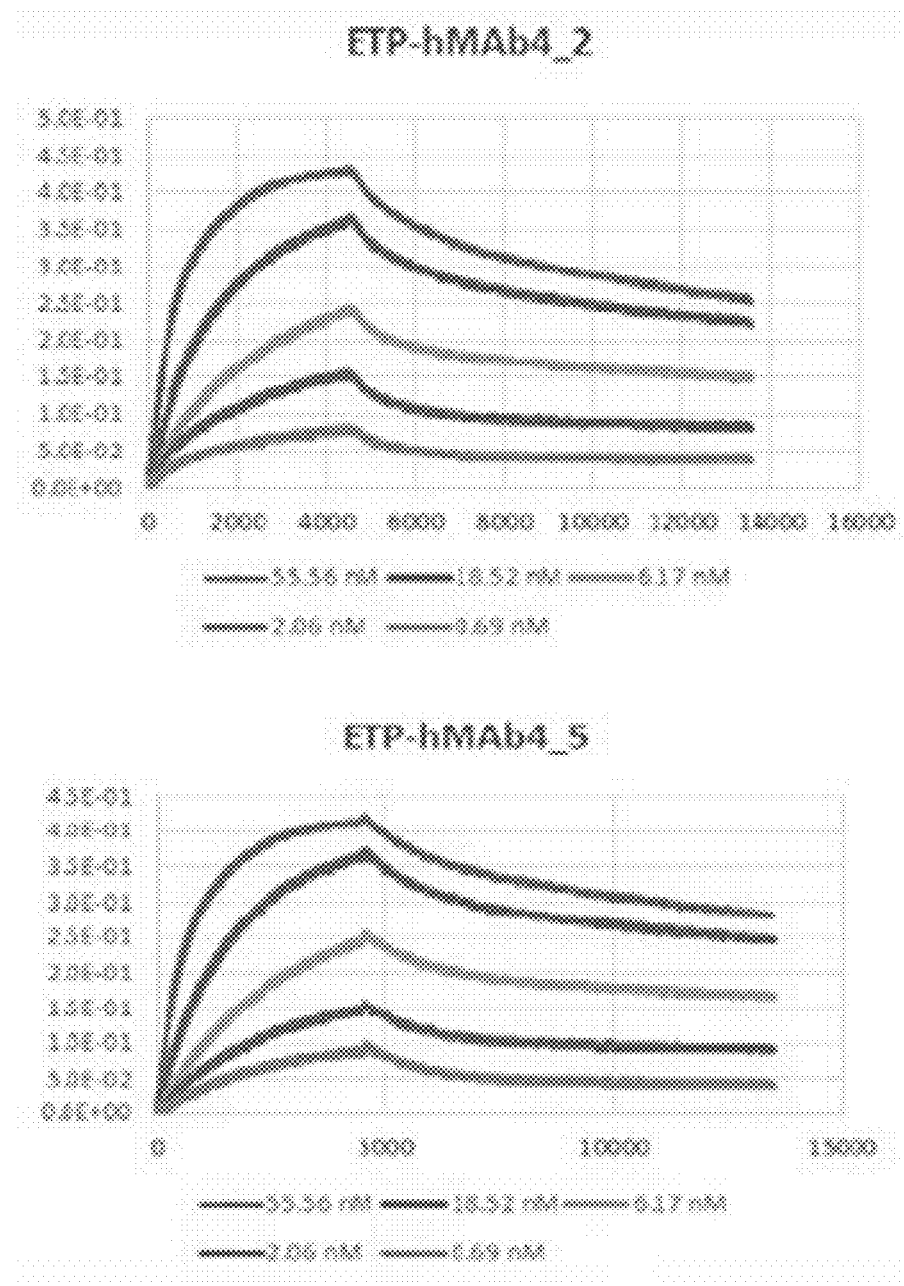
FIG. 12B, cont'd

SEQUENCE LISTING

```
<160> NUMBER OF SEQ ID NOS: 164

<210> SEQ ID NO 1
<211> LENGTH: 6
<212> TYPE: PRT
<213> ORGANISM: Artificial sequence
<220> FEATURE:
<223> OTHER INFORMATION: Synthetic peptide

<400> SEQUENCE: 1

Gln Ser Ile Gly Ser Asn
1               5

<210> SEQ ID NO 2
<211> LENGTH: 3
<212> TYPE: PRT
<213> ORGANISM: Artificial sequence
<220> FEATURE:
<223> OTHER INFORMATION: Synthetic peptide

<400> SEQUENCE: 2

Asp Ala Ser
1

<210> SEQ ID NO 3
<211> LENGTH: 12
<212> TYPE: PRT
<213> ORGANISM: Artificial sequence
<220> FEATURE:
<223> OTHER INFORMATION: Synthetic peptide
```

```
<400> SEQUENCE: 3

Gln Gln Gly Tyr Ser Asp Asn Tyr Leu Asp Asn Ala
1               5                   10

<210> SEQ ID NO 4
<211> LENGTH: 6
<212> TYPE: PRT
<213> ORGANISM: Artificial sequence
<220> FEATURE:
<223> OTHER INFORMATION: Synthetic peptide

<400> SEQUENCE: 4

Gln Ser Ile Asn Ser Tyr
1               5

<210> SEQ ID NO 5
<211> LENGTH: 3
<212> TYPE: PRT
<213> ORGANISM: Artificial sequence
<220> FEATURE:
<223> OTHER INFORMATION: Synthetic peptide

<400> SEQUENCE: 5

Gln Ala Ser
1

<210> SEQ ID NO 6
<211> LENGTH: 14
<212> TYPE: PRT
<213> ORGANISM: Artificial sequence
<220> FEATURE:
<223> OTHER INFORMATION: Synthetic peptide

<400> SEQUENCE: 6

Gln Ser Tyr Asp Tyr Arg Ile Ser Gly Ser Asp Gly Asn Val
1               5                   10

<210> SEQ ID NO 7
<211> LENGTH: 7
<212> TYPE: PRT
<213> ORGANISM: Artificial sequence
<220> FEATURE:
<223> OTHER INFORMATION: Synthetic peptide

<400> SEQUENCE: 7

Gln Ser Ile Ser Ser Ser Tyr
1               5

<210> SEQ ID NO 8
<211> LENGTH: 3
<212> TYPE: PRT
<213> ORGANISM: Artificial sequence
<220> FEATURE:
<223> OTHER INFORMATION: Synthetic peptide

<400> SEQUENCE: 8

Lys Ala Ser
1

<210> SEQ ID NO 9
<211> LENGTH: 12
<212> TYPE: PRT
<213> ORGANISM: Artificial sequence
<220> FEATURE:
<223> OTHER INFORMATION: Synthetic peptide

<400> SEQUENCE: 9
```

```
Gln Tyr Ser Asp Trp Ala Asn Ser Tyr Gly Asn Ala
1               5                   10

<210> SEQ ID NO 10
<211> LENGTH: 6
<212> TYPE: PRT
<213> ORGANISM: Artificial sequence
<220> FEATURE:
<223> OTHER INFORMATION: Synthetic peptide

<400> SEQUENCE: 10

Gln Asn Ile Asn Ser Trp
1               5

<210> SEQ ID NO 11
<211> LENGTH: 3
<212> TYPE: PRT
<213> ORGANISM: Artificial sequence
<220> FEATURE:
<223> OTHER INFORMATION: Synthetic peptide

<400> SEQUENCE: 11

Gln Ala Ser
1

<210> SEQ ID NO 12
<211> LENGTH: 14
<212> TYPE: PRT
<213> ORGANISM: Artificial sequence
<220> FEATURE:
<223> OTHER INFORMATION: Synthetic peptide

<400> SEQUENCE: 12

Gln Ser His Asp Tyr Arg Thr Thr Gly Ser Tyr Gly Asn Val
1               5                   10

<210> SEQ ID NO 13
<211> LENGTH: 6
<212> TYPE: PRT
<213> ORGANISM: Artificial sequence
<220> FEATURE:
<223> OTHER INFORMATION: Synthetic peptide

<400> SEQUENCE: 13

Gln Asn Ile Asn Ser Trp
1               5

<210> SEQ ID NO 14
<211> LENGTH: 3
<212> TYPE: PRT
<213> ORGANISM: Artificial sequence
<220> FEATURE:
<223> OTHER INFORMATION: Synthetic peptide

<400> SEQUENCE: 14

Gln Ala Ser
1

<210> SEQ ID NO 15
<211> LENGTH: 14
<212> TYPE: PRT
<213> ORGANISM: Artificial sequence
<220> FEATURE:
<223> OTHER INFORMATION: Synthetic peptide

<400> SEQUENCE: 15
```

-continued

Gln Ser Tyr Asp Tyr Arg Ser Ser Gly Asn Gly Gly Asn Val
1               5                   10

<210> SEQ ID NO 16
<211> LENGTH: 6
<212> TYPE: PRT
<213> ORGANISM: Artificial sequence
<220> FEATURE:
<223> OTHER INFORMATION: Synthetic peptide

<400> SEQUENCE: 16

His Arg Ile Lys Thr Tyr
1               5

<210> SEQ ID NO 17
<211> LENGTH: 3
<212> TYPE: PRT
<213> ORGANISM: Artificial sequence
<220> FEATURE:
<223> OTHER INFORMATION: Synthetic peptide

<400> SEQUENCE: 17

Gly Ala Ser
1

<210> SEQ ID NO 18
<211> LENGTH: 12
<212> TYPE: PRT
<213> ORGANISM: Artificial sequence
<220> FEATURE:
<223> OTHER INFORMATION: Synthetic peptide

<400> SEQUENCE: 18

Gln Gln Gly Tyr Ser Asp Gly Asn Val Asp Asn Val
1               5                   10

<210> SEQ ID NO 19
<211> LENGTH: 6
<212> TYPE: PRT
<213> ORGANISM: Artificial sequence
<220> FEATURE:
<223> OTHER INFORMATION: Synthetic peptide

<400> SEQUENCE: 19

Gln Asn Ile Tyr Ser Gly
1               5

<210> SEQ ID NO 20
<211> LENGTH: 3
<212> TYPE: PRT
<213> ORGANISM: Artificial sequence
<220> FEATURE:
<223> OTHER INFORMATION: Synthetic peptide

<400> SEQUENCE: 20

Gly Ala Ser
1

<210> SEQ ID NO 21
<211> LENGTH: 13
<212> TYPE: PRT
<213> ORGANISM: Artificial sequence
<220> FEATURE:
<223> OTHER INFORMATION: Synthetic peptide

<400> SEQUENCE: 21

Gln Thr Gly Tyr Trp Thr Gly Ser Ser Asp Tyr Ile Gly

```
<210> SEQ ID NO 22
<211> LENGTH: 8
<212> TYPE: PRT
<213> ORGANISM: Artificial sequence
<220> FEATURE:
<223> OTHER INFORMATION: Synthetic peptide

<400> SEQUENCE: 22

Lys Asn Ala Tyr Leu Ser Tyr Tyr
1               5

<210> SEQ ID NO 23
<211> LENGTH: 3
<212> TYPE: PRT
<213> ORGANISM: Artificial sequence
<220> FEATURE:
<223> OTHER INFORMATION: Synthetic peptide

<400> SEQUENCE: 23

Trp Ala Ser
1

<210> SEQ ID NO 24
<211> LENGTH: 11
<212> TYPE: PRT
<213> ORGANISM: Artificial sequence
<220> FEATURE:
<223> OTHER INFORMATION: Synthetic peptide

<400> SEQUENCE: 24

Ala Ala Glu Tyr Ser Asn Asp Ser Asp Asn Gly
1               5                   10

<210> SEQ ID NO 25
<211> LENGTH: 8
<212> TYPE: PRT
<213> ORGANISM: Artificial sequence
<220> FEATURE:
<223> OTHER INFORMATION: Synthetic peptide

<400> SEQUENCE: 25

Lys Ser Val Tyr Asn Asn Asn Ala
1               5

<210> SEQ ID NO 26
<211> LENGTH: 3
<212> TYPE: PRT
<213> ORGANISM: Artificial sequence
<220> FEATURE:
<223> OTHER INFORMATION: Synthetic peptide

<400> SEQUENCE: 26

Ser Ala Ser
1

<210> SEQ ID NO 27
<211> LENGTH: 11
<212> TYPE: PRT
<213> ORGANISM: Artificial sequence
<220> FEATURE:
<223> OTHER INFORMATION: Synthetic peptide

<400> SEQUENCE: 27

Ala Cys Gly Tyr Ser Ile Ile Ser Asp Asn Gly
1               5                   10
```

<210> SEQ ID NO 28
<211> LENGTH: 7
<212> TYPE: PRT
<213> ORGANISM: Artificial sequence
<220> FEATURE:
<223> OTHER INFORMATION: Synthetic peptide

<400> SEQUENCE: 28

Gln Ser Ile Ser Ser Ser Tyr
1               5

<210> SEQ ID NO 29
<211> LENGTH: 3
<212> TYPE: PRT
<213> ORGANISM: Artificial sequence
<220> FEATURE:
<223> OTHER INFORMATION: Synthetic peptide

<400> SEQUENCE: 29

Tyr Ala Ser
1

<210> SEQ ID NO 30
<211> LENGTH: 10
<212> TYPE: PRT
<213> ORGANISM: Artificial sequence
<220> FEATURE:
<223> OTHER INFORMATION: Synthetic peptide

<400> SEQUENCE: 30

Gln Gly Gly Tyr Ser Gly Tyr Ile Asn Ser
1               5                   10

<210> SEQ ID NO 31
<211> LENGTH: 8
<212> TYPE: PRT
<213> ORGANISM: Artificial sequence
<220> FEATURE:
<223> OTHER INFORMATION: Synthetic peptide

<400> SEQUENCE: 31

Lys Ser Val Tyr Asn Asn Asn Ala
1               5

<210> SEQ ID NO 32
<211> LENGTH: 3
<212> TYPE: PRT
<213> ORGANISM: Artificial sequence
<220> FEATURE:
<223> OTHER INFORMATION: Synthetic peptide

<400> SEQUENCE: 32

Ser Ala Ser
1

<210> SEQ ID NO 33
<211> LENGTH: 11
<212> TYPE: PRT
<213> ORGANISM: Artificial sequence
<220> FEATURE:
<223> OTHER INFORMATION: Synthetic peptide

<400> SEQUENCE: 33

Ala Gly Gly Tyr Ser Ile Ile Ser Asp Asn Gly
1               5                   10

```
<210> SEQ ID NO 34
<211> LENGTH: 8
<212> TYPE: PRT
<213> ORGANISM: Artificial sequence
<220> FEATURE:
<223> OTHER INFORMATION: Synthetic peptide

<400> SEQUENCE: 34

Gln Ser Val Tyr Ser Asn Asn Arg
1               5

<210> SEQ ID NO 35
<211> LENGTH: 3
<212> TYPE: PRT
<213> ORGANISM: Artificial sequence
<220> FEATURE:
<223> OTHER INFORMATION: Synthetic peptide

<400> SEQUENCE: 35

Tyr Ala Ala
1

<210> SEQ ID NO 36
<211> LENGTH: 12
<212> TYPE: PRT
<213> ORGANISM: Artificial sequence
<220> FEATURE:
<223> OTHER INFORMATION: Synthetic peptide

<400> SEQUENCE: 36

Ala Gly Tyr Lys Thr Ala Asp Ser Asp Gly Ile Ala
1               5                   10

<210> SEQ ID NO 37
<211> LENGTH: 8
<212> TYPE: PRT
<213> ORGANISM: Artificial sequence
<220> FEATURE:
<223> OTHER INFORMATION: Synthetic peptide

<400> SEQUENCE: 37

Lys Ser Val Tyr Asn Asn Asn Ala
1               5

<210> SEQ ID NO 38
<211> LENGTH: 3
<212> TYPE: PRT
<213> ORGANISM: Artificial sequence
<220> FEATURE:
<223> OTHER INFORMATION: Synthetic peptide

<400> SEQUENCE: 38

Ser Ala Ser
1

<210> SEQ ID NO 39
<211> LENGTH: 11
<212> TYPE: PRT
<213> ORGANISM: Artificial sequence
<220> FEATURE:
<223> OTHER INFORMATION: Synthetic peptide

<400> SEQUENCE: 39

Ala Gly Gly Tyr Ser Ile Ile Ser Asp Asn Gly
1               5                   10
```

```
<210> SEQ ID NO 40
<211> LENGTH: 6
<212> TYPE: PRT
<213> ORGANISM: Artificial sequence
<220> FEATURE:
<223> OTHER INFORMATION: Synthetic peptide

<400> SEQUENCE: 40

Gln Ser Ile Asn Ser Trp
1               5

<210> SEQ ID NO 41
<211> LENGTH: 3
<212> TYPE: PRT
<213> ORGANISM: Artificial sequence
<220> FEATURE:
<223> OTHER INFORMATION: Synthetic peptide

<400> SEQUENCE: 41

Glu Ala Ser
1

<210> SEQ ID NO 42
<211> LENGTH: 13
<212> TYPE: PRT
<213> ORGANISM: Artificial sequence
<220> FEATURE:
<223> OTHER INFORMATION: Synthetic peptide

<400> SEQUENCE: 42

Gln Gln Gly Tyr Ser Tyr Ser Asn Val Asp Asn Asn Ile
1               5                   10

<210> SEQ ID NO 43
<211> LENGTH: 6
<212> TYPE: PRT
<213> ORGANISM: Artificial sequence
<220> FEATURE:
<223> OTHER INFORMATION: Synthetic peptide

<400> SEQUENCE: 43

Glu Ser Ile Ser Ile Tyr
1               5

<210> SEQ ID NO 44
<211> LENGTH: 3
<212> TYPE: PRT
<213> ORGANISM: Artificial sequence
<220> FEATURE:
<223> OTHER INFORMATION: Synthetic peptide

<400> SEQUENCE: 44

Gln Ala Ser
1

<210> SEQ ID NO 45
<211> LENGTH: 14
<212> TYPE: PRT
<213> ORGANISM: Artificial sequence
<220> FEATURE:
<223> OTHER INFORMATION: Synthetic peptide

<400> SEQUENCE: 45

Gln Ser His Asp Tyr Arg Ile Gly Arg Ser Asp Cys Asn Val
1               5                   10

<210> SEQ ID NO 46
```

```
<211> LENGTH: 9
<212> TYPE: PRT
<213> ORGANISM: Artificial sequence
<220> FEATURE:
<223> OTHER INFORMATION: Synthetic peptide

<400> SEQUENCE: 46

Gly Ile Asp Phe Ser Ala Gly Tyr Tyr
1               5

<210> SEQ ID NO 47
<211> LENGTH: 9
<212> TYPE: PRT
<213> ORGANISM: Artificial sequence
<220> FEATURE:
<223> OTHER INFORMATION: Synthetic peptide

<400> SEQUENCE: 47

Ile Tyr Ala Gly Arg Ser Leu Asn Thr
1               5

<210> SEQ ID NO 48
<211> LENGTH: 13
<212> TYPE: PRT
<213> ORGANISM: Artificial sequence
<220> FEATURE:
<223> OTHER INFORMATION: Synthetic peptide

<400> SEQUENCE: 48

Ala Arg Asp Gly Ala Ser Ser Gly Tyr Tyr Phe Lys Leu
1               5                   10

<210> SEQ ID NO 49
<211> LENGTH: 9
<212> TYPE: PRT
<213> ORGANISM: Artificial sequence
<220> FEATURE:
<223> OTHER INFORMATION: Synthetic peptide

<400> SEQUENCE: 49

Gly Phe Ser Phe Ser Arg Ser Asp Tyr
1               5

<210> SEQ ID NO 50
<211> LENGTH: 7
<212> TYPE: PRT
<213> ORGANISM: Artificial sequence
<220> FEATURE:
<223> OTHER INFORMATION: Synthetic peptide

<400> SEQUENCE: 50

Ile Asp Pro Gly Tyr Ser Asp
1               5

<210> SEQ ID NO 51
<211> LENGTH: 10
<212> TYPE: PRT
<213> ORGANISM: Artificial sequence
<220> FEATURE:
<223> OTHER INFORMATION: Synthetic peptide

<400> SEQUENCE: 51

Ala Arg Asp Leu Gly Phe Asp Ser Asn Leu
1               5                   10

<210> SEQ ID NO 52
<211> LENGTH: 9
```

<212> TYPE: PRT
<213> ORGANISM: Artificial sequence
<220> FEATURE:
<223> OTHER INFORMATION: Synthetic peptide

<400> SEQUENCE: 52

Gly Phe Ser Phe Ser Ser Gly Tyr Tyr
1               5

<210> SEQ ID NO 53
<211> LENGTH: 8
<212> TYPE: PRT
<213> ORGANISM: Artificial sequence
<220> FEATURE:
<223> OTHER INFORMATION: Synthetic peptide

<400> SEQUENCE: 53

Ile Tyr Gly Gly Asn Asn Asn Pro
1               5

<210> SEQ ID NO 54
<211> LENGTH: 12
<212> TYPE: PRT
<213> ORGANISM: Artificial sequence
<220> FEATURE:
<223> OTHER INFORMATION: Synthetic peptide

<400> SEQUENCE: 54

Arg Lys Asp Ile Asn Ile Gly Gly Ala Tyr Glu Leu
1               5                   10

<210> SEQ ID NO 55
<211> LENGTH: 9
<212> TYPE: PRT
<213> ORGANISM: Artificial sequence
<220> FEATURE:
<223> OTHER INFORMATION: Synthetic peptide

<400> SEQUENCE: 55

Gly Phe Ser Phe Ser Asn Ser Asp Tyr
1               5

<210> SEQ ID NO 56
<211> LENGTH: 9
<212> TYPE: PRT
<213> ORGANISM: Artificial sequence
<220> FEATURE:
<223> OTHER INFORMATION: Synthetic peptide

<400> SEQUENCE: 56

Ile Asp Leu Val Gly Asn Thr Asn Ser
1               5

<210> SEQ ID NO 57
<211> LENGTH: 10
<212> TYPE: PRT
<213> ORGANISM: Artificial sequence
<220> FEATURE:
<223> OTHER INFORMATION: Synthetic peptide

<400> SEQUENCE: 57

Ala Arg Asp Leu Gly Phe Asp Thr Asn Leu
1               5                   10

<210> SEQ ID NO 58
<211> LENGTH: 9
<212> TYPE: PRT

```
<213> ORGANISM: Artificial sequence
<220> FEATURE:
<223> OTHER INFORMATION: Synthetic peptide

<400> SEQUENCE: 58

Gly Phe Ser Phe Ser Arg Gly Asp Tyr
1               5

<210> SEQ ID NO 59
<211> LENGTH: 9
<212> TYPE: PRT
<213> ORGANISM: Artificial sequence
<220> FEATURE:
<223> OTHER INFORMATION: Synthetic peptide

<400> SEQUENCE: 59

Ile Asp Val Gly Arg Asp Asn Asp Ser
1               5

<210> SEQ ID NO 60
<211> LENGTH: 10
<212> TYPE: PRT
<213> ORGANISM: Artificial sequence
<220> FEATURE:
<223> OTHER INFORMATION: Synthetic peptide

<400> SEQUENCE: 60

Ala Arg Asp Leu Gly Phe Asp Thr Asn Leu
1               5                   10

<210> SEQ ID NO 61
<211> LENGTH: 9
<212> TYPE: PRT
<213> ORGANISM: Artificial sequence
<220> FEATURE:
<223> OTHER INFORMATION: Synthetic peptide

<400> SEQUENCE: 61

Gly Phe Ser Phe Ser Ser Ser Tyr Tyr
1               5

<210> SEQ ID NO 62
<211> LENGTH: 9
<212> TYPE: PRT
<213> ORGANISM: Artificial sequence
<220> FEATURE:
<223> OTHER INFORMATION: Synthetic peptide

<400> SEQUENCE: 62

Ile Tyr Leu Gly Asn Asn Glu Asn Thr
1               5

<210> SEQ ID NO 63
<211> LENGTH: 14
<212> TYPE: PRT
<213> ORGANISM: Artificial sequence
<220> FEATURE:
<223> OTHER INFORMATION: Synthetic peptide

<400> SEQUENCE: 63

Ala Arg Asp Thr Ser Gly Gly Ser Asp Tyr Tyr Phe Gly Leu
1               5                   10

<210> SEQ ID NO 64
<211> LENGTH: 9
<212> TYPE: PRT
<213> ORGANISM: Artificial sequence
```

<220> FEATURE:
<223> OTHER INFORMATION: Synthetic peptide

<400> SEQUENCE: 64

Gly Phe Ser Phe Ser Ser Arg Asp Tyr
1               5

<210> SEQ ID NO 65
<211> LENGTH: 7
<212> TYPE: PRT
<213> ORGANISM: Artificial sequence
<220> FEATURE:
<223> OTHER INFORMATION: Synthetic peptide

<400> SEQUENCE: 65

Ile Asp Val Gly Tyr Thr Asp
1               5

<210> SEQ ID NO 66
<211> LENGTH: 10
<212> TYPE: PRT
<213> ORGANISM: Artificial sequence
<220> FEATURE:
<223> OTHER INFORMATION: Synthetic peptide

<400> SEQUENCE: 66

Ala Arg Asp Leu Gly Phe Asp Ser Asn Leu
1               5                   10

<210> SEQ ID NO 67
<211> LENGTH: 9
<212> TYPE: PRT
<213> ORGANISM: Artificial sequence
<220> FEATURE:
<223> OTHER INFORMATION: Synthetic peptide

<400> SEQUENCE: 67

Gly Phe Ser Phe Ser Arg Ser Asp Tyr
1               5

<210> SEQ ID NO 68
<211> LENGTH: 7
<212> TYPE: PRT
<213> ORGANISM: Artificial sequence
<220> FEATURE:
<223> OTHER INFORMATION: Synthetic peptide

<400> SEQUENCE: 68

Ile Asp Pro Gly Tyr Ser Asp
1               5

<210> SEQ ID NO 69
<211> LENGTH: 10
<212> TYPE: PRT
<213> ORGANISM: Artificial sequence
<220> FEATURE:
<223> OTHER INFORMATION: Synthetic peptide

<400> SEQUENCE: 69

Ala Arg Asp Leu Gly Phe Asp Ser Asn Leu
1               5                   10

<210> SEQ ID NO 70
<211> LENGTH: 9
<212> TYPE: PRT
<213> ORGANISM: Artificial sequence
<220> FEATURE:

```
<223> OTHER INFORMATION: Synthetic peptide

<400> SEQUENCE: 70

Gly Phe Ser Phe Ser Arg Gly Asp Tyr
1               5

<210> SEQ ID NO 71
<211> LENGTH: 9
<212> TYPE: PRT
<213> ORGANISM: Artificial sequence
<220> FEATURE:
<223> OTHER INFORMATION: Synthetic peptide

<400> SEQUENCE: 71

Ile Asp Ala Gly Ser Gly Ser Lys Gly
1               5

<210> SEQ ID NO 72
<211> LENGTH: 10
<212> TYPE: PRT
<213> ORGANISM: Artificial sequence
<220> FEATURE:
<223> OTHER INFORMATION: Synthetic peptide

<400> SEQUENCE: 72

Ala Arg Asp Leu Gly Phe Asp Thr Asn Leu
1               5                   10

<210> SEQ ID NO 73
<211> LENGTH: 9
<212> TYPE: PRT
<213> ORGANISM: Artificial sequence
<220> FEATURE:
<223> OTHER INFORMATION: Synthetic peptide

<400> SEQUENCE: 73

Gly Phe Ser Phe Ser Arg Ser Asp Tyr
1               5

<210> SEQ ID NO 74
<211> LENGTH: 7
<212> TYPE: PRT
<213> ORGANISM: Artificial sequence
<220> FEATURE:
<223> OTHER INFORMATION: Synthetic peptide

<400> SEQUENCE: 74

Ile Asp Pro Gly Tyr Ser Asp
1               5

<210> SEQ ID NO 75
<211> LENGTH: 10
<212> TYPE: PRT
<213> ORGANISM: Artificial sequence
<220> FEATURE:
<223> OTHER INFORMATION: Synthetic peptide

<400> SEQUENCE: 75

Ala Arg Asp Leu Gly Phe Asp Ser Asn Leu
1               5                   10

<210> SEQ ID NO 76
<211> LENGTH: 9
<212> TYPE: PRT
<213> ORGANISM: Artificial sequence
<220> FEATURE:
<223> OTHER INFORMATION: Synthetic peptide
```

<400> SEQUENCE: 76

Gly Phe Ser Phe Ser Asp Asn Tyr Trp
1               5

<210> SEQ ID NO 77
<211> LENGTH: 7
<212> TYPE: PRT
<213> ORGANISM: Artificial sequence
<220> FEATURE:
<223> OTHER INFORMATION: Synthetic peptide

<400> SEQUENCE: 77

Ile Tyr Thr Gly Ser Gly Ser
1               5

<210> SEQ ID NO 78
<211> LENGTH: 13
<212> TYPE: PRT
<213> ORGANISM: Artificial sequence
<220> FEATURE:
<223> OTHER INFORMATION: Synthetic peptide

<400> SEQUENCE: 78

Val Arg Asp Leu Tyr Gly Asp Ile Glu His Val Pro Phe
1               5                   10

<210> SEQ ID NO 79
<211> LENGTH: 9
<212> TYPE: PRT
<213> ORGANISM: Artificial sequence
<220> FEATURE:
<223> OTHER INFORMATION: Synthetic peptide

<400> SEQUENCE: 79

Gly Ile Asp Phe Ser Ala Gly Tyr Tyr
1               5

<210> SEQ ID NO 80
<211> LENGTH: 9
<212> TYPE: PRT
<213> ORGANISM: Artificial sequence
<220> FEATURE:
<223> OTHER INFORMATION: Synthetic peptide

<400> SEQUENCE: 80

Ile Tyr Ala Gly Arg Ser Leu Asn Thr
1               5

<210> SEQ ID NO 81
<211> LENGTH: 13
<212> TYPE: PRT
<213> ORGANISM: Artificial sequence
<220> FEATURE:
<223> OTHER INFORMATION: Synthetic peptide

<400> SEQUENCE: 81

Ala Arg Asp Gly Ala Ser Ser Gly Tyr Tyr Phe Lys Leu
1               5                   10

<210> SEQ ID NO 82
<211> LENGTH: 9
<212> TYPE: PRT
<213> ORGANISM: Artificial sequence
<220> FEATURE:
<223> OTHER INFORMATION: Synthetic peptide

```
<400> SEQUENCE: 82

Gly Ile Asp Phe Ser Ala Gly Tyr Tyr
1               5

<210> SEQ ID NO 83
<211> LENGTH: 9
<212> TYPE: PRT
<213> ORGANISM: Artificial sequence
<220> FEATURE:
<223> OTHER INFORMATION: Synthetic peptide

<400> SEQUENCE: 83

Ile Tyr Ala Gly Arg Ser Leu Asn Thr
1               5

<210> SEQ ID NO 84
<211> LENGTH: 12
<212> TYPE: PRT
<213> ORGANISM: Artificial sequence
<220> FEATURE:
<223> OTHER INFORMATION: Synthetic peptide

<400> SEQUENCE: 84

Ala Arg Asp Gly Ala Ser Ser Gly Tyr Tyr Phe Lys
1               5                   10

<210> SEQ ID NO 85
<211> LENGTH: 9
<212> TYPE: PRT
<213> ORGANISM: Artificial sequence
<220> FEATURE:
<223> OTHER INFORMATION: Synthetic peptide

<400> SEQUENCE: 85

Gly Phe Ser Phe Ser Arg Ser Asp Tyr
1               5

<210> SEQ ID NO 86
<211> LENGTH: 7
<212> TYPE: PRT
<213> ORGANISM: Artificial sequence
<220> FEATURE:
<223> OTHER INFORMATION: Synthetic peptide

<400> SEQUENCE: 86

Ile Asp Pro Gly Tyr Ser Asp
1               5

<210> SEQ ID NO 87
<211> LENGTH: 10
<212> TYPE: PRT
<213> ORGANISM: Artificial sequence
<220> FEATURE:
<223> OTHER INFORMATION: Synthetic peptide

<400> SEQUENCE: 87

Ala Arg Asp Leu Gly Phe Asp Ser Asn Leu
1               5                   10

<210> SEQ ID NO 88
<211> LENGTH: 9
<212> TYPE: PRT
<213> ORGANISM: Artificial sequence
<220> FEATURE:
<223> OTHER INFORMATION: Synthetic peptide

<400> SEQUENCE: 88
```

Gly Phe Ser Phe Ser Arg Gly Asp Tyr
1               5

<210> SEQ ID NO 89
<211> LENGTH: 9
<212> TYPE: PRT
<213> ORGANISM: Artificial sequence
<220> FEATURE:
<223> OTHER INFORMATION: Synthetic peptide

<400> SEQUENCE: 89

Ile Asp Val Gly Ser Val Ile Glu Ser
1               5

<210> SEQ ID NO 90
<211> LENGTH: 9
<212> TYPE: PRT
<213> ORGANISM: Artificial sequence
<220> FEATURE:
<223> OTHER INFORMATION: Synthetic peptide

<400> SEQUENCE: 90

Ala Arg Asp Leu Gly Phe Asp Thr Asn
1               5

<210> SEQ ID NO 91
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 91
cagtcggtga aggagtccgg gggagacctg gtcaagcctg gggcttccct gacactcacc       60
tgcacagcct ctggaatcga cttcagtgcc ggctactaca tgtgctgggt ccgccaggct      120
ccagggaagg gctggagtt gatcgcatgc atttatgctg gtcgtagtct taacactttc       180
tacgcgagct gggcgaaagg ccgattcacc atctccagag cctcgtcgac cacggtgact      240
ctggcgatga ccagtctgac agccgcggac acggccacct atttctgtgc gagagatggg      300
gctagcagtg gctactactt taagttgtgg ggcccaggca ccctggtcac catctcttca      360

<210> SEQ ID NO 92
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 92
gagctcgata tgacccagac tccagcctct gtggaggtag ctgtgggagg cacagtcacc       60
atcaagtgcc aggccagtca gagcattggt agtaatttag cctggtatca gcagaaacca      120
gggcagcgtc ccaatgtcct gatctacgat gcatcgaatc tggcatctgg ggtctcatcg      180
cggttcaaag gcagtggatc tgggacacag ttcactctca ccatcagcgg cggggagtgt      240
gccgatgctg ccacttacta ctgtcaacag ggttatagtg ataattatct tgataatgct      300
ttcggcggag ggaccgaggt ggtggtcaaa                                        330

<210> SEQ ID NO 93
<211> LENGTH: 351
<212> TYPE: DNA
<213> ORGANISM: Artificial sequence

```
<220> FEATURE:
<223> OTHER INFORMATION: Synthetic oligonucleotide

<400> SEQUENCE: 93
gagcagtcgt tggaggagtc cgagggaggc ctggtccagc ctgagggatc cctgacactc      60
acctgcacag cttctggatt ctccttcagt agaagcgact acatgtgttg ggtccgccag     120
gctccaggga agggactgga gtggatcgga tggattgatc ctggttatag tgacacttac     180
tacgcgagct gggcgcaagg ccgaaccacc atctccaaag cctcgtcgac cacggtgact     240
ctgcagatga ccagtctgac agtcgcggac acggccacct atttctgtgc gagagatttg     300
gggtttgata gtaatttgtg gggcccaggc accctggtca ccatctcctc a             351

<210> SEQ ID NO 94
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 94
gagctcgatc tgacccagac tccagcctcc gtgtctgaac tgtgggagg cacagtcacc       60 atcaagtgcc aggccagtca gagtattaat agttacttat cctggtatca gcagaaacca    120
gggcagcctc ccaagctcct gatttaccag gcatcgaaac tggcatctgg ggtcccatcg    180
cggttcaaag gcagtggatc tgggacacag ttcactctca ccatcagcga cctggagtgt    240
gccgatgctg ccacttacta ctgtcaaagc tatgattatc gtattagtgg tagcgatggt    300
aatgttttcg gcggagggac caatgtggaa atcaaa                              336

<210> SEQ ID NO 95
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 95
agcagtcggg tgaaggagtc cgggggagac ctggtcaagc ctggggcatc cctgacactc      60
acctgcaaag cctctggatt ctccttcagt agcggctact acatatgttg ggtccgccag    120
gctccaggga aggggctgga gtggatcgcg tgcatttatg gtggtaataa taacccatat    180
tacgcgaact gggtgaatgg tcgattcacc acctccaaaa cctcgtcgac cacggtgact    240
ctgcaaatga ccaatctgac aggcgcggac acggccacct atttctgtgc gagaaaagat    300
attaatattg gtggtgctta tgagttgtgg ggcccaggca ccctggtcac catctcctca    360

<210> SEQ ID NO 96
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 96
gagctcgtga tgacccagac tccagcctcc gtgtctgaac tgtgggagg cacagtcacc       60 atcaactgcc aggccagtca gagtattagt agtagctact atcctggta tcagcagaaa     120 ccagggcagc ctcccaagct cctgatttac aaggcatcca ctctggcatc tggggtccca    180
tcgcggttca aaggcagtgg atctgggaca cagttcagtc tcaccatcag cgacctggag    240
```
tgtgccgatg ctgccactta ctattgtcaa tatagtgatt gggctaatag ttatgggaat    300
gctttcggcg gggggaccga ggtggtggtc aaa                                 333

<210> SEQ ID NO 97
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 97
cagtcggtga aggagtccga gggaggcctg gtccagcctg agggatccct gacactcacc    60
tgcacagctt ctggattctc cttcagtaac agcgactaca tgtgctgggt ccgccaggct    120
ccagggaagg gactggagtg gatcggatgg atagatcttg ttggtaatac taattcttac    180
tacgcgagtt gggcgaaagg ccgattcacc atctccaaaa cctcgtcgac cacggtggct    240
ctgcaaatga ccagtctgac agtcgcggac acggccacct atttctgtgc gagagatttg    300
ggttttgata ctaatttgtg gggcccaggc accctggtca ccgtctcctc a             351

<210> SEQ ID NO 98
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 98
gagctcgatc tgacccagac tccagcctcg gtgtctgcag ctgtgggagg cacagtcacc    60
atcaattgcc aggccagtca gaacattaat agttggttat cctggtatca gcagaaacca    120
gggcagcgtc ccaagctcct gatttaccag gcatcgaaac tgccatctgg ggtcccatcg    180
cggttcaagg gcagtggatc tgggacacag ttcactctca ccatcagcga cctggagtgt    240
gccgatgctg ccacttacta ctgtcaaagc catgattatc gtactactgg tagttatggt    300
aatgttttcg gcggagggac tgaggtggaa atcaaa                              336

<210> SEQ ID NO 99
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 99
cagtcgttgg aggagtccgg gggaggcctg gtccagcctg agggatccct gacactcacc    60
tgcacagctt ctggattctc cttcagtagg ggcgactaca tgtgctgggt ccgccaggct    120
ccagggaagg gactggagtg gatcggatgg atagatgttg gtcgtgataa tgattcttac    180
tacgcgactt gggcgaaagg ccgattcagc atctccaaaa cctcgtcgac tacggtgact    240
ctgcaaatga ccagtctgac agtcgcggac acggccacct atttctgtgc gagagatttg    300
ggttttgata ctaatttgtg gggcccaggc accctggtca ccgtctcttc a             351

<210> SEQ ID NO 100
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 100
gagctcgata tgacccagac tccagcctcg gtgtctgcag ctgtgggagg cacagtcacc    60
atcaactgcc aggccagtca gaacattaat agttggttat cctggtatca gcagaaacca   120
gggcagcctc ccaagctcct gatttatcag gcatcgaaac tggcatctgg ggtcccatcg   180
cggttgaaag gcagtggatc tgggacacag ttcagtctca ccatcagcga cctggagtgt   240
gccgatggtg ccacttacta ctgtcaaagc tatgattatc gtagtagtgg taacggtggt   300
aatgttttcg gcggagggac cgaggtggaa atcaaa                             336

<210> SEQ ID NO 101
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 101
cagtcggtga aggagtccga gggaggcctg gtccagcctg aggatcccct gacactcacc    60
tgcacagctt ctggattctc cttcagtagc agctactaca tgtgctgggt ccgccaggct   120
ccagggaagg ggctggagtg gatcggatgc atttatcttg gtaataacga aaatactgcc   180
tacacgagct gggcgaaagg ccgattcacc atctccaaaa cctcgtcgac cacggtgact   240
ctgcaaatga ccagtctgac agccgcggac acgaccacct atttctgtgc gagagatact   300
agtggtggta gtgattatta ttttggcttg tggggccag gcaccctggt caccatctcc    360
tca                                                                  363

<210> SEQ ID NO 102
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 102
gagctcgatc tgacccagac tccagcctct gtggaggtag ctgtgggagg cacagtcacc    60
atcaagtgcc aggccagtca tcgcattaaa acctacttag cctggtatca gcagaaacca   120
gggcagcctc ccaagctcct gatctatggt gcatccactc tggcatctgg ggtcccatcg   180
cggttcaaag gcagtggatc tgggacacag tttactctca ccatcagcgg cgtggagtgt   240
gccgatgctg ccacttatta ttgtcaacag ggttatagtg acgggaacgt tgataatgtt   300
ttcggcggag ggaccgaggt ggaaatcaaa                                    330

<210> SEQ ID NO 103
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 103
gagcagtcgg tggaggagtc cggggggaggc ctggtccagc ctgagggatc cctgacactc    60
acctgcacag cttctggatt ctccttcagt agcagggact acatgtgttg ggtccgccag   120
gctccaggga agggactgga gtggatcgga tggattgatg ttggttatac tgacgcttac   180
tacgcgagct gggcgaaagg ccgattcacc atctccagaa cctcgtcgac cacggtgact   240
ctgcaaatga ccagtctgac agtcgcggac acggccacct atttctgtgc gagagatttg   300

```
ggttttgata gtaatttgtg gggcccaggc accctggtca ccatctcttc a            351
```

<210> SEQ ID NO 104
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 104

```
gagctcgtgc tgacccagac accagcctcc gtgtctgcag ctgtgggagg cacagtcagc     60
atcaattgcc agtccagtca aaacatttat agtggtttgg cctggtatca gcagaaacca    120
gggcagcctc ccaagctcct gatctatggt gcatccactc tggcatctgg ggtctcatcg    180
cggttcaaag gcagtggatc tgggacagag ttcactctca ccatcagcga cctggagtgt    240
gccgatgctg ccacttacta ctgtcaaacc ggttattgga ctggtagtag tgattatatt    300
ggttttggcg agggaccaa tgtggaaatc aaa                                   333
```

<210> SEQ ID NO 105
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 105

```
gagcagtcgg tgaaggggtc cgaggaggc ctggtccagc ctgagggatc cctgacactc      60
acctgcacag cttctggatt ctccttcagt agaagcgact acatgtgttg ggtccgccag    120
gctccaggga agggactgga gtggatcgga tggattgatc ctggttatag tgacacttac    180
tacgcgagct gggcgcaagg ccgaaccacc atctccaaag cctcgtcgac cacggtgact    240
ctgcagatga ccagtctgac agtcgcggac acggccacct atttctgtgc gagagatttg    300
gggtttgata gtaatttgtg gggcccaggc accctggtca ccgtctcttc a             351
```

<210> SEQ ID NO 106
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 106

```
acccagacac cagcctccgt gtctgcagct gtgggaggca cagtcagcat caattgccag     60
tccagtcaga gtgtttataa gaacgcctat ttatcctact acttagcctg gtatcagcag    120
aaaccagggc agcctcccaa gctcctgatc tactgggctt ccactctggc atctggggtc    180
ccatcgcggt tcaaaggcag tggatctggg acacagttca ctctcaccat cagcgacgtg    240
cagtgtgacg atgctgccac ttactactgt gcagccgaat atagtaatga tagtgataat    300
ggttttcggcg agggaccaa tgtggaaatc aaa                                  333
```

<210> SEQ ID NO 107
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 107

```
cagtcgttgg aggagtccgg gggaggcctg gtcaagcctg gaggaacccc gacactcacc      60
```

```
tgcacagcct ctggattctc cttcagccgt ggcgactaca tgtgctgggt ccgccaggct      120
ccagggaagg gactggagtg gatcggatgg attgatgctg gtagtggtag taaaggttac      180
tacgcgaggt gggcgaaagg ccgattcacc atctccaaaa cctcgtccac cacggtgact      240
ttacaaatga ctagtgtgac agtcgcggac acggccactt atttctgtgc gagagatttg      300
ggttttgata ctaatttgtg gggcccaggc accctggtca ccatctcttc a              351
```

<210> SEQ ID NO 108
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 108

```
gagctcgtga tgacccagac tccatctccc gtgtctgcag ctgtgggagg cacagtcagc      60
atcagttgcc aggccagtaa gagtgtttat aataacaatg ccttatcctg gtatcagcag      120
aaaccagggc agcctcccaa actcctgatc tattctgcat ccactctggc atctggggtc      180
ccatcgcggt tcagcggcag tggttctggg acagagttca ctctcaccat cagcggcgtg      240
cagtgtgacg atgctgccac ttactattgt gcatgcggtt atagtattat tagtgataat      300
ggtttcggcg agggaccaa tgtggaaatc aaa                                    333
```

<210> SEQ ID NO 109
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 109

```
gagcagtcgg tggaggagtc cgggggaggc ctggtccagc ctgagggatc cctgacactc      60
acctgcacag cttctggatt ctccttcagt agaagcgact acatgtgttg ggtccgccag      120
gctccaggga agggactgga gtggatcgga tggattgatc ctggttatag tgacacttac      180
tacgcgagct gggcgcaagg ccgaaccacc atctccaaag cctcgtcgac cacggtgact      240
ctgcagatga ccagtctgac agtcgcggac acggccacct atttctgtgc gagagatttg      300 gggttttgata gtaatttgtg gggcccaggc accctggtca ccgtctcttc a              351
```

<210> SEQ ID NO 110
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 110

```
gagctcgata tgacccagac tccagcctcc gtgtctgaac ctgtgggagg cacagtcacc      60
atcaactgcc aggccagtca gagtattagt agtagctact tatcctggta tcagcagaaa      120
ccagggcagc ctcccaagct cctgatctat tatgcatcca ctctggcatc tggggtctca      180
tcgcggttca aaggcagtgg atctgggaca cagttcactc tcaccatcag cgacctggag      240
tgtgacgatg ctgccactta ctactgtcag ggcggttata gtggatatat caattctttc      300
ggcggaggga ccgaggtggt cgtcaaa                                          327
```

<210> SEQ ID NO 111

```
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 111
gagcagtcgg tggaggagtc cggggaggc  ctggtcaagc ctggggcatc cctgacactc    60
acctgcaaag cctctggatt ctccttcagt gacaactact ggatatactg ggtccgccag   120
gctccaggga aggggctgga gtggatcgga tatatttata ctggtagtgg tagcacttac   180
tacgcgagct gggcgaaagg ccgaagcacc atctccaaaa cctcgtcgac cacggtgact   240
ctacaaatga ccagtctgac agccgcggac acggccacct atttctgtgt gagagatctt   300
tatggtgata ttgagcatgt gcccttctgg ggcccaggca ccctggtcac cgtctcttca   360

<210> SEQ ID NO 112
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 112
gagctcgtga tgacccagac tccatctccc gtgtctgcag ctgtgggagg cacagtcagc    60
atcagttgcc aggccagtaa gagtgtttat aataacaatg ccttatcctg gtatcagcag   120
aaaccagggc agcctcccaa actcctgatc tattctgcat ccactctggc atctggggtc   180
ccatcgcggt tcagcggcag tggttctggg acagagttca ctctcaccat cagcggcgtg   240
cagtgtgacg atgctgccac ttactattgt gcaggcggtt atagtattat tagtgataat   300
ggtttcggcg aagggaccga gctggaaatc aaa                                333

<210> SEQ ID NO 113
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 113
cagtcggtgg aggagtccgg gggagacctg gtcaagcctg ggcttccct  gacactcacc    60
tgcacagcct ctggaatcga cttcagtgcc ggctactaca tgtgctgggt ccgccaggct   120
ccagggaagg ggctggagtt gatcgcatgc atttatgctg gtcgtagtct taacactttc   180
tacgcgagct gggcgaaagg ccgattcacc atctccagag cctcgtcgac cacggtgact   240
ctggcgatga ccagtctgac agccgcggac acggccacct atttctgtgc gagagatggg   300
gctagcagtg gctactactt taagttgtgg ggcccaggca ccctggtcac catctcctca   360

<210> SEQ ID NO 114
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 114
gagctcgtga tgacccagac tccatccccc gtgtctgcag ctgtgggagg cacagtcacc    60
atcaactgcc agtccagtca gagtgtttat agtaacaacc gcttagcctg gtatcagcag   120
aaaccagggc agcctcccaa gctcctggtc tattatgcag ccactctggc atctggggtc   180
```

```
ccgtcgcggt tcaaaggcag tggatatggg acacagtcca ctctcaccat cgccgatgtg    240
gtgtgtgacg atgctgccac ttactactgt gcaggatata aaactgctga ttctgatggt    300
attgctttcg gcggagggac cgaggtggtg gtcaaa                              336
```

<210> SEQ ID NO 115
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 115

```
cagtcggtga aggagtccga gggagacctg gtcaagcctg ggcttccct dacactcacc     60 tgcacagcct ctggaatcga cttcagtgcc ggctactaca tgtgctgggt ccgccaggct    120
ccagggaagg ggctggagtt gatcgcatgc atttatgctg gtcgtagtct aacactttc    180 tacgcgagct gggcgaaagg ccgattcacc atctccagag cctcgtcgac cacggtgact    240
ctggcgatga ccagtctgac agccgcggac acggccacct atttctgtgc gagagatggg    300
gctagcagtg gctactactt taagttgtgg ggcccaggca ccctggtcac cgtctcttca    360
```

<210> SEQ ID NO 116
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 116

```
gagctcgtga tgacccagac tccatctccc gtgtctgcag ctgtgggagg cacagtcagc    60
atcagttgcc aggccagtaa gagtgtttat aataacaatg ccttatcctg gtaccagcag    120
aaaccagggc agcctcccaa actcctgatc tattctgcat ccactctggc atctggggtc    180
ccatcgcggt tcagcggcag tggttctggg acagagttca ctctcaccat cagcggcgtg    240
cagtgtgacg atgctgccac ttactattgt gcaggcggtt atagtattat tagtgataat    300
ggtttcggcg gagggaccga ggtggtggtc aaa                                 333
```

<210> SEQ ID NO 117
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 117

```
cgagcagtcg ggaaggagtc cgagggaggc ctggtccagc ctgagggatc cctgacactc    60
acctgcacag cttctggatt ctccttcagt agaagcgact acatgtgttg ggtccgccag    120
gctccaggga agggactgga gtggatcgga tggattgatc ctggttatag tgacacttac    180
tacgcgagct gggcgcaagg ccgaaccacc atctccaaag cctcgtcgac cacggtgact    240
ctgcagatga ccagtctgac agtcgcggac acggccacct atttctgtgc gagagatttg    300
gggtttgata gtaatttgtg ggcccaggc accctggtca ccatctcctc a              351
```

<210> SEQ ID NO 118
<211> LENGTH: 333
<212> TYPE: DNA
<213> ORGANISM: Artificial sequence
<220> FEATURE:

<223> OTHER INFORMATION: Synthetic oligonucleotide

<400> SEQUENCE: 118

```
gagctcgatc tgacccagac tccagcctcc gtggaggcag ctgtgggagg cacagtcacc      60
atcaattgcc aggccagtca gagcattaat agttggttat cctggtatca gcagaaacca    120
gggcagcgtc ccaaactcct gatctacgaa gcatccactc tggcatctgg ggtctcatcg    180
cggttcagtg gcagtggatc tgggacacag ttcactctca ccatcagcgg cgtgcagtgt    240
gacgatgctg ccacttacta ctgtcaacag ggttatagtt atagtaatgt tgataataat    300
attttcggcg agggaccga ggtggtggtc aaa                                   333
```

<210> SEQ ID NO 119
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 119

```
cagtcgctgg aggagtccgg gggaggcctg gtccagcctg agggatccct gacactcacc      60
tgcacagctt ctggattctc cttcagtcgt ggcgactacg tgtgctgggt ccgccaggct    120
ccagggaagg gactggagtg gatcggatgg attgatgttg gtagtgttat tgaaagttac    180
tacgcgacct gggcgaaagg ccgattcacc atctccaaaa cctcgtcgac cacggtgact    240
ctgcaaatga ctagtctgac agtcgcggac acggccactt atttctgtgc gagagatttg    300
ggttttgata ctaatttgtg gggcccaggc accctggtca ccgtctcctc a             351
```

<210> SEQ ID NO 120
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 120

```
gagctcgtga tgacccagac tccagcctcc gtggaggcag ctgtgggagg cacagtcacc      60
atcaattgcc aggccagtga gagcattagt atctatttaa actggtatca gcagaaacca    120
gggcagcctc ccaagctcct gatttatcag gcatcgaaac tggcatctgg ggtcccatcg    180
cggttcaaag gcagtggatc tgggacagag ttcactctca ccatcagcga cctggagtgt    240
gccgatgctg ccacttacta ctgtcaaagc catgattatc gtattggtcg tagtgattgt    300
aatgttttcg gcggagggac caatgtggaa atcaaa                              336
```

<210> SEQ ID NO 121
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 121

Gln Ser Val Lys Glu Ser Gly Gly Asp Leu Val Lys Pro Gly Ala Ser
1               5                   10                  15

Leu Thr Leu Thr Cys Thr Ala Ser Gly Ile Asp Phe Ser Ala Gly Tyr
            20                  25                  30

Tyr Met Cys Trp Val Arg Gln Ala Pro Gly Lys Gly Leu Glu Leu Ile
        35                  40                  45

```
Ala Cys Ile Tyr Ala Gly Arg Ser Leu Asn Thr Phe Tyr Ala Ser Trp
 50                  55                  60

Ala Lys Gly Arg Phe Thr Ile Ser Arg Ala Ser Ser Thr Thr Val Thr
 65                  70                  75                  80

Leu Ala Met Thr Ser Leu Thr Ala Ala Asp Thr Ala Thr Tyr Phe Cys
                 85                  90                  95

Ala Arg Asp Gly Ala Ser Ser Gly Tyr Tyr Phe Lys Leu Trp Gly Pro
            100                 105                 110

Gly Thr Leu Val Thr Ile Ser Ser
        115                 120
```

<210> SEQ ID NO 122
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 122

```
Glu Leu Asp Met Thr Gln Thr Pro Ala Ser Val Glu Val Ala Val Gly
 1               5                  10                  15

Gly Thr Val Thr Ile Lys Cys Gln Ala Ser Gln Ser Ile Gly Ser Asn
             20                  25                  30

Leu Ala Trp Tyr Gln Gln Lys Pro Gly Gln Arg Pro Asn Val Leu Ile
         35                  40                  45

Tyr Asp Ala Ser Asn Leu Ala Ser Gly Val Ser Ser Arg Phe Lys Gly
 50                  55                  60

Ser Gly Ser Gly Thr Gln Phe Thr Leu Thr Ile Ser Gly Gly Glu Cys
 65                  70                  75                  80

Ala Asp Ala Ala Thr Tyr Tyr Cys Gln Gln Gly Tyr Ser Asp Asn Tyr
                 85                  90                  95

Leu Asp Asn Ala Phe Gly Gly Gly Thr Glu Val Val Val Lys
            100                 105                 110
```

<210> SEQ ID NO 123
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 123

```
Glu Gln Ser Leu Glu Glu Ser Glu Gly Leu Val Gln Pro Glu Gly Ser
 1               5                  10                  15

Ser Leu Thr Leu Thr Cys Thr Ala Ser Gly Phe Ser Phe Ser Arg Ser
             20                  25                  30

Asp Tyr Met Cys Trp Val Arg Gln Ala Pro Gly Lys Gly Leu Glu Trp
         35                  40                  45

Ile Gly Trp Ile Asp Pro Gly Tyr Ser Asp Thr Tyr Tyr Ala Ser Trp
 50                  55                  60

Ala Gln Gly Arg Thr Thr Ile Ser Lys Ala Ser Ser Thr Thr Val Thr
 65                  70                  75                  80

Leu Gln Met Thr Ser Leu Thr Val Ala Asp Thr Ala Thr Tyr Phe Cys
                 85                  90                  95

Ala Arg Asp Leu Gly Phe Asp Ser Asn Leu Trp Gly Pro Gly Thr Leu
            100                 105                 110

Val Thr Ile Ser Ser
        115
```

<210> SEQ ID NO 124
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 124

Glu Leu Asp Leu Thr Gln Thr Pro Ala Ser Val Ser Glu Pro Val Gly
1               5                   10                  15

Gly Thr Val Thr Ile Lys Cys Gln Ala Ser Gln Ser Ile Asn Ser Tyr
            20                  25                  30

Leu Ser Trp Tyr Gln Gln Lys Pro Gly Gln Pro Pro Lys Leu Leu Ile
        35                  40                  45

Tyr Gln Ala Ser Lys Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Ser Tyr Asp Tyr Arg Ile Ser
                85                  90                  95

Gly Ser Asp Gly Asn Val Phe Gly Gly Thr Asn Val Glu Ile Lys
            100                 105                 110

<210> SEQ ID NO 125
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 125

Ser Ser Arg Val Lys Glu Ser Gly Gly Asp Leu Val Lys Pro Gly Ala
1               5                   10                  15

Ser Leu Thr Leu Thr Cys Lys Ala Ser Gly Phe Ser Phe Ser Ser Gly
            20                  25                  30

Tyr Tyr Ile Cys Trp Val Arg Gln Ala Pro Gly Lys Gly Leu Glu Trp
        35                  40                  45

Ile Ala Cys Ile Tyr Gly Gly Asn Asn Pro Tyr Tyr Ala Asn Trp
    50                  55                  60

Val Asn Gly Arg Phe Thr Thr Ser Lys Thr Ser Thr Thr Val Thr
65                  70                  75                  80

Leu Gln Met Thr Asn Leu Thr Gly Ala Asp Thr Ala Thr Tyr Phe Cys
                85                  90                  95

Ala Arg Lys Asp Ile Asn Ile Gly Gly Ala Tyr Glu Leu Trp Gly Pro
            100                 105                 110

Gly Thr Leu Val Thr Ile Ser Ser
        115                 120

<210> SEQ ID NO 126
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 126

Glu Leu Val Met Thr Gln Thr Pro Ala Ser Val Ser Glu Pro Val Gly
1               5                   10                  15

```
Gly Thr Val Thr Ile Asn Cys Gln Ala Ser Gln Ser Ile Ser Ser Ser
            20                  25                  30

Tyr Leu Ser Trp Tyr Gln Gln Lys Pro Gly Gln Pro Pro Lys Leu Leu
        35                  40                  45

Ile Tyr Lys Ala Ser Thr Leu Ala Ser Gly Val Pro Ser Arg Phe Lys
 50                  55                  60

Gly Ser Gly Ser Gly Thr Gln Phe Ser Leu Thr Ile Ser Asp Leu Glu
 65                  70                  75                  80

Cys Ala Asp Ala Ala Thr Tyr Tyr Cys Gln Tyr Ser Asp Trp Ala Asn
                85                  90                  95

Ser Tyr Gly Asn Ala Phe Gly Gly Thr Glu Val Val Lys
                100                 105                 110
```

<210> SEQ ID NO 127
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 127

```
Gln Ser Val Lys Glu Ser Glu Gly Gly Leu Val Gln Pro Glu Gly Ser
 1               5                  10                  15

Leu Thr Leu Thr Cys Thr Ala Ser Gly Phe Ser Phe Ser Asn Ser Asp
            20                  25                  30

Tyr Met Cys Trp Val Arg Gln Ala Pro Gly Lys Gly Leu Glu Trp Ile
        35                  40                  45

Gly Trp Ile Asp Leu Val Gly Asn Thr Asn Ser Tyr Tyr Ala Ser Trp
 50                  55                  60

Ala Lys Gly Arg Phe Thr Ile Ser Lys Thr Ser Ser Thr Thr Val Ala
 65                  70                  75                  80

Leu Gln Met Thr Ser Leu Thr Val Ala Asp Thr Ala Thr Tyr Phe Cys
                85                  90                  95

Ala Arg Asp Leu Gly Phe Asp Thr Asn Leu Trp Gly Pro Gly Thr Leu
                100                 105                 110

Val Thr Val Ser Ser
        115
```

<210> SEQ ID NO 128
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 128

```
Glu Leu Asp Leu Thr Gln Thr Pro Ala Ser Val Ser Ala Ala Val Gly
 1               5                  10                  15

Gly Thr Val Thr Ile Asn Cys Gln Ala Ser Gln Asn Ile Asn Ser Trp
            20                  25                  30

Leu Ser Trp Tyr Gln Gln Lys Pro Gly Gln Arg Pro Lys Leu Leu Ile
        35                  40                  45

Tyr Gln Ala Ser Lys Leu Pro Ser Gly Val Pro Ser Arg Phe Lys Gly
 50                  55                  60

Ser Gly Ser Gly Thr Gln Phe Thr Leu Thr Ile Ser Asp Leu Glu Cys
 65                  70                  75                  80

Ala Asp Ala Ala Thr Tyr Tyr Cys Gln Ser His Asp Tyr Arg Thr Thr
                85                  90                  95
```

```
Gly Ser Tyr Gly Asn Val Phe Gly Gly Gly Thr Glu Val Glu Ile Lys
            100                 105                 110
```

<210> SEQ ID NO 129
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 129

```
Gln Ser Leu Glu Glu Ser Gly Gly Leu Val Gln Pro Gly Gly Ser
1               5                   10                  15

Leu Thr Leu Thr Cys Thr Ala Ser Gly Phe Ser Phe Ser Arg Gly Asp
                20                  25                  30

Tyr Met Cys Trp Val Arg Gln Ala Pro Gly Lys Gly Leu Glu Trp Ile
            35                  40                  45

Gly Trp Ile Asp Val Gly Arg Asp Asn Asp Ser Tyr Tyr Ala Thr Trp
        50                  55                  60

Ala Lys Gly Arg Phe Ser Ile Ser Lys Thr Ser Ser Thr Thr Val Thr
65                  70                  75                  80

Leu Gln Met Thr Ser Leu Thr Val Ala Asp Thr Ala Thr Tyr Phe Cys
                85                  90                  95

Ala Arg Asp Leu Gly Phe Asp Thr Asn Leu Trp Gly Pro Gly Thr Leu
            100                 105                 110

Val Thr Val Ser Ser
        115
```

<210> SEQ ID NO 130
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 130

```
Glu Leu Asp Met Thr Gln Thr Pro Ala Ser Val Ser Ala Ala Val Gly
1               5                   10                  15

Gly Thr Val Thr Ile Asn Cys Gln Ala Ser Gln Asn Ile Asn Ser Trp
                20                  25                  30

Leu Ser Trp Tyr Gln Gln Lys Pro Gly Gln Pro Pro Lys Leu Leu Ile
            35                  40                  45

Tyr Gln Ala Ser Lys Leu Ala Ser Gly Val Pro Ser Arg Leu Lys Gly
        50                  55                  60

Ser Gly Ser Gly Thr Gln Phe Ser Leu Thr Ile Ser Asp Leu Glu Cys
65                  70                  75                  80

Ala Asp Gly Ala Thr Tyr Tyr Cys Gln Ser Tyr Asp Tyr Arg Ser Ser
                85                  90                  95

Gly Asn Gly Gly Asn Val Phe Gly Gly Gly Thr Glu Val Glu Ile Lys
            100                 105                 110
```

<210> SEQ ID NO 131
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 131

Gln Ser Val Lys Glu Ser Glu Gly Gly Leu Val Gln Pro Glu Gly Ser
1               5                   10                  15

Leu Thr Leu Thr Cys Thr Ala Ser Gly Phe Ser Phe Ser Ser Tyr
            20                  25                  30

Tyr Met Cys Trp Val Arg Gln Ala Pro Gly Lys Gly Leu Glu Trp Ile
            35                  40                  45

Gly Cys Ile Tyr Leu Gly Asn Asn Glu Asn Thr Ala Tyr Thr Ser Trp
        50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Thr Thr Tyr Phe Cys
                85                  90                  95

Ala Arg Asp Thr Ser Gly Gly Ser Asp Tyr Tyr Phe Gly Leu Trp Gly
                100                 105                 110

Pro Gly Thr Leu Val Thr Ile Ser Ser
            115                 120

<210> SEQ ID NO 132
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 132

Glu Leu Asp Leu Thr Gln Thr Pro Ala Ser Val Glu Val Ala Val Gly
1               5                   10                  15

Gly Thr Val Thr Ile Lys Cys Gln Ala Ser His Arg Ile Lys Thr Tyr
            20                  25                  30

Leu Ala Trp Tyr Gln Gln Lys Pro Gly Gln Pro Pro Lys Leu Leu Ile
            35                  40                  45

Tyr Gly Ala Ser Thr Leu Ala Ser Gly Val Pro Ser Arg Phe Lys Gly
        50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Tyr Ser Asp Gly Asn
                85                  90                  95

Val Asp Asn Val Phe Gly Gly Gly Thr Glu Val Glu Ile Lys
                100                 105                 110

<210> SEQ ID NO 133
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 133

Glu Gln Ser Val Glu Glu Ser Gly Gly Gly Leu Val Gln Pro Glu Gly
1               5                   10                  15

Ser Leu Thr Leu Thr Cys Thr Ala Ser Gly Phe Ser Phe Ser Ser Arg
            20                  25                  30

Asp Tyr Met Cys Trp Val Arg Gln Ala Pro Gly Lys Gly Leu Glu Trp
            35                  40                  45

Ile Gly Trp Ile Asp Val Gly Tyr Thr Asp Ala Tyr Tyr Ala Ser Trp
        50                  55                  60

Ala Lys Gly Arg Phe Thr Ile Ser Arg Thr Ser Ser Thr Thr Val Thr
65                  70                  75                  80

Leu Gln Met Thr Ser Leu Thr Val Ala Asp Thr Ala Thr Tyr Phe Cys
                85                  90                  95

Ala Arg Asp Leu Gly Phe Asp Ser Asn Leu Trp Gly Pro Gly Thr Leu
            100                 105                 110

Val Thr Ile Ser Ser
            115

<210> SEQ ID NO 134
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 134

Glu Leu Val Leu Thr Gln Thr Pro Ala Ser Val Ser Ala Ala Val Gly
1               5                   10                  15

Gly Thr Val Ser Ile Asn Cys Gln Ser Ser Gln Asn Ile Tyr Ser Gly
                20                  25                  30

Leu Ala Trp Tyr Gln Gln Lys Pro Gly Gln Pro Pro Lys Leu Leu Ile
            35                  40                  45

Tyr Gly Ala Ser Thr Leu Ala Ser Gly Val Ser Ser Arg Phe Lys Gly
        50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Thr Gly Tyr Trp Thr Gly Ser
                85                  90                  95

Ser Asp Tyr Ile Gly Phe Gly Gly Gly Thr Asn Val Glu Ile Lys
            100                 105                 110

<210> SEQ ID NO 135
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 135

Glu Gln Ser Val Lys Gly Ser Glu Gly Gly Leu Val Gln Pro Glu Gly
1               5                   10                  15

Ser Leu Thr Leu Thr Cys Thr Ala Ser Gly Phe Ser Phe Ser Arg Ser
                20                  25                  30

Asp Tyr Met Cys Trp Val Arg Gln Ala Pro Gly Lys Gly Leu Glu Trp
            35                  40                  45

Ile Gly Trp Ile Asp Pro Gly Tyr Ser Asp Thr Tyr Tyr Ala Ser Trp
        50                  55                  60

Ala Gln Gly Arg Thr Thr Ile Ser Lys Ala Ser Ser Thr Thr Val Thr
65                  70                  75                  80

Leu Gln Met Thr Ser Leu Thr Val Ala Asp Thr Ala Thr Tyr Phe Cys
                85                  90                  95

Ala Arg Asp Leu Gly Phe Asp Ser Asn Leu Trp Gly Pro Gly Thr Leu
            100                 105                 110

Val Thr Val Ser Ser
            115

<210> SEQ ID NO 136
<211> LENGTH: 111
<212> TYPE: PRT

```
<213> ORGANISM: Artificial sequence
<220> FEATURE:
<223> OTHER INFORMATION: Synthetic polypeptide

<400> SEQUENCE: 136

Thr Gln Thr Pro Ala Ser Val Ser Ala Ala Val Gly Gly Thr Val Ser
1               5                   10                  15

Ile Asn Cys Gln Ser Ser Gln Ser Val Tyr Lys Asn Ala Tyr Leu Ser
            20                  25                  30

Tyr Tyr Leu Ala Trp Tyr Gln Gln Lys Pro Gly Gln Pro Pro Lys Leu
        35                  40                  45

Leu Ile Tyr Trp Ala Ser Thr Leu Ala Ser Gly Val Pro Ser Arg Phe
50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Ala Ala Glu Tyr Ser Asn
                85                  90                  95

Asp Ser Asp Asn Gly Phe Gly Gly Gly Thr Asn Val Glu Ile Lys
            100                 105                 110

<210> SEQ ID NO 137
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 137

Gln Ser Leu Glu Glu Ser Gly Gly Gly Leu Val Lys Pro Gly Gly Thr
1               5                   10                  15

Pro Thr Leu Thr Cys Thr Ala Ser Gly Phe Ser Phe Ser Arg Gly Asp
            20                  25                  30

Tyr Met Cys Trp Val Arg Gln Ala Pro Gly Lys Gly Leu Glu Trp Ile
        35                  40                  45

Gly Trp Ile Asp Ala Gly Ser Gly Ser Lys Gly Tyr Tyr Ala Arg Trp
50                  55                  60

Ala Lys Gly Arg Phe Thr Ile Ser Lys Thr Ser Ser Thr Thr Val Thr
65                  70                  75                  80

Leu Gln Met Thr Ser Val Thr Val Ala Asp Thr Ala Thr Tyr Phe Cys
                85                  90                  95

Ala Arg Asp Leu Gly Phe Asp Thr Asn Leu Trp Gly Pro Gly Thr Leu
            100                 105                 110

Val Thr Ile Ser Ser
        115

<210> SEQ ID NO 138
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 138

Glu Leu Val Met Thr Gln Thr Pro Ser Pro Val Ser Ala Ala Val Gly
1               5                   10                  15

Gly Thr Val Ser Ile Ser Cys Gln Ala Ser Lys Ser Val Tyr Asn Asn
            20                  25                  30

Asn Ala Leu Ser Trp Tyr Gln Gln Lys Pro Gly Gln Pro Pro Lys Leu
        35                  40                  45
```

```
Leu Ile Tyr Ser Ala Ser Thr Leu Ala Ser Gly Val Pro Ser Arg Phe
         50                  55                  60

Ser Gly Ser Gly Ser Gly Thr Glu Phe Thr Leu Thr Ile Ser Gly Val
 65                  70                  75                  80

Gln Cys Asp Asp Ala Ala Thr Tyr Tyr Cys Ala Cys Gly Tyr Ser Ile
                 85                  90                  95

Ile Ser Asp Asn Gly Phe Gly Gly Gly Thr Asn Val Glu Ile Lys
            100                 105                 110
```

<210> SEQ ID NO 139
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 139

```
Glu Gln Ser Val Glu Glu Ser Gly Gly Gly Leu Val Gln Pro Glu Gly
 1               5                  10                  15

Ser Leu Thr Leu Thr Cys Thr Ala Ser Gly Phe Ser Phe Ser Arg Ser
             20                  25                  30

Asp Tyr Met Cys Trp Val Arg Gln Ala Pro Gly Lys Gly Leu Glu Trp
         35                  40                  45

Ile Gly Trp Ile Asp Pro Gly Tyr Ser Asp Thr Tyr Tyr Ala Ser Trp
     50                  55                  60

Ala Gln Gly Arg Thr Thr Ile Ser Lys Ala Ser Ser Thr Thr Val Thr
 65                  70                  75                  80

Leu Gln Met Thr Ser Leu Thr Val Ala Asp Thr Ala Thr Tyr Phe Cys
                 85                  90                  95

Ala Arg Asp Leu Gly Phe Asp Ser Asn Leu Trp Gly Pro Gly Thr Leu
            100                 105                 110

Val Thr Val Ser Ser
            115
```

<210> SEQ ID NO 140
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 140

```
Glu Leu Asp Met Thr Gln Thr Pro Ala Ser Val Ser Glu Pro Val Gly
 1               5                  10                  15

Gly Thr Val Thr Ile Asn Cys Gln Ala Ser Gln Ser Ile Ser Ser Ser
             20                  25                  30

Tyr Leu Ser Trp Tyr Gln Gln Lys Pro Gly Gln Pro Pro Lys Leu Leu
         35                  40                  45

Ile Tyr Tyr Ala Ser Thr Leu Ala Ser Gly Val Ser Ser Arg Phe Lys
     50                  55                  60

Gly Ser Gly Ser Gly Thr Gln Phe Thr Leu Thr Ile Ser Asp Leu Glu
 65                  70                  75                  80

Cys Asp Asp Ala Ala Thr Tyr Tyr Cys Gln Gly Gly Tyr Ser Gly Tyr
                 85                  90                  95

Ile Asn Ser Phe Gly Gly Gly Thr Glu Val Val Val Lys
            100                 105
```

<210> SEQ ID NO 141
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 141

Glu Gln Ser Val Glu Glu Ser Gly Gly Gly Leu Val Lys Pro Gly Ala
1               5                   10                  15

Ser Leu Thr Leu Thr Cys Lys Ala Ser Gly Phe Ser Phe Ser Asp Asn
            20                  25                  30

Tyr Trp Ile Tyr Trp Val Arg Gln Ala Pro Gly Lys Gly Leu Glu Trp
        35                  40                  45

Ile Gly Tyr Ile Tyr Thr Gly Ser Gly Ser Thr Tyr Tyr Ala Ser Trp
    50                  55                  60

Ala Lys Gly Arg Ser Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Val Arg Asp Leu Tyr Gly Asp Ile Glu His Val Pro Phe Trp Gly Pro
            100                 105                 110

Gly Thr Leu Val Thr Val Ser Ser
        115                 120

<210> SEQ ID NO 142
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 142

Glu Leu Val Met Thr Gln Thr Pro Ser Pro Val Ser Ala Ala Val Gly
1               5                   10                  15

Gly Thr Val Ser Ile Ser Cys Gln Ala Ser Lys Ser Val Tyr Asn Asn
            20                  25                  30

Asn Ala Leu Ser Trp Tyr Gln Gln Lys Pro Gly Gln Pro Pro Lys Leu
        35                  40                  45

Leu Ile Tyr Ser Ala Ser Thr Leu Ala Ser Gly Val Pro Ser Arg Phe
    50                  55                  60

Ser Gly Ser Gly Ser Gly Thr Glu Phe Thr Leu Thr Ile Ser Gly Val
65                  70                  75                  80

Gln Cys Asp Asp Ala Ala Thr Tyr Tyr Cys Ala Gly Gly Tyr Ser Ile
                85                  90                  95

Ile Ser Asp Asn Gly Phe Gly Gly Thr Glu Leu Glu Ile Lys
            100                 105                 110

<210> SEQ ID NO 143
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 143

Gln Ser Val Glu Glu Ser Gly Gly Asp Leu Val Lys Pro Gly Ala Ser
1               5                   10                  15

Leu Thr Leu Thr Cys Thr Ala Ser Gly Ile Asp Phe Ser Ala Gly Tyr
            20                  25                  30

Tyr Met Cys Trp Val Arg Gln Ala Pro Gly Lys Gly Leu Glu Leu Ile
            35                  40                  45

Ala Cys Ile Tyr Ala Gly Arg Ser Leu Asn Thr Phe Tyr Ala Ser Trp
 50                  55                  60

Ala Lys Gly Arg Phe Thr Ile Ser Arg Ala Ser Ser Thr Thr Val Thr
 65                  70                  75                  80

Leu Ala Met Thr Ser Leu Thr Ala Ala Asp Thr Ala Thr Tyr Phe Cys
            85                  90                  95

Ala Arg Asp Gly Ala Ser Ser Gly Tyr Tyr Phe Lys Leu Trp Gly Pro
            100                 105                 110

Gly Thr Leu Val Thr Ile Ser Ser
            115                 120

<210> SEQ ID NO 144
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 144

Glu Leu Val Met Thr Gln Thr Pro Ser Pro Val Ser Ala Ala Val Gly
 1               5                  10                  15

Gly Thr Val Thr Ile Asn Cys Gln Ser Ser Gln Ser Val Tyr Ser Asn
            20                  25                  30

Asn Arg Leu Ala Trp Tyr Gln Gln Lys Pro Gly Gln Pro Pro Lys Leu
            35                  40                  45

Leu Val Tyr Tyr Ala Ala Thr Leu Ala Ser Gly Val Pro Ser Arg Phe
 50                  55                  60

Lys Gly Ser Gly Tyr Gly Thr Gln Ser Thr Leu Thr Ile Ala Asp Val
 65                  70                  75                  80

Val Cys Asp Asp Ala Ala Thr Tyr Tyr Cys Ala Gly Tyr Lys Thr Ala
            85                  90                  95

Asp Ser Asp Gly Ile Ala Phe Gly Gly Gly Thr Glu Val Val Val Lys
            100                 105                 110

<210> SEQ ID NO 145
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 145

Gln Ser Val Lys Glu Ser Glu Gly Asp Leu Val Lys Pro Gly Ala Ser
 1               5                  10                  15

Leu Thr Leu Thr Cys Thr Ala Ser Gly Ile Asp Phe Ser Ala Gly Tyr
            20                  25                  30

Tyr Met Cys Trp Val Arg Gln Ala Pro Gly Lys Gly Leu Glu Leu Ile
            35                  40                  45

Ala Cys Ile Tyr Ala Gly Arg Ser Leu Asn Thr Phe Tyr Ala Ser Trp
 50                  55                  60

Ala Lys Gly Arg Phe Thr Ile Ser Arg Ala Ser Ser Thr Thr Val Thr
 65                  70                  75                  80

Leu Ala Met Thr Ser Leu Thr Ala Ala Asp Thr Ala Thr Tyr Phe Cys
            85                  90                  95

Ala Arg Asp Gly Ala Ser Ser Gly Tyr Tyr Phe Lys Leu Trp Gly Pro

```
                 100                 105                 110

Gly Thr Leu Val Thr Val Ser Ser
        115                 120

<210> SEQ ID NO 146
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 146

Glu Leu Val Met Thr Gln Thr Pro Ser Pro Val Ser Ala Ala Val Gly
1               5                   10                  15

Gly Thr Val Ser Ile Ser Cys Gln Ala Ser Lys Ser Val Tyr Asn Asn
                20                  25                  30

Asn Ala Leu Ser Trp Tyr Gln Gln Lys Pro Gly Gln Pro Pro Lys Leu
            35                  40                  45

Leu Ile Tyr Ser Ala Ser Thr Leu Ala Ser Gly Val Pro Ser Arg Phe
        50                  55                  60

Ser Gly Ser Gly Ser Gly Thr Glu Phe Thr Leu Thr Ile Ser Gly Val
65                  70                  75                  80

Gln Cys Asp Asp Ala Ala Thr Tyr Tyr Cys Ala Gly Gly Tyr Ser Ile
                85                  90                  95

Ile Ser Asp Asn Gly Phe Gly Gly Gly Thr Glu Val Val Val Lys
            100                 105                 110

<210> SEQ ID NO 147
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 147

Arg Ala Val Gly Lys Glu Ser Glu Gly Gly Leu Val Gln Pro Glu Gly
1               5                   10                  15

Ser Leu Thr Leu Thr Cys Thr Ala Ser Gly Phe Ser Phe Ser Arg Ser
                20                  25                  30

Asp Tyr Met Cys Trp Val Arg Gln Ala Pro Gly Lys Gly Leu Glu Trp
            35                  40                  45

Ile Gly Trp Ile Asp Pro Gly Tyr Ser Asp Thr Tyr Tyr Ala Ser Trp
        50                  55                  60

Ala Gln Gly Arg Thr Thr Ile Ser Lys Ala Ser Ser Thr Thr Val Thr
65                  70                  75                  80

Leu Gln Met Thr Ser Leu Thr Val Ala Asp Thr Ala Thr Tyr Phe Cys
                85                  90                  95

Ala Arg Asp Leu Gly Phe Asp Ser Asn Leu Trp Gly Pro Gly Thr Leu
            100                 105                 110

Val Thr Ile Ser Ser
        115

<210> SEQ ID NO 148
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 148
```

Glu Leu Asp Leu Thr Gln Thr Pro Ala Ser Val Ala Ala Val Gly
1               5                   10                  15

Gly Thr Val Thr Ile Asn Cys Gln Ala Ser Gln Ser Ile Asn Ser Trp
                20                  25                  30

Leu Ser Trp Tyr Gln Gln Lys Pro Gly Gln Arg Pro Lys Leu Leu Ile
            35                  40                  45

Tyr Glu Ala Ser Thr Leu Ala Ser Gly Val Ser Ser Arg Phe Ser Gly
50                  55                  60

Ser Gly Ser Gly Thr Gln Phe Thr Leu Thr Ile Ser Gly Val Gln Cys
65                  70                  75                  80

Asp Asp Ala Ala Thr Tyr Tyr Cys Gln Gln Gly Tyr Ser Tyr Ser Asn
                85                  90                  95

Val Asp Asn Asn Ile Phe Gly Gly Gly Thr Glu Val Val Val Lys
                100                 105                 110

<210> SEQ ID NO 149
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 149

Gln Ser Leu Glu Glu Ser Gly Gly Gly Leu Val Gln Pro Glu Gly Ser
1               5                   10                  15

Leu Thr Leu Thr Cys Thr Ala Ser Gly Phe Ser Phe Ser Arg Gly Asp
                20                  25                  30

Tyr Val Cys Trp Val Arg Gln Ala Pro Gly Lys Gly Leu Glu Trp Ile
            35                  40                  45

Gly Trp Ile Asp Val Gly Ser Val Ile Glu Ser Tyr Tyr Ala Thr Trp
50                  55                  60

Ala Lys Gly Arg Phe Thr Ile Ser Lys Thr Ser Ser Thr Thr Val Thr
65                  70                  75                  80

Leu Gln Met Thr Ser Leu Thr Val Ala Asp Thr Ala Thr Tyr Phe Cys
                85                  90                  95

Ala Arg Asp Leu Gly Phe Asp Thr Asn Leu Trp Gly Pro Gly Thr Leu
                100                 105                 110

Val Thr Val Ser Ser
            115

<210> SEQ ID NO 150
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 150

Glu Leu Val Met Thr Gln Thr Pro Ala Ser Val Glu Ala Ala Val Gly
1               5                   10                  15

Gly Thr Val Thr Ile Asn Cys Gln Ala Ser Glu Ser Ile Ser Ile Tyr
                20                  25                  30

Leu Asn Trp Tyr Gln Gln Lys Pro Gly Gln Pro Pro Lys Leu Leu Ile
            35                  40                  45

Tyr Gln Ala Ser Lys Leu Ala Ser Gly Val Pro Ser Arg Phe Lys Gly
50                  55                  60

Ser Gly Ser Gly Thr Glu Phe Thr Leu Thr Ile Ser Asp Leu Glu Cys

```
                 65                  70                  75                  80
Ala Asp Ala Ala Thr Tyr Tyr Cys Gln Ser His Asp Tyr Arg Ile Gly
                         85                  90                  95

Arg Ser Asp Cys Asn Val Phe Gly Gly Gly Thr Asn Val Glu Ile Lys
                100                 105                 110
```

<210> SEQ ID NO 151
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 151

```
gaggtccagc tgctggagag cggaggagga ctggtgcagc ccggaggatc tttaagactg      60
agctgtgccg ccagcggctt cagcttcagc agcggctact acatctgctg ggtgagacaa     120
gctcccggta aaggtttaga gtggatcgct tgtatctacg gcggcaacaa caacccctac     180
tacgccaact gggtgaacgg cagattcacc atctctcgtg acaacagcaa gaacacttta     240
tatttacaga tgaactcttt aagggccgag acaccgccg tgtactactg cgctcgtaag      300
gacatcaaca tcggcggcgc ctatgagctg tggggccaag gtactttagt gaccgtgagc     360
agc                                                                   363
```

<210> SEQ ID NO 152
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 152

```
gacatccaga tgacccagag ccctagctct ttaagcgcca gcgtgggcga cagagtgacc      60
atcacttgtc aagctagcca gagcatcagc agcagctatt taagctggta ccagcagaag     120
cccggcaagg cccccaagct gctgatctac aaggccagca cactggccag cggcgtgcct     180
tctcgtttta gcggcagcgg cagcggaacc gacttcactt taaccatcag ctctttacag     240
cccgaggact tcgccaccta ctactgccag tacagcgact gggccaacag ctatggcaac     300
gccttcggcg gcggcaccaa ggtggagatc aag                                   333
```

<210> SEQ ID NO 153
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 153

```
gaggtccagc tgctggagag cggaggagga ctggtgcagc ccggaggatc tttaagactg      60
agctgtgccg ccagcggctt cagcttcagc agcggctact acatctgctg ggtgagacaa     120
gctcccggta aaggtttaga gtggatcgct tgtatctacg gcggcaacag caacccctac     180
tacgccaact gggtgaacgg cagattcacc atctctcgtg acaacagcaa gaacacttta     240
tatttacaga tgaactcttt aagggccgag acaccgccg tgtactactg cgctcgtaag      300
gacatcaaca tcggcggcgc ctatgagctg tggggccaag gtactttagt gaccgtgagc     360
agc                                                                   363
```

<210> SEQ ID NO 154
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 154

```
gaggtccagc tgctggagag cggaggagga ctggtgcagc ccggaggatc tttaagactg      60
agctgtgccg ccagcggctt cagcttcagc agcggctact acatctgctg ggtgagacaa     120
gctcccggta aaggtttaga gtggatcgct tgtatctacg gcggcaacag caacccctac     180
tacgccaact gggtgaacgg cagattcacc acctctcgtg acaacagcaa gaacacttta     240
tatttacaga tgaactcttt aagggccgag gacaccgccg tgtactactg cgctcgtaag     300
gacatcaaca tcggcggcgc ctatgagctg tggggccaag gtactttagt gaccgtgagc     360
agc                                                                   363
```

<210> SEQ ID NO 155
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 155

```
gaggtccagc tgctggaaag cggaggagga ctggtgcagc ccggtggctc tttaagactg      60
agctgcgctg ccagcggctt cagcttcagc agcggctact acatctgctg ggtgagacaa     120
gctcccggta agggtttaga gtggatcgct tgtatctacg gcggcaacaa caacccctac     180
tacgccaact gggtgaacgg tcgtttcacc acctctcgtg acaacagcaa gaacacttta     240
tatttacaga tgaactcttt aagggccgag gacaccgccg tgtactactg cgctaggaag     300
gacatcaaca tcggcggcgc ctacgaactg tggggacaag gtactttagt gaccgtgagc     360
agc                                                                   363
```

<210> SEQ ID NO 156
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 156

```
gaggtccagc tgctggagag cggaggagga ctggtgcagc ccggaggatc tttaagactg      60
agctgtgccg ccagcggctt caccttcagc agcggctact acatctgctg ggtgagacaa     120
gctcccggta aaggtttaga gtggatcgct tgtatctacg gcggcaacag caacccctac     180
tacgccaact gggtgaacgg cagattcacc atctctcgtg acaacagcaa gaacacttta     240
tatttacaga tgaactcttt aagggccgag gacaccgccg tgtactactg cgctcgtaag     300
gacatcaaca tcggcggcgc ctatgagctg tggggccaag gtactttagt gaccgtgagc     360
agc                                                                   363
```

<210> SEQ ID NO 157
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 157

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Tyr Ile Cys Trp Val Arg Gln Ala Pro Gly Lys Gly Leu Glu Trp
        35                  40                  45

Ile Ala Cys Ile Tyr Gly Gly Asn Asn Pro Tyr Tyr Ala Asn Trp
    50                  55                  60

Val Asn Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Lys Asp Ile Asn Ile Gly Gly Ala Tyr Glu Leu Trp Gly
            100                 105                 110

Gln Gly Thr Leu Val Thr Val Ser Ser
            115                 120

<210> SEQ ID NO 158
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 158

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Ser
            20                  25                  30

Tyr Ser Leu Ser Trp Tyr Gln Gln Lys Pro Gly Lys Ala Pro Lys Leu Leu
        35                  40                  45

Ile Tyr Lys Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Tyr Ser Asp Trp Ala Asn
                85                  90                  95

Ser Tyr Gly Asn Ala Phe Gly Gly Gly Thr Lys Val Glu Ile Lys
            100                 105                 110

<210> SEQ ID NO 159
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Tyr Ile Cys Trp Val Arg Gln Ala Pro Gly Lys Gly Leu Glu Trp
        35                  40                  45

Ile Ala Cys Ile Tyr Gly Gly Asn Ser Asn Pro Tyr Tyr Ala Asn Trp
    50                  55                  60

```
Val Asn Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Arg Lys Asp Ile Asn Ile Gly Gly Ala Tyr Glu Leu Trp Gly
            100                 105                 110

Gln Gly Thr Leu Val Thr Val Ser Ser
            115                 120

<210> SEQ ID NO 160
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 160

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Ser Phe Ser Ser Gly
             20                  25                  30

Tyr Tyr Ile Cys Trp Val Arg Gln Ala Pro Gly Lys Gly Leu Glu Trp
         35                  40                  45

Ile Ala Cys Ile Tyr Gly Gly Asn Ser Asn Pro Tyr Tyr Ala Asn Trp
     50                  55                  60

Val Asn Gly Arg Phe Thr Thr Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Arg Lys Asp Ile Asn Ile Gly Gly Ala Tyr Glu Leu Trp Gly
            100                 105                 110

Gln Gly Thr Leu Val Thr Val Ser Ser
            115                 120

<210> SEQ ID NO 161
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 161

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Ser Phe Ser Ser Gly
             20                  25                  30

Tyr Tyr Ile Cys Trp Val Arg Gln Ala Pro Gly Lys Gly Leu Glu Trp
         35                  40                  45

Ile Ala Cys Ile Tyr Gly Gly Asn Asn Asn Pro Tyr Tyr Ala Asn Trp
     50                  55                  60

Val Asn Gly Arg Phe Thr Thr Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Arg Lys Asp Ile Asn Ile Gly Gly Ala Tyr Glu Leu Trp Gly
            100                 105                 110

Gln Gly Thr Leu Val Thr Val Ser Ser
            115                 120
```

<210> SEQ ID NO 162
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Gly
            20                  25                  30

Tyr Tyr Ile Cys Trp Val Arg Gln Ala Pro Gly Lys Gly Leu Glu Trp
        35                  40                  45

Ile Ala Cys Ile Tyr Gly Gly Asn Ser Asn Pro Tyr Tyr Ala Asn Trp
    50                  55                  60

Val Asn Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Lys Asp Ile Asn Ile Gly Gly Ala Tyr Glu Leu Trp Gly
            100                 105                 110

Gln Gly Thr Leu Val Thr Val Ser Ser
        115                 120

<210> SEQ ID NO 163
<211> LENGTH: 97
<212> TYPE: PRT
<213> ORGANISM: Homo sapiens

<400> SEQUENCE: 163

Pro Pro Pro Pro Gln Pro Ala Arg Ser Ala Ser Ser Ser Thr Ile Asn
1               5                   10                  15

Leu Met Val Ser Thr Glu Pro Leu Ala Leu Thr Glu Thr Asp Ile Cys
            20                  25                  30

Lys Leu Pro Lys Asp Glu Gly Thr Cys Arg Asp Phe Ile Leu Lys Trp
        35                  40                  45

Tyr Tyr Asp Pro Asn Thr Lys Ser Cys Ala Arg Phe Trp Tyr Gly Gly
    50                  55                  60

Cys Gly Gly Asn Glu Asn Lys Phe Gly Ser Gln Lys Glu Cys Glu Lys
65                  70                  75                  80

Val Cys Ala Pro Val Leu Ala Lys Pro Gly Val Ile Ser Val Met Gly
                85                  90                  95

Thr

<210> SEQ ID NO 164
<211> LENGTH: 88
<212> TYPE: PRT
<213> ORGANISM: Mus musculus

<400> SEQUENCE: 164

Pro Pro Pro Leu Gln Ala Ala His Arg Ala Ser Ser Ser Thr Ile Asn
1               5                   10                  15

Leu Met Val Asn Thr Glu Pro Leu Phe Leu Thr Lys Thr Asp Ile Cys
            20                  25                  30

Lys Leu Ser Arg Asp Ala Gly Thr Cys Val Asp Phe Lys Leu Leu Trp
        35                  40                  45

-continued

```
His Tyr Asp Leu Glu Ser Lys Ser Cys Lys Arg Phe Trp Tyr Gly Gly
     50              55                  60

Cys Gly Gly Asn Glu Asn Arg Phe His Ser Gln Glu Glu Cys Glu Lys
65              70                  75                  80

Met Cys Ser Pro Asp Leu Leu Val
                85
```

MONOCLONAL ANTIBODIES AGAINST ENDOTROPHIN AND THE USE THEREOF

PRIORITY CLAIM

This application is a national phase application under 35 U.S.C. § 371 of International Application No. PCT/US2019/049653, filed Sep. 5, 2019, which claims benefit of priority to U.S. Provisional Application Ser. No. 62/727,140, filed Sep. 5, 2018, the entire contents of each of which are hereby incorporated by reference.

BACKGROUND

1. Field

The present invention relates generally to the fields of medicine, immunology, and cancer biology. More particularly, it concerns antibodies that neutralize human endotrophin and methods of their use.

2. Description of Related Art

Obesity potently enhances the risk for tumor development (Park et al., 2014). While this holds true for almost all cancer types, particular subsets of cancers are more affected than others. These include pancreatic, liver, colon and endometrial, as well as postmenopausal breast cancer (Calle et al., 2003). The underlying mechanistic connections however, remain only at an early stage of investigation. In breast cancer, it is clear that stromal adipocytes are involved in tumor progression, as the transformed ductal epithelial cells break through the basal lamina and start their growth in the adipocyte-rich environment of the mammary gland stroma (Iyengar et al., 2005; Iyengar et al., 2003).

Previously, a carboxy-terminal cleavage product of collagen VIa3, which is referred to as endotrophin, was identified as a critical player of tumor progression in the murine mammary gland (Park & Scherer, 2012a; Park & Scherer, 2012b). The role of endotrophin in tumor progression, metastatic growth, and fibrosis have been established through a series of experimental approaches based on both genetic gain- and loss-of-function models, as well as neutralizing antibody treatment (Park & Scherer, 2012a; Park & Scherer, 2012b). While an upregulation of endotrophin using histological analysis in a host of human tumor samples was reported, it remained unclear whether endotrophin was an effective growth stimulator for human breast cancers cells as well (Park & Scherer, 2013). Furthermore, compositions for use in inhibiting the action of endotrophin have yet to be characterized.

SUMMARY

In a first embodiment the invention provides a monoclonal antibody or antibody fragment, wherein the antibody or antibody fragment is characterized by clone-paired heavy and light chain CDR sequences from Tables 1 and 2, respectively. In some aspects, the antibody or antibody fragment is encoded by light and heavy chain variable sequences according to clone-paired sequences from Table 3. In certain aspects, the antibody or antibody fragment is encoded by light and heavy chain variable sequences having at least 70%, 80%, 85%, 86%, 87%, 88%, 89%, 90%, 91%, 92%, 93%, 94%, 95%, 96%, 97%, 98%, or 99% identity to clone-paired sequences from Table 3. In several aspects, said antibody or antibody fragment comprises light and heavy chain variable sequences according to clone-paired sequences from Table 4. In further aspects, the antibody or antibody fragment is encoded by light and heavy chain variable sequences having at least 70%, 80%, 85%, 86%, 87%, 88%, 89%, 90%, 91%, 92%, 93%, 94%, 95%, 96%, 97%, 98%, or 99% identity to clone-paired variable sequences from Table 4.

In additional aspects, the antibody or antibody fragment is a humanized antibody. In particular aspects, the antibody or antibody fragment is encoded by light and heavy chain variable sequences according to clone-paired sequences from Table 7. In some aspects, the antibody or antibody fragment is encoded by light and heavy chain variable sequences having at least 70%, 80%, 85%, 86%, 87%, 88%, 89%, 90%, 91%, 92%, 93%, 94%, 95%, 96%, 97%, 98%, or 99% identity to clone-paired sequences from Table 7. In certain aspects, the said antibody or antibody fragment comprises light and heavy chain variable sequences according to clone-paired sequences from Table 8. In specific aspects, the antibody or antibody fragment is encoded by light and heavy chain variable sequences having at least 70%, 80%, 85%, 86%, 87%, 88%, 89%, 90%, 91%, 92%, 93%, 94%, 95%, 96%, 97%, 98%, or 99% identity to clone-paired variable sequences from Table 8.

In still further aspects, the antibody fragment is a monovalent scFv (single chain fragment variable) antibody, divalent scFv, Fab fragment, F(ab') 2 fragment, F(ab') 3 fragment, Fv fragment, or single chain antibody. In another aspect, the antibody is a chimeric antibody or bispecific antibody. In an additional aspect, the antibody is an IgG antibody or a recombinant IgG antibody or antibody fragment. In some specific aspects, the antibody is conjugated or fused to an imaging agent or a cytotoxic agent.

A further embodiment of the invention provides a hybridoma or engineered cell encoding an antibody or antibody fragment as described in the embodiment and aspects described above.

In yet a further embodiment, there is provided a method of treating a patient having a cancer or a fibroid disease, the method comprising administering an effective amount of an antibody or antibody fragment as described in the embodiment and aspects described above. In certain aspects, the cancer patient has been determined to express an elevated level of endotrophin relative to a control patient. In another aspect, the method is further defined as a method for increasing chemosensitivity to platinum-based chemotherapy in the patient. In particular aspects, the cancer is a breast cancer or colon cancer.

In further aspects, the method additionally comprises administering at least a second anti-cancer therapy. In some aspects, the second anti-cancer therapy is a chemotherapy, radiotherapy, gene therapy, surgery, hormonal therapy, anti-angiogenic therapy or cytokine therapy. In a specific aspect, the chemotherapy comprises a platinum-based chemotherapy. In several aspects, the platinum-based chemotherapy is cisplatin, oxaliplatin, or carboplatin. In another aspect, the method further comprises administering thiazolidinedione to the patient.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects. As used herein, the term "about" means within 20%, more preferably within 10% and most preferably within 5%.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

(FIG. 1A) Western blot analysis of immunoprecipitated endotrophin (Col6A3) from human plasma. (FIG. 1B) The C-terminal endotrophin sequence in mice and humans. The sequence highlighted in blue denotes the portion used to produce recombinant endotrophin. Mass Spectroscopy sequencing of the human endotrophin elutant identified an additional 14 N-terminal amino acids (red highlight). The arrows indicate the MMP consensus sites. (Human=SEQ ID NO: 163; Mouse=SEQ ID NO: 164) (FIG. 1C) Higher levels of plasma endotrophin collected from peripheral blood in breast cancer patients (n=195) than that in normal donors (n=40). (FIG. 1D) Enhanced gene expression of collagen 6α3 (Col6α3) in tumor tissue, when compared to healthy tissue collected from tumor distal sites. Data from 111 breast cancer patients from data generated by the TCGA Research Network (FIG. 1E) Kaplan-Meier survival curves of breast cancer patients stratified by the mRNA expression level of Col6α3. Data generated by the TCGA Research Network.

(FIG. 2A) T47D breast cancer cells ($5\times10^5$ cells) were plated into 6-well plates and treated with endotrophin (0.1 ug/mL) three times (every other day). Total RNA was then extracted from each well. The EMT marker genes Twist, Snail, Cdh2 and Cdh1 were determined by qRT-PCR, then normalized to GAPDH. (FIG. 2B) Primary human mesothelial cells ($5\times10^5$ cells) were plated into a 6-well plate and were treated with endotrophin (0.1 μg/mL and 1 μg/mL) three times (every other day). Total RNA was extracted from each well and EM genes Twist, Snail, Cdh2 and Cdh1 were determined by qRT-PCR and normalized to GAPDH. (FIG. 2C) HUVEC cells (40,000 cells) were plated into 24-well plate. When the cells reached 90% confluence, the monolayer was scratched with a 1 mL pipette tip to create 2 perpendicular straight lines across the center of the well. Cells were then treated with increasing concentrations of endotrophin (10 pg/mL, 100 μg/mL, 1 ng/mL, 10 ng/mL, 0.1 μg/mL and 1 μg/mL). Images were obtained using a Nikon Cool Scope microscope (Nikon) after a 20 hr incubation. Migrating cell numbers were evaluated using ImageJ software. (FIG. 2D) HUVEC cells ($5\times10^5$ cells) were plated at the top chamber in a trans-well plate. Endotrophin (0.1 μg/mL) was then added with or without 1% FBS in the lower chamber, then incubated for 16 hr. Images were then obtained on a Nikon Cool Scope microscope (Nikon) after a 16 hr incubation. (FIG. 2E) HUVEC cells (40,000 cells) were plated into a gel-coated 24-well plate. Cells were then treated with endotrophin (10 pg/mL, 100 μg/mL, 1 ng/mL, 10 ng/ml, 0.1 μg/mL and 1 μg/mL), with or without 1% FBS for 16 hr. A cell-permeable dye, Calcein, was added for fluorescent monitoring of tube formation. Images were then obtained using a Nikon Cool Scope microscope (Nikon) after 16 hr. (FIG. 2F) SC macrophage cells (50,000 cells) were seeded at the top of the chamber. Endotrophin (0.1 μg/mL) was added with 1% FBS in the lower chamber and incubated for 2 hr. Migrated cells were then counted after 2 hr. In all cases, data was represented as mean±SD and statistical significance (*** $p<0.0001$) was calculated using an unpaired Student's t-test.

(FIG. 3A) MCF7 breast cancer cells (20,000 cells) were plated into a 96-well plate. Cells were then treated with 10 μm cisplatin, 10 μm cisplatin/100 ng/mL endotrophin, and 10 μm cisplatin/100 ng/mL endotrophin/10 μg/mL ETPmAb4 for 24 hr. Cell survival was measured using a CellTiter One Solution Cell Proliferation Assay. Statistical significance of the curve fit parameters was tested using the extra sum of squares F test with P<0.05 considered significant. Goodness of curve fit is described using r2. Mean±SEM, n=3. (FIG. 3B) ETP transfected MCF7 cells (100,000 cells) were plated into a 24-well plate with 500 μL media. Then 4 μL of supernatant was loaded for Western blotting. It is estimated that approximately 1 ng of ETP was loaded, compared with the standard ETP (2 ng band). The concentration yields approximately 0.052 pg secreted ETP/hr/cell. (FIG. 3C) Total RNA was extracted from MCF7, HCC1395, MDAMB231, ZR-75 and MDAMB453 cells. ETP expression was determined by qRT-PCR and normalized to GAPDH. (FIG. 3D) ETP transfected MCF7 cells ($1\times10^5$ cells) were plated at the bottom chamber in a trans-well plate. Then 10 μg/mL, 2 μg/mL, 0.4 μg/mL and 0.08 μg/mL ETPmAb4 was added to the bottom on day two. SC macrophage cells (50,000 cells) were seeded at the top of the chamber on day three. Migrated cells were counted after a 2 hr incubation. In all cases, data was represented as mean±SD, and statistical significance (*** $p<0.0001$) was calculated using an unpaired Student's t-test.

(FIG. 4A) GFP-MCF7 cells ($2\times10^6$ cells) (control) and ETP transfected MCF7 cells ($2\times10^6$ cells) were implanted into nude mice for 6-weeks. Tumor volume was determined by caliper measurement. Data are represented as mean±SD (n=8/group) and  p<0.001, * p<0.0001 by calculated by using an unpaired Student's t-test. (FIG. 4B) Endomucin immunofluorescence staining of tumor tissues from MCF7 and ETP transfected MCF7 tumors. Mac2 immunofluorescence staining for tumor tissues from MCF7 and ETP transfected MCF7 tumors. (FIG. 4C) Half-life determination of ETPmAb4 in the mouse.

(FIG. 5A) ETP transfected MCF7 cells ($2\times10^6$ cells) were implanted into nude mice. An estradiol pellet (0.72 mg) was implanted into nude mice. Then (i) 20 mg/kg ETPmAb4, (ii) 10 mg/kg ETPmAb4 with 10 mg/kg control IgG, (iii) 5 mg/kg ETPmAb4 with 15 mg/kg control IgG, (iv) 2 mg/kg ETPmAb4 with 18 mg/kg control IgG, and (v) 20 mg/kg control IgG (twice a week) were injected after 10-days implantation for 5-weeks. Tumor volume was determined by caliper measurement. Data was represented as mean±SD (n=5/group), and * p<0.0001 by ANOVA followed by Newman-Keuls multiple comparison test. (FIG. 5B) Total RNA was prepared from tumor tissues from ETP transfected MCF7, ETPmAb4 treatment mice. The EMT markers genes Twist, Snail, Cdh2 and Cdh 1 were determined by qRT-PCR, then normalized to GAPDH. E-CAD immunofluorescence staining for tumor tissues from ETP transfected MCF7 and ETPmAb4 treatment tumor. (FIG. 5C) MCF7 and ETP transfected MCF7 cells ($2\times10^6$ cells) were implanted into nude mice. An estradiol pellet (0.72 mg) was implanted into nude mice. Then 20 mg/kg of antibody ETPmAb4 (twice a week), and 2.5 mg/kg of cisplatin (once a week) were injected after 10-days implantation for 6-weeks. Tumor volume was determined by caliper measurement. Data was represented as mean±SD (n=5/group), and * p<0.0001 by ANOVA followed by Newman-Keuls multiple comparison test.

(FIG. 6A) MDA-MB-231 cells ($2\times10^6$ cells) were implanted into nude mice. Then 2.5 mg/kg of cisplatin and 20 mg/kg of ETPmAb4 antibody (twice a week) were injected after 10-days implantation for 5-weeks. Tumor volume was determined by caliper measurement. The insert reflects a simplified analysis of control antibody versus ETPmAb4 with associated statistics. (FIG. 6B) MDA-MB-231 cells ($2\times10^6$ cells) were implanted into nude mice. Treatment was started when the tumor volume was over 30 $mm^3$. At that point, 2.5 mg/kg of cisplatin and 20 mg/kg of ETPmAb4 antibody (twice weekly) were injected for 5-weeks. Tumor volumes were determined by caliper measurements. The insert reflects a simplified analysis of control antibody versus ETPmAb4 with associated statistics. (FIG. 6C) SKOV3 cells ($2\times10^6$ cells) were implanted into nude mice. Then 2.5 mg/kg of cisplatin and 20 mg/kg of ETPmAb4 antibody (twice weekly) were injected 10-days after implantation for 5-weeks. Tumor volumes were determined by caliper measurements. The insert reflects a simplified analysis of control antibody versus ETPmAb4 with associated statistics. (FIG. 6D) MDA-MB-231 cells ($2\times10^6$ cells) were implanted into nude mice. Then 2.5 mg/kg of cisplatin, 20 mg/kg of ETPmAb4 antibody and 20 mg/kg of humanized ETPmAb4 antibody (twice a week) were injected after 10-days implantation for 5-weeks. Tumor volume was determined by caliper measurement. In all case, data was represented as mean±SEM (n=5/group), and *** P<0.0001 by 2-way ANOVA with Sidak's correction for multiple comparisons.

FIG. 8. Screening for rabbit monoclonal antibodies. MCF7 breast cancer cells (20,000 cells) were plated into a 96-well plate. Cells were then treated with 10 μm of cisplatin and 100 ng/ml of endotrophin. All 132 neutralized endotrophin antibodies were screened. Cell survival was measured using a CellTiter One Solution Cell Proliferation Assay. The different shaded bars are different clones, but only every third clone is labeled; for example, clone 1 and clone 4 have two unlabeled clones in between.

DETAILED DESCRIPTION

Figure 1A:
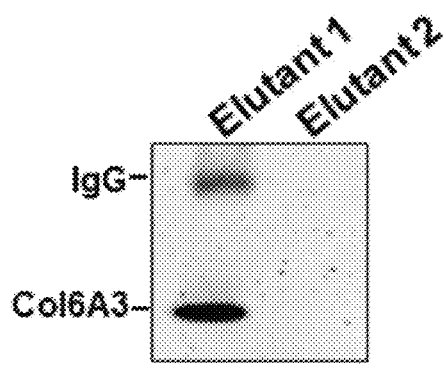
FIGS. 1A-E. Identification of plasma endotrophin and elevated endotrophin levels in breast cancer patients.

Studies have shown that endotrophin, the carboxy-terminal cleavage product of the COL6α3 chain, has potent effects on transformed mammary ductal epithelial cells in rodents. It is abundantly expressed in adipose tissue and is a chemoattractant for macrophages, exerts effects on endothelial cells and enhances the progression through epithelial-mesenchymal transition (EMT) in tumor cells. In the process, it causes tumor cells to become chemoresistant. Endotrophin is also present in human plasma. It circulates at higher levels in breast cancer patients. Provided herein are a large panel of neutralizing monoclonal antibodies against human endotrophin that are effective in tumor inhibition and enhancing chemosensitivity in a mouse tumor model. The antibodies can be used as therapeutics for the treatment of cancer and fibrosis diseases in liver, kidney, bone marrow, and adipose tissue.

Even though the role of endotrophin is believed to be predominantly paracrine in nature, acting primarily within the microenvironment, it is also postulated that a portion of the protein escapes from the local tissue and can be identified in circulation. Here, the circulating levels of endotrophin in the plasma of breast cancer patients was found to be elevated. Several recent papers have reported the plasma measurement of endotrophin in human samples, though primarily in the context of metabolic diseases. Rasmussen and colleagues (Rasmussen et al., 2017) focused on individuals with chronic kidney disease and found that urinary endotrophin predicts disease progression. They followed up on these observations and demonstrated that higher levels of an endotrophin-containing fragment are associated with all-cause mortality in patients with type 2 diabetes and microalbuminuria (Rasmussen et al., 2018). Similarly, Fenton and colleagues (Fenton et al., 2017) reported that an increase in serum endotrophin is associated with increased mortality in chronic kidney disease. Karsdal and colleagues (Karsdal et al., 2017) further utilized baseline serum endotrophin levels in type 2 diabetic patients to predict which individual would respond most effectively to insulin-sensitizing PPARy-agonist treatment. The latter set of observations has to be understood in the context of the reciprocal relationship between PPARy activity and expression of the endotrophin precursor, collagen VIa3 (Sun et al., 2017). Treatment with thiazolidinediones (TZDs), which are PPARy agonists, effectively suppress collagen VIa3 transcription, as part of its generalized anti-fibrotic properties (Khan et al., 2009). Treatment with TZDs, in the context of a mammary tumor model, further enhances cisplatinum susceptibility of mammary tumors (Park et al., 2013), at least partially reproducing the results provided here with the neutralizing antibody. This suggests that co-administration of the neutralizing antibody with TZDs may also further enhance the susceptibility of tumor cells to cisplatinum.

Endotrophin neutralization can be used as an anti-fibrotic approach as well. In high-fat diet-fed mice, treatment with a neutralizing antibody to mouse endotrophin, reduces fibrosis in adipose tissue and leads to an improvement in insulin sensitivity (Sun et al., 2014). More importantly, both the kidney, the liver and bone marrow are organs of interest with major pathologies associated with chronic pro-fibrotic responses, including an upregulation in endotrophin. Neutralizing endotrophin may be efficacious in the context of diabetic nephropathy and fatty liver disease progression, ultimately leading to hepatocellular carcinoma. As such, the present neutralizing antibodies may find important use in fibrotic diseases, as well as in the context of a host of additional tumor settings associated with an upregulation of collagen VI in general, and endotrophin specifically.

I. DEFINITIONS

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv)), mutants thereof, naturally occurring variants, fusion proteins comprising an antibody portion with an antigen recognition site of the required specificity, humanized antibodies, chimeric antibodies, and any other modified configuration of the immunoglobulin molecule that comprises an antigen recognition site of the required specificity.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single antibody; (vi) the dAb fragment which consists of a VH domain; (vii) isolated CDR regions; (viii) F(ab') 2 fragments, a bivalent fragment including two Fab' fragments linked by a disulfide bridge at the hinge region; (ix) single chain antibody molecules (e.g. single chain Fv; scFv); (x) "diabodies" with two antigen binding sites, comprising a heavy chain variable domain (VH) connected to a light chain variable domain (VL) in the same polypeptide chain; (xi) "linear antibodies" comprising a pair of tandem Fd segments (VH-CH1-VH-CH1) which, together with complementary light chain polypeptides, form a pair of antigen binding regions.

"Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. For example, the variable regions can conveniently be derived from presently known sources using readily available hybridomas or B cells from non-human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example.

A "constant region" of an antibody refers to the constant region of the antibody light chain or the constant region of the antibody heavy chain, either alone or in combination. The constant regions of the light chain (CL) and the heavy chain (CH1, CH2 or CH3, or CH4 in the case of IgM and IgE) confer important biological properties such as secretion, transplacental mobility, Fc receptor binding, complement binding, and the like. By convention the numbering of the constant region domains increases as they become more distal from the antigen binding site or amino-terminus of the antibody.

A "variable region" of an antibody refers to the variable region of the antibody light chain or the variable region of the antibody heavy chain, either alone or in combination. The variable regions of both the light (VL) and heavy (VH) chain portions determine antigen recognition and specificity. VL and VH each consist of four framework regions (FR) connected by three complementarity determining regions (CDRs) also known as hypervariable regions. The CDRs complement an antigen's shape and determine the antibody's affinity and specificity for the antigen. There are six CDRs in both VL and VH. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (the Kabat numbering scheme; see Kabat et al., Sequences of Proteins of Immunological Interest (5th ed., 1991, National Institutes of Health, Bethesda Md.)); and (2) an approach based on crystallographic studies of antigen-antibody complexes (the Chothia numbering scheme which corrects the sites of insertions and deletions (indels) in CDR-L1 and CDR-H1 suggested by Kabat; see Al-lazikani et al. (1997) J. Molec. Biol. 273:927-948)). Other numbering approach or scheme can also be used. As used herein, a CDR may refer to CDRs defined by either approach or by a combination of both approaches or by other desirable approaches. In addition, a new definition of highly conserved core, boundary and hyper-variable regions can be used.

The term "heavy chain" as used herein refers to the larger immunoglobulin subunit which associates, through its amino terminal region, with the immunoglobulin light chain. The heavy chain comprises a variable region (VH) and a constant region (CH). The constant region further comprises the CH1, hinge, CH2, and CH3 domains. In the case of IgE, IgM, and IgY, the heavy chain comprises a CH4 domain but does not have a hinge domain. Those skilled in the art will appreciate that heavy chains are classified as gamma, mu, alpha, delta, or epsilon (γ, μ, α, δ, ε), with some subclasses among them (e.g., γ1-γ4). It is the nature of this chain that determines the "class" of the antibody as IgG, IgM, IgA IgG, or IgE, respectively. The immunoglobulin subclasses (isotypes), e.g., IgG1, IgG2, IgG3, IgG4, IgA1, etc. are well characterized and are known to confer functional specialization.

The term "light chain" as used herein refers to the smaller immunoglobulin subunit which associates with the amino terminal region of a heavy chain. As with a heavy chain, a light chain comprises a variable region (VL) and a constant region (CL). Light chains are classified as either kappa or lambda (κ, λ). A pair of these can associate with a pair of any of the various heavy chains to form an immunoglobulin molecule. Also encompassed in the meaning of light chain are light chains with a lambda variable region (V-lambda) linked to a kappa constant region (C-kappa) or a kappa variable region (V-kappa) linked to a lambda constant region (C-lambda).

"Nucleic acid," "nucleic acid sequence," "oligonucleotide," "polynucleotide" or other grammatical equivalents as used herein means at least two nucleotides, either deoxyribonucleotides or ribonucleotides, or analogs thereof, covalently linked together. Polynucleotides are polymers of any length, including, e.g., 20, 50, 100, 200, 300, 500, 1000, 2000, 3000, 5000, 7000, 10,000, etc. A polynucleotide described herein generally contains phosphodiester bonds, although in some cases, nucleic acid analogs are included that may have at least one different linkage, e.g., phosphoramidate, phosphorothioate, phosphorodithioate, or O-methylphophoroamidite linkages, and peptide nucleic acid backbones and linkages. Mixtures of naturally occurring polynucleotides and analogs can be made; alternatively, mixtures of different polynucleotide analogs, and mixtures of naturally occurring polynucleotides and analogs may be made. The following are non-limiting examples of polynucleotides: a gene or gene fragment, exons, introns, messenger RNA (mRNA), transfer RNA, ribosomal RNA, ribozymes, cDNA, CRNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form. A polynucleotide is composed of a specific sequence of four nucleotide bases: adenine (A), cytosine (C), guanine (G), thymine (T), and uracil (U) for thymine when the polynucleotide is RNA. Thus, the term "polynucleotide sequence" is the alphabetical representation of a polynucleotide molecule. Unless otherwise indicated, a particular polynucleotide sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

The terms "peptide," "polypeptide" and "protein" used herein refer to polymers of amino acid residues. These terms also apply to amino acid polymers in which one or more amino acid residues is an artificial chemical mimetic of a corresponding naturally occurring amino acid, as well as to naturally occurring amino acid polymers, those containing modified residues, and non-naturally occurring amino acid polymers. In the present case, the term "polypeptide" encompasses an antibody or a fragment thereof.

Other terms used in the fields of recombinant nucleic acid technology, microbiology, immunology, antibody engineering, and molecular and cell biology as used herein will be generally understood by one of ordinary skill in the applicable arts.

II. ANTIBODIES AND MODIFICATIONS OF ANTIBODIES

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881,557, incorporated herein by reference). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024, each incorporated herein by reference.

In further embodiments, antibody molecules, or fragments thereof may be used to target some marker on the surface of a target cell. The antibody alone may serve as an effector of therapy or it may recruit other cells to actually effect cell killing. The antibody may also be conjugated to a drug or toxin (e.g., chemotherapeutic, radionuclide, ricin A chain, cholera toxin, pertussis toxin, etc.) and thus may merely serve as a targeting agent.

In certain embodiments, are antibody conjugates. The conjugate can be, for example, a specific binding agent (such as an antibody) of the invention conjugated to other proteinatious, carbohydrate, lipid, or mixed moiety molecule(s). Such antibody conjugates include, but are not limited to, modifications that include linking it to one or more polymers. In certain embodiments, an antibody is linked to one or more water-soluble polymers. In certain such embodiments, linkage to a water-soluble polymer reduces the likelihood that the antibody will precipitate in an aqueous environment, such as a physiological environment. In certain embodiments, a therapeutic antibody is linked to a water-soluble polymer. In certain embodiments, one skilled in the art can select a suitable water-soluble polymer based on considerations including, but not limited to, whether the polymer/antibody conjugate will be used in the treatment of a patient and, if so, the pharmacological profile of the antibody (e.g., half-life, dosage, activity, antigenicity, and/or other factors).

In further embodiments, the conjugate can be, for example, a cytotoxic agent. Cytotoxic agents of this type may improve antibody-mediated cytotoxicity, and include such moieties as cytokines that directly or indirectly stimulate cell death, radioisotopes, chemotherapeutic drugs (including prodrugs), bacterial toxins (e.g., *pseudomonas* exotoxin, diphtheria toxin, etc.), plant toxins (e.g., ricin, gelonin, etc.), chemical conjugates (e.g., maytansinoid toxins, calechaemicin, etc.), radioconjugates, enzyme conjugates (e.g., RNase conjugates, granzyme antibody-directed enzyme/prodrug therapy), and the like. Protein cytotoxins can be expressed as fusion proteins with the specific binding agent following ligation of a polynucleotide encoding the toxin to a polynucleotide encoding the binding agent. In still another alternative, the specific binding agent can be covalently modified to include the desired cytotoxin.

In additional embodiments antibodies, or fragments thereof, can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). The invention accordingly provides a molecule comprising an antibody molecule, wherein the molecule preferably further comprises a reporter group selected from the group consisting of a radiolabel, a fluorescent label, an enzyme, a substrate, a solid matrix, and a carrier. Such labels are well known to those of skill in the art, e.g., biotin labels are particularly contemplated. The use of such labels is well known to those of skill in the art and is described in, e.g., U.S. Pat. Nos. 3,817,837; 3,850,752; 3,996,345 and 4,277,437, each incorporated herein by reference. Other labels that will be useful include but are not limited to radioactive labels, fluorescent labels and chemiluminescent labels. U.S. Patents concerning use of such labels include for example U.S. Pat. Nos. 3,817,837; 3,850,752; 3,939,350 and 3,996,345. Any of the peptides of the present invention may comprise one, two, or more of any of these labels.

A. Monoclonal Antibodies and Production Thereof

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular embodiments, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa and lambda based on the amino acid sequences of their constant domains (CL). Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha, delta, epsilon, gamma and mu, respectively. They gamma and alpha classes are further divided into subclasses on the basis of relatively minor differences in CH sequence and function, humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}H$ when numbered in accordance with AHo; Honneger, A. and Plunkthun, A. J. Mol. Biol. 309:657-670 (2001)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The monoclonal antibodies may also be isolated from phage antibody libraries using the techniques described in Clackson et al., Nature, 352: 624-628 (1991) and Marks et al., J. Mol. Biol., 222:581-597 (1991), for example.

B. General Methods

It will be understood that monoclonal antibodies of the present invention have several applications. These include the production of diagnostic kits for use in detecting endotrophin, as well as for treating diseases associated with increased levels of endotrophin. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuberculosis*), incomplete Freund's adjuvants and aluminum hydroxide adjuvant and in humans include alum, CpG, MFP59 and combinations of immunostimulatory molecules ("Adjuvant Systems", such as AS01 or AS03). Additional experimental forms of inoculation to induce antigen-specific B cells is possible, including nanoparticle vaccines, or gene-encoded antigens delivered as DNA or RNA genes in a physical delivery system (such as lipid nanoparticle or on a gold biolistic bead), and delivered with needle, gene gun, transcutaneous electroporation device. The antigen gene also can be carried as encoded by a replication competent or defective viral vector such as adenovirus, adeno-associated virus, poxvirus, herpesvirus, or alphavirus replicon, or alternatively a virus like particle.

Methods for generating hybrids of antibody-producing cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986) and there are processes for better efficiency (Yu et al., 2008). Fusion procedures usually produce viable hybrids at low frequencies, about $1\times10^{-6}$ to $1\times10^{-8}$, but with optimized procedures one can achieve fusion efficiencies close to 1 in 200 (Yu et al., 2008). However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. Single B cells labelled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes form single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately 104 times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. For example, the epitope to which a given antibody bind may consist of a single contiguous sequence of 3 or more (e.g., 3, 4, 5, 6, 7, 8, 9, 10, 11, 12, 13, 14, 15, 16, 17, 18, 19, 20) amino acids located within the antigen molecule (e.g., a linear epitope in a domain). Alternatively, the epitope may consist of a plurality of non-contiguous amino acids (or amino acid sequences) located within the antigen molecule (e.g., a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Cross-blocking can be measured in various binding assays such as ELISA, biolayer interferometry, or surface plasmon resonance. Other methods include alanine scanning mutational analysis, peptide blot analysis (Reineke (2004) Methods Mol. Biol. 248:443-63), peptide cleavage analysis, high-resolution electron microscopy techniques using single particle reconstruction, cryoEM, or tomography, crystallographic studies and NMR analysis. In addition, methods such as epitope excision, epitope extraction and chemical modification of antigens can be employed (Tomer (2000) Prot. Sci. 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267:252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

The present disclosure includes antibodies that may bind to the same epitope, or a portion of the epitope. Likewise, the present disclosure also includes antibodies that compete for binding to a target or a fragment thereof with any of the specific exemplary antibodies described herein. One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody.

In another aspect, there are provided monoclonal antibodies having clone-paired CDRs from the heavy and light chains as illustrated in Tables 1 and 2, respectively. Such antibodies may be produced using methods described herein.

In another aspect, the antibodies may be defined by their variable sequence, which include additional "framework" regions. These are provided in Tables 3 and 4 or 7 and 8 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogeny pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy-the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85:2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One particular example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the below-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "*Lack Of Fucose On Human IgG N-Linked Oligosaccharide Improves Binding To Human Fcgamma RIII And Antibody-Dependent Cellular Toxicity*," J. Biol. Chem. 277 (30): 26733-26740; Davies J. et al. (2001) "*Expression Of GnTIII In A Recombinant Anti- CD20 CHO Production Cell Line: Expression Of Antibodies With Altered Glycoforms Leads To An Increase In ADCC Through Higher Affinity For FC Gamma RIII*," Biotechnology & Bioengineering 74 (4): 288-294). Methods of altering carbohydrate contents are known to those skilled in the art, see, e.g., Wallick, S. C. et al. (1988) "*Glycosylation Of A VH Residue Of A Monoclonal Antibody Against Alpha* (1-6) *Dextran Increases Its Affinity For Antigen*," J. Exp. Med. 168 (3): 1099-1109; Tao, M. H. et al. (1989) "*Studies Of Aglycosylated Chimeric Mouse-Human IgG. Role Of Carbohydrate In The Structure And Effector Functions Mediated By The Human IgG Constant Region,*" J. Immunol. 143 (8): 2595-2601; Routledge, E. G. et al. (1995) "*The Effect Of Aglycosylation On The Immunogenicity Of A Humanized Therapeutic CD3 Monoclonal Antibody*," Transplantation 60 (8): 847-53; Elliott, S. et al. (2003) "*Enhancement Of Therapeutic Protein In vivo Activities Through Glycoengineering*," Nature Biotechnol. 21:414-21; Shields, R. L. et al. (2002) "*Lack Of Fucose On Human IgG N-Linked Oligosaccharide Improves Binding To Human Fcgamma RIII And Antibody-Dependent Cellular Toxicity*," J. Biol. Chem. 277 (30): 26733-26740).

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

In various embodiments, one may choose to engineer sequences of the identified antibodies for a variety of reasons, such as improved expression, improved cross-reactivity or diminished off-target binding. Modified antibodies may be made by any technique known to those of skill in the art, including expression through standard molecular biological techniques, or the chemical synthesis of polypeptides. Methods for recombinant expression are addressed elsewhere in this document. The following is a general discussion of relevant goals techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as E. coli, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (NlmP) outperforms several other nucleoside modifications and their combinations in terms of translation capacity. In addition to turning off the immune/eIF2a phosphorylation-dependent inhibition of translation, incorporated NIm' nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as alphavirus replicons based on VEE virus or Sindbis virus are also contemplated. Delivery of such vectors can be performed by needle through intramuscular, subcutaneous, or intradermal routes, or by transcutaneous electroporation when in vivo expression is desired.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab') 2) that are produced, for example, by the proteolytic cleavage of the mAbs, or single-chain immunoglobulins producible, for example, via recombinant means. F(ab') antibody derivatives are monovalent, while F(ab') 2 antibody derivatives are bivalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency.

Alternatively or additionally, it may be useful to combine amino acid modifications with one or more further amino acid modifications that alter Clq binding and/or the complement dependent cytotoxicity (CDC) function of the Fc region of an IL-23p19 binding molecule. The binding polypeptide of particular interest may be one that binds to Clq and displays complement dependent cytotoxicity. Polypeptides with pre-existing Clq binding activity, optionally further having the ability to mediate CDC may be modified such that one or both of these activities are enhanced. Amino acid modifications that alter Clq and/or modify its complement dependent cytotoxicity function are described, for example, in WO/0042072, which is hereby incorporated by reference.

One can design an Fc region of an antibody with altered effector function, e.g., by modifying Clq binding and/or FcγR binding and thereby changing CDC activity and/or ADCC activity. "Effector functions" are responsible for activating or diminishing a biological activity (e.g., in a subject). Examples of effector functions include, but are not limited to: Clq binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of an antibody with improved Clq binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

A particular embodiment of the present disclosure is an isolated monoclonal antibody, or antigen binding fragment thereof, containing a substantially homogeneous glycan without sialic acid, galactose, or fucose. The monoclonal antibody comprises a heavy chain variable region and a light chain variable region, both of which may be attached to heavy chain or light chain constant regions respectively. The aforementioned substantially homogeneous glycan may be covalently attached to the heavy chain constant region.

Another embodiment of the present disclosure comprises a mAb with a novel Fc glycosylation pattern. The isolated monoclonal antibody, or antigen binding fragment thereof, is present in a substantially homogenous composition represented by the GNGN or G1/G2 glycoform. Fc glycosylation plays a significant role in anti-viral and anti-cancer properties of therapeutic mAbs. The disclosure is in line with a recent study that shows increased anti-lentivirus cell-mediated viral inhibition of a fucose free anti-HIV mAb in vitro. This embodiment of the present disclosure with homogenous glycans lacking a core fucose, showed increased protection against specific viruses by a factor greater than two-fold. Elimination of core fucose dramatically improves the ADCC activity of mAbs mediated by natural killer (NK) cells but appears to have the opposite effect on the ADCC activity of polymorphonuclear cells (PMNs).

The isolated monoclonal antibody, or antigen binding fragment thereof, comprising a substantially homogenous composition represented by the GNGN or G1/G2 glycoform exhibits increased binding affinity for Fc gamma RI and Fc gamma RIII compared to the same antibody without the substantially homogeneous GNGN glycoform and with GO, GIF, G2F, GNF, GNGNF or GNGNFX containing glycoforms. In one embodiment of the present disclosure, the antibody dissociates from Fc gamma RI with a Kd of $1\times10^{-8}$ M or less and from Fc gamma RIII with a Kd of $1\times10^{-7}$ M or less.

Glycosylation of an Fc region is typically either N-linked or O-linked. N-linked refers to the attachment of the carbohydrate moiety to the side chain of an asparagine residue. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the antibody is expressed in cells that express beta (1,4)-N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999. Cell lines can be altered to enhance or reduce or eliminate certain post-translational modifications, such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express recombinant monoclonal antibodies.

It is possible to engineer the antibody variable gene sequences obtained from human B cells to enhance their manufacturability and safety. Potential protein sequence liabilities can be identified by searching for sequence motifs associated with sites containing:
1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene for the cDNA encoding recombinant antibodies.

Protein engineering efforts in the field of development of therapeutic antibodies clearly reveal that certain sequences or residues are associated with solubility differences (Fernandez-Escamilla et al., *Nature Biotech.*, 22 (10), 1302-1306, 2004; Chennamsetty et al., *PNAS*, 106 (29), 11937-11942, 2009; Voynov et al., *Biocon. Chem.*, 21 (2), 385-392, 2010) Evidence from solubility-altering mutations in the literature indicate that some hydrophilic residues such as aspartic acid, glutamic acid, and serine contribute significantly more favorably to protein solubility than other hydrophilic residues, such as asparagine, glutamine, threonine, lysine, and arginine.

Antibodies can be engineered for enhanced biophysical properties. One can use elevated temperature to unfold antibodies to determine relative stability, using average apparent melting temperatures. Differential Scanning calorimetry (DSC) measures the heat capacity, Cp, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, $C_H2$, and $C_H3$ domains). Typically unfolding of the Fab domain produces the strongest peak. The DSC profiles and relative stability of the Fc portion show characteristic differences for the human $IgG_1$, $IgG_2$, $IgG_3$, and $IgG_4$ subclasses (Garber and Demarest, *Biochem. Biophys. Res. Commun.* 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min. One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 µg/mL.

One can determine the intrinsic solubility score of antibody sequences. The intrinsic solubility scores can be calculated using CamSol Intrinsic (Sormanni et al., *J Mol Biol* 427, 478-490, 2015). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol,* 366:449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Generally, it is thought that autoreactive clones should be eliminated during ontogeny by negative selection; however, it has become clear that many human naturally-occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., Science 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293S human embryonic kidney cells). Autoreactivity also can be surveyed using assessment of binding to tissues in tissue arrays.

B cell repertoire deep sequencing of human B cells from blood donors is being performed on a wide scale in many recent studies. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. TREATMENT OF DISEASE

Certain aspects of the present embodiments can be used to prevent or treat a disease or disorder associated with elevated levels of endotrophin. Functioning of endotrophin may be reduced by any suitable drugs. Preferably, such substances would be an anti-endotrophin antibody.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an antibody that inhibits the endotrophin.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

A. Pharmaceutical Preparations

Where clinical application of a therapeutic composition containing an inhibitory antibody is undertaken, it will generally be beneficial to prepare a pharmaceutical or therapeutic composition appropriate for the intended application. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

The therapeutic compositions of the present embodiments are advantageously administered in the form of injectable compositions either as liquid solutions or suspensions; solid forms suitable for solution in, or suspension in, liquid prior to injection may also be prepared. These preparations also may be emulsified.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered.

The practitioner responsible for administration will, in any event, determine the concentration of active ingredient(s) in a composition and appropriate dose(s) for the individual subject. The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

B. Combination Treatments

In certain embodiments, the compositions and methods of the present embodiments involve an antibody or an antibody fragment against endotrophin to inhibit its activity, in combination with a second or additional therapy. Such therapy can be applied in the treatment of any disease that is associated with elevated endotrophin. For example, the disease may be a cancer or a fibroid disease.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an antibody or antibody fragment and a second therapy. A tissue, tumor, or cell can be contacted with one or more compositions or pharmacological formulation(s) comprising one or more of the agents (i.e., antibody or antibody fragment or an anti-cancer agent), or by contacting the tissue, tumor, and/or cell with two or more distinct compositions or formulations, wherein one composition provides 1) an antibody or antibody fragment, 2) an anti-cancer agent, or 3) both an antibody or antibody fragment and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An inhibitory antibody may be administered before, during, after, or in various combinations relative to an anti-cancer treatment. The administrations may be in intervals ranging from concurrently to minutes to days to weeks. In embodiments where the antibody or antibody fragment is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations, it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an antibody therapy is "A" and an anti-cancer therapy is "B":

A/B/A B/A/B B/B/A A/A/B A/B/B B/A/A A/B/B/B B/A/B/B B/B/B/A B/B/A/B A/A/B/B A/B/A/B A/B/B/A B/B/A/A B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

i. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TMI); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine,plicomycin, gemcitabien, navelbine, farnesyl-protein tansferase inhibitors, transplatinum, and pharmaceutically acceptable salts, acids, or derivatives of any of the above.

ii. Radiotherapy

Other factors that cause DNA damage and have been used extensively include what are commonly known as y-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

iii. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis*, *Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons and, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. U.S. Pat. No. 5,824,311). It is contemplated that one or more anti-cancer therapies may be employed with the antibody therapies described herein.

iv. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

v. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents.

Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. KITS AND DIAGNOSTICS

In various aspects of the embodiments, a kit is envisioned containing therapeutic agents and/or other therapeutic and delivery agents. In some embodiments, the present disclosure contemplates a kit for preparing and/or administering a therapy of the embodiments. The kit may comprise one or more sealed vials containing any of the pharmaceutical compositions of the present embodiments. The kit may include, for example, at least one endotrophin antibody as well as reagents to prepare, formulate, and/or administer the components of the embodiments or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a therapeutic agent.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Animal experiments. NU/NU nude female mice were purchased from Charles River (Crl: NU-Foxnlnu; Strain Code 088 (Homozygous)). Breast cancer cells ($2 \times 10^6$ cells) were implanted by intraductal injection. All cell lines were mixed on ice with 1×PBS and Matrigel. Then 100 µL of mixture was injected into mice. Tumors were measured twice a week, beginning 10 days after injection, and tumor volume was calculated by length×(width) 2/2 ($mm^3$).

Recombinant endotrophin expression in HEK293 cells. To generate bioactive human endotropin for in vitro and in vivo studies and to generate neutralizing antibodies against human endotrophin, a strategy to express human endotrophin in HEK293 cells was designed (Sino Biological, Beijing, China). Briefly, the construct includes a CD33 signal peptide, followed by a His-tag, an EK-cleavage site and the predicted human endotrophin sequence; the latter consisting of 77 amino acids at the carboxy-terminal of the COL6α3 chain. After purification of the protein using a nickel column, the His-tag was removed by enterokinase cleavage, which results in the 77 amino acid human endotrophin free of tags.

Endotrophin-specific polyclonal and monoclonal antibodies. Rabbits (NZW, Charles River) were immunized with recombinantly-produced human endotrophin protein (Sino Biological, Beijing, China), using a standard immunization procedure (RevMab Biosciences, South San Francisco, CA). After 4 boosts, blood (30-40 ml/rabbit) was sampled for memory B cell isolation, using an IgG+Memory B Cell Isolation Kit (Miltenyi Biotec). After culturing individual B cells for 14 days, supernatants were tested for antibody specificity to endotrophin by ELISA. Variable gene fragments encoding the endotrophin-specific antibodies were cloned using a set of rabbit antibody gene specific primers, as described previously (Freed et al., 2013). Full-length antibodies were constructed and expressed using a mammalian expression vector system in HEK293 suspension cells (Invitrogen) (Fan et al., 2012). Antibodies were purified using a Protein A affinity resin, and the purity was confirmed on a SDS-PAGE gel. Rabbit sera were collected from blood samples for isolation of polyclonal anti-endotrophin antibodies that were used for setting up ELISA detection of circulating endotrophin in patient plasma samples.

ELISA based measurements of circulating endotrophin. Plasma samples (n=195) were collected from breast cancer patients (n=40) with informed consent under the approved Institutional Review Board protocols #HSC-MS-10$^{-0580}$ and HSC-MS-11-0559 at the University of Texas McGovern Medical School at Houston (Zhang et al., 2015). Plasma samples (10 mL) were freshly prepared from blood samples collected before surgery and were preserved at −80° C. until analysis. Plasma samples from normal donors (n=40) were obtained from an outside vendor (Cureline Inc). To quantitatively determine the levels of circulating endotrophin in human plasma collected from breast cancer patients, 96-well maxi-sorp plates (Corning Costar) were coated with rabbit polyclonal anti-endotrophin antibodies prepared in house at 20 µg/mL concentration. Plasma samples were titrated at a series of dilutions in 1×PBS, then added to an anti-endotrophin coated plate. A high affinity (1 nM) monoclonal anti-endotrophin antibody (selected in house) was biotinylated using an amine conjugation kit (Fisher Scientific), then utilized as secondary detection antibody. Streptavidin conjugated with HRP (horseradish peroxidase) (Fisher Scientific) was used for detection of endotrophin signals, using the dilution as suggested by the manufacturer. A purified endotrophin recombinant protein was titrated in a series of concentrations (0-5000 µg/mL) to establish a standard curve for calculation of endotrophin in plasma samples.

MTS assay screening endotrophin monoclonal antibodies. MCF7 breast cancer cells (20,000 cells) were plated into a 96-well plate. Cells were then treated with 10 µM of cisplatinum and 100 ng/ml of endotrophin. In total, 132 neutralized endotrophin antibodies were screened. Cell survival was measured using a CellTiter One Solution Cell Proliferation Assay. CellTiter One Solution Reagent (20 µL)

was added into each well of 96-well plate, and incubated at 37° C. for 4 hr. The plate was then read at 490 nm using a Sunrise microplate reader (TECAN).

Immunoprecipitation of Human Endotrophin. Anti-human endotrophin antibody was covalently immobilized to SulfoLink Coupling Resin (ThermoFisher) per the manufacturer's instructions. Briefly, endotrophin antibody was incubated with TCEP (ThermoFisher) for 1 hr to reduce the available sulfhydryl bonds in coupling buffer (50 mM Tris, 5 mM EDTA; pH 8.5). The reduced antibody was incubated with SulfoLink coupling resin in a gravity-flow column for 1 hr. The column was then washed with coupling buffer, quenched with L-cysteine-HCl and washed with 1 M NaCl. Following equilibration with 1×PBS, 2 mL of human plasma was passed through the affinity column twice. Un-bound proteins were washed off the column with 1×PBS and the captured endotrophin was eluted with 0.2 M glycine, pH 2.5.

Expression Analysis in Human Breast Cancer Tumors. Col6α3 mRNA expression in matched control healthy tissue and tumor tissue from 111 breast cancer patients were downloaded and extracted from data generated by the TCGA Research Network: available on the world wide web at cancergenome.nih.gov/. The data were analyzed and statistical significance was determined using the deseq2 package, using R (available on the world wide web at doi.org/10.1186/s13059-014-0550-8).

Disease Specific Survival Analysis. Probe-level mRNA expression values of Col6α3 determined by the Illumina-Bead platform were obtained from tumor lesions from 203 breast cancer patients with stage 3 tumors (available on the world wide web at journals.plos.org/plosone/article?id=10.1371/journal.pone.0019249 #s2). Tumor tissue was obtained prior to the initiation of chemotherapy. Each sample was classified as Col6α3-high if the signal was above the median expression for the population (Chrisanthar et al., 2011). Kaplan-Meier curves were generated using GraphPad Prism 7. P-value was determined using the log-rank test, and Cox proportional hazard model analysis was used to calculate hazard ratios.

Quantitative RT-PCR. Total RNA was isolated using an RNeasy kit (Qiagen) following tissue homogenization in Trizol (Invitrogen). Total RNA (1 µg) was reverse transcribed with SuperScript III reverse transcriptase (Invitrogen). Quantitative real-time PCR (qRT-PCR) was performed using a Roche Lightcycler 480. The results were calculated using the $\Delta\Delta C_t$ method using GAPDH for normalization. Primer sequences used in this study are as detailed in (Rosivatz et al., 2002).

Analysis of Anti-endotrophin Antibody Half Life. The concentration of ETP-mAb4 in mouse serum samples was determined using a commercially readily available nSMOL kit (nano-surface and molecular orientation limited proteolysis, Shimadzu Corporation, Kyoto, Japan) (Iwamoto et al., 2014), in combination with liquid chromatography tandem mass spectrometry technology (Nexera X2 UHPLC coupled to LCMS-8060 triple quadrupole mass spectrometer, Shimadzu Scientific Instruments, Columbia, MD). Commercial human plasma (5 µL) (spiked at known concentrations of ETP-mAb4) were then used to generate calibration curves, and a ProteoMass™$P_{14}$ commercial peptide standard (Millipore Sigma, St. Louis, MO) was used as an internal standard. Mouse serum (5 µL) from treated mice was employed for analysis.

Immunofluorescence Staining. Formalin-fixed paraffin-embedded tissue sections were used for immunofluorescence. De-paraffinized tissue slides were blocked in PBS-Tween with 5% BSA. Primary antibodies used were Endomucin, Mac2 and ECAD (1:200 dilution). Secondary antibodies (1:500 dilution) used were the Alexa Fluor 488 donkey anti-rabbit IgG (H+L) preparation. Fluorescence images were acquired on an Olympus FSX100 all-in-one microscope.

Analysis of Tumor Progression. Tumor onset was monitored twice weekly by palpation. Tumor sizes were measured using a digital caliper twice weekly and the volumes were calculated as length× width2)/2. Inguinal tumors were weighted to determine tumor burden. Animals were sacrificed when the tumor burden visibly affected the host, or when the tumors reached the IACUC pre-determined limit of 20 mm along one axis.

Primary Culture of Human Cells and Transwell Assays. SC macrophage cells were seeded at the top of the chamber of a trans-well plate (8 µm pore size; Costar). Endotrophin or ETP-MCF7 cells were added into the lower chamber and incubated for 2 hr. Migrated cells were then counted after 2 hr.

Isolation of Primary Human Mesothelial Cells. The mesothelial cell population was prepared from omental adipose tissue obtained from adult patients undergoing a bariatric procedure (The University of Texas Southwestern Medical Center Institutional Review Board approved this study). The tissue was minimally digested with 0.25% trypsin for 20 min at 37° C. on a rotating stand. The undigested adipose tissue was removed, and the remaining trypsin and cells were centrifuged at 600 g for 5 min at 4° C. The upper layer was discarded, and the pellet was resuspended in Media 199 supplemented with 5% fetal bovine serum (FBS), plated on a 12-well collagen coated plate and grown to confluency (1-2 weeks). When the mesothelial cells reached confluency, they were uniformly cobblestone in appearance.

In vitro Cell Migration Assay. HUVECs were seeded at the top of the chamber in a trans-well plate. Endotrophin was added to the bottom chamber with 1% FBS. After 16 hours, cells on the underside of the membrane were fixed with 10% formalin and counted. Images were acquired using a Nikon Cool Scope (Nikon).

In vitro Tube Formation Assay. HUVEC cells (40,000 cells) were plated into gel-coated 24-well plate. Cells were then treated with endotrophin with or without 1% FBS for 16 hr. A cell-permeable dye (Calcein) was added for fluorescent monitoring of tube formation. Images were then obtained on the Nikon Cool Scope (Nikon) microscope following a 16 hr incubation.

Antibody-antigen ELISA Binding Assay. Corning 96-well EIA/RIA plates were coated overnight at 4° C. with HEK293 expressed recombinant endotrophin (1 µg/mL) and blocked for 2 hr at 37° C. with 5% non-fat milk. After washing with PBST for 3 times, 100 µL of serial diluted anti-endotrophin antibodies were added and incubated for 45 min at 37° C. Subsequently, the plates were washed with PBST and incubated for 30 min with anti-rabbit or anti-human F(ab') 2 HRP-conjugated antibody (Jackson ImmunoResearch Laboratories). The immunoreactions were developed with TMB substrates (Sigma) and stopped by the addition of 2 M sulfuric acid before reading the plate at 450 nm.

Humanization of rabbit mAb. Humanization of the rabbit anti-endotrophin antibody was based a CDR-grafting strategy as described previously (Yu et al., 2010). Briefly, CDRs in the heavy and light chains of the rabbit antibody were defined by a combination of three methods: Kabat, IMGT and Paratome. The parental rabbit mAb and the most closely related human germline sequence were then aligned. Residues which are known not to be structurally critical and/or subjected to change during the in vivo maturation process were identified in the MLG analysis and humanized. DNA encoding humanized VK and VH were synthesized (GenScript). The human IgG signal peptides and a Kozak sequence were engineered at the 5' ends of the VK and VH sequences. The humanized VK and VH fragments were then cloned into human IgG1 CK and CH vectors separately. Expression, purification and quantification of the humanized mAbs are the same as those for rabbit mAbs.

Affinity Measurement with BLI. For antibody affinity measurement, antibody (20 µg/mL) was loaded onto the protein G biosensors for 4 min. Following a short baseline in kinetics buffer, the loaded biosensors were exposed to a series of recombinant LILRB4 concentrations (0.1-100 nM) and background subtraction was used to correct for sensor drifting. All experiments were performed with shaking at 1,000 rpm. Background wavelength shifts were measured from reference biosensors that were loaded only with antibody. ForteBio's data analysis software was used to fit the data to a 1:1 binding model to extract an association rate and dissociation rate. The Kd was calculated using the ratio $k_{off}/k_{on}$ (Yang et al., 2016).

Cell lines, Culture and Reagents. All breast cancer cell lines (T47D, MCF7, HCC1395, MDAMB231, ZR-75 and MDAMB453) used in this study were obtained from the Hamon Cancer Center Collection (The University of Texas Southwestern Medical Center). Cells were maintained in RPMI-1640 supplemented with penicillin-streptomycin and 5% FBS. HUVEC cells were obtained from Lonza and were maintained in EBM medium (Lonza, cc-3121). Cisplatin was obtained from Sigma-Aldrich (479306-1G). Estradiol pellets were acquired from Innovative Research of America (SE-121). Calcein was obtained from Invitrogen (C3099). Geltrex was obtained from ThermoFisher Scientific (A14132-02). CellTiter One Solution Cell Proliferation Assay was acquired from Promega (G3580). The primary antibodies used for histological analyses were as follows: E-cadherin (Novus Biologicals, #NB110$^{-56937}$), endomucin (Santa Cruz Biotechnology, #SC-65495) and Mac2 (Biolegand, #125401).

Immunoblotting. Cell lysates were harvested using NP-40 lysis buffer, supplemented with phenylmethylsulfonyl fluoride (PMSF, 1 mM), protease inhibitor (Roche), and phosphatase inhibitor (Roche). Protein samples were immunoblotted using standard methods. For culture media, differentiated 3T3-L1 adipocytes and preadipocytes were serum starved in DMEM media. Following an overnight incubation, the media was harvested and filtered (Millipore, 0.45 mm). Conditioned media was then concentrated using centrifugal filters (Amicon Ultra, 3K) at 14,000 g for 40 min. Secreted ETP was detected using a-mouse ETP polyclonal antibody, compared to COL6 (Abcam, Ab6588). The primary antibodies were detected with secondary IgG-labeled with infrared dyes emitting at 700 and 800 nm and visualized on the Licor Odessey Infrared Scanner. The scanned results were analyzed using the Odessey v2.1 software (Licor Bioscience).

Statistical Analyses. Data are presented as mean±SD. Data were analyzed by an ANOVA, followed by a Newman-Keuls multiple comparison test, or by a Student's t-test, as appropriate, with GraphPad Prism v.5 software.

Study Approval. This study was carried out in strict accordance with the recommendations in the Guide for the Care and Use of Laboratory Animals of the National Institutes of Health. All animal experiments were approved by the Institutional Animal Care and Research Advisory Committee at The University of Texas Southwestern Medical Center (Protocol Number 2015-101207-G).

Example 1—Endotrophin can be Isolated from Human Plasma

Figure 1B:
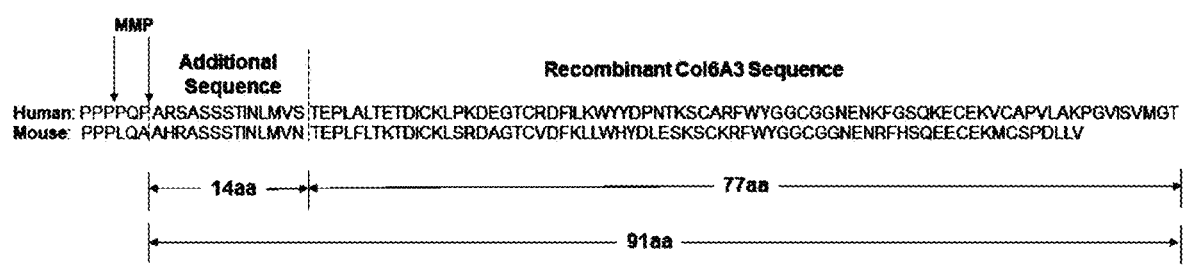

To date, a broad array of physiological responses to endotrophin in rodents are known (Park & Scherer, 2013; Park et al., 2013; Sun et al., 2017; Sun et al., 2014). A series of experiments was initiated to determine whether a similar set of responses occur in humans. Thus far, the exact nature of locally acting and circulating endotrophin has not been defined. Therefore, a rabbit polyclonal antiserum was raised against the C-terminal region of what was predicted to be human endotrophin. These antibodies were used to immunoprecipitate endotrophin from human plasma. Anti-human endotrophin antibodies were immobilized on an agarose resin by covalent thioester bonding, in order to immunoprecipitate endotrophin from human plasma from a healthy individual from a commercial source (FIG. 1A). The immunoprecipitate was resolved by SDS-PAGE, and a gel region corresponding to the estimated molecular weight of endotrophin (~$10^{-15}$ kDa) was excised for subsequent protein sequencing. This unambiguously established the presence of endotrophin in circulation in humans, and further defined endotrophin as a peptide of 91 amino acids. This closely correlates with two nearby predicted MMP14 cleavage sites (FIG. 1B).

Figure 1C:
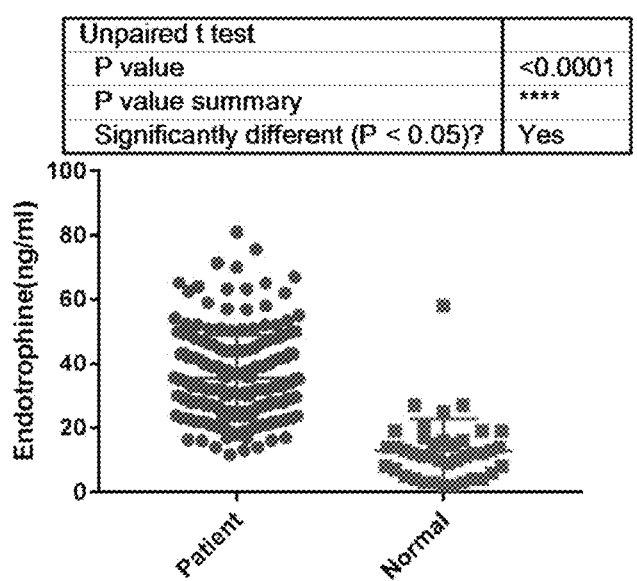
Figure 1D:
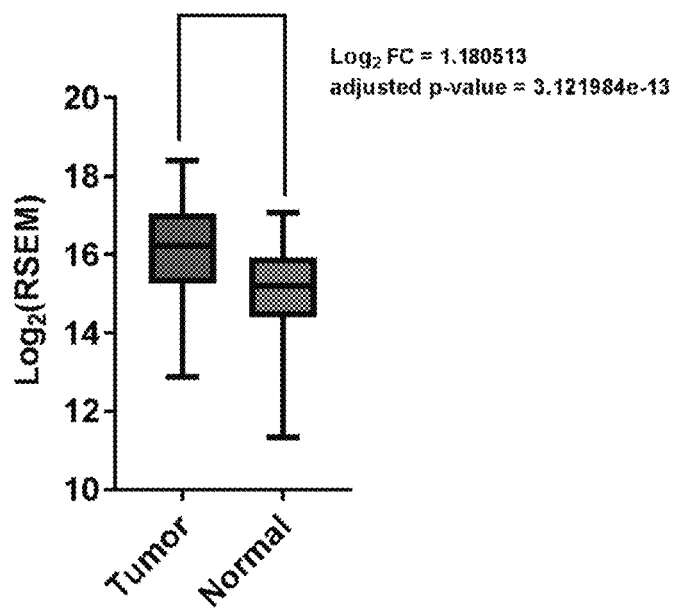
Figure 1E:
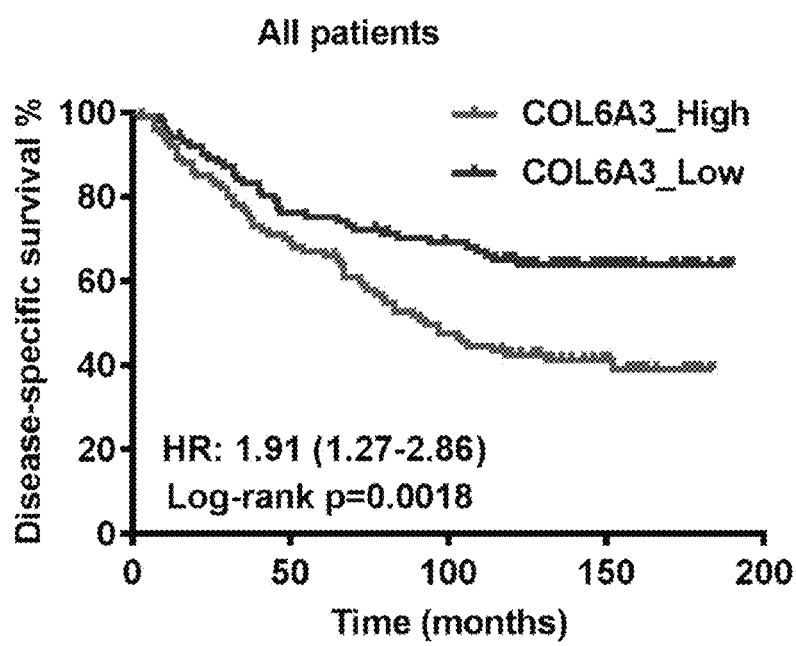

As proof-of-principle, these antibodies were combined with a rabbit monoclonal antibody against human endotrophin and developed an ELISA assay; subsequently, this assay was used to measure endotrophin in a cohort of breast cancer patients. While the size of this cohort does not allow any significant statements to be made with regards to the prevalence of endotrophin upregulation in human breast cancer patients with different subtypes, interestingly, a significant upregulation of endotrophin was observed in breast cancer patients compared to cancer-free patients (FIG. 1C). Consistent with the circulating levels of endotrophin, the gene expression levels of collagen 6a3 (Col6α3) in primary breast tumors were also increased, when compared with patient-matched non-tumor tissues (FIG. 1D). Furthermore, in primary tumors, Col6α3 expression level was significantly negatively correlated with survival in breast cancer patients treated with chemotherapy. This suggests that Col6α3 and its cleavage product endotrophin, play an important contributory role to promote tumor progression in breast cancer patients (FIG. 1E). This relationship with reduced survival rate was maintained effectively in pre-menopausal and post-menopausal breast cancers and was also independent of estrogen receptor status of the tumor cells (FIG. S1). Based on these results, recombinant endotrophin was expressed in HEK293 cells, and the protein was used to immunize rabbits for endotrophin targeting monoclonal antibodies.

Example 2—Effects of Human Endotrophin on Human Cells In Vitro

Figure 2A:
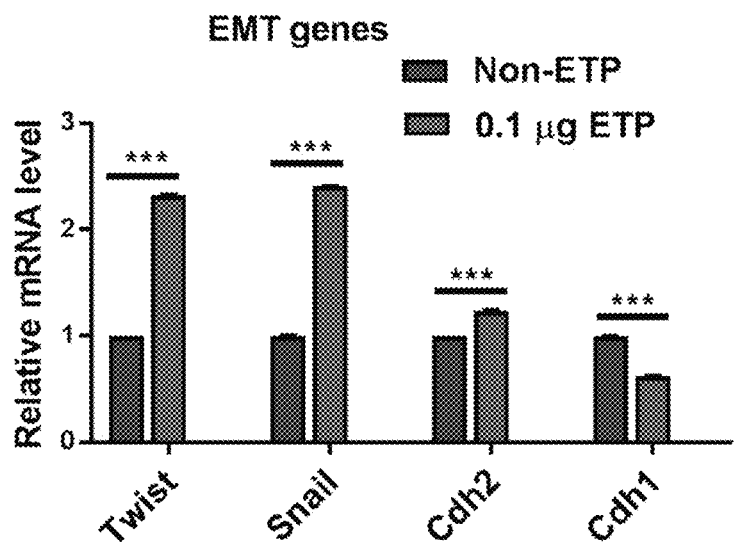
FIGS. 2A-F. Effects of human endotrophin on human cells in vitro.
Figure 2B:
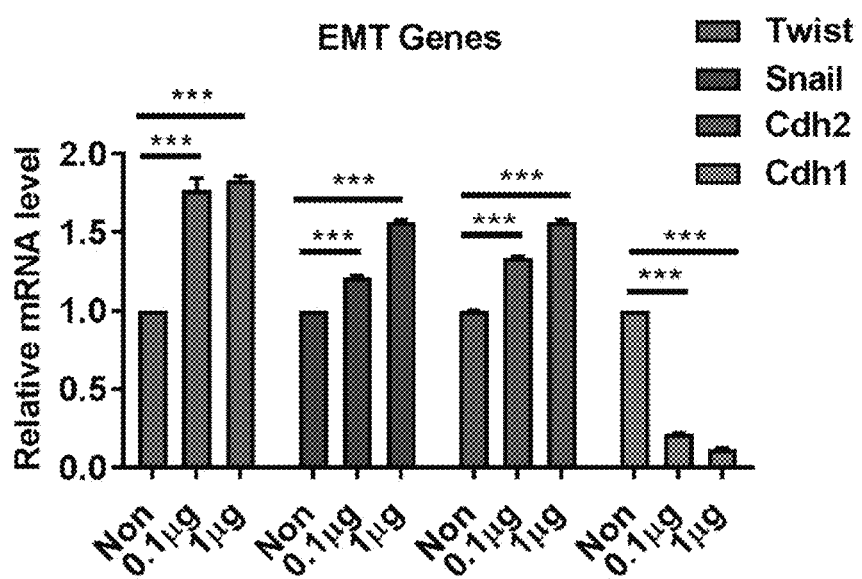

Subsequently, whether some of the initial effects described for murine endotrophin would translate for human endotrophin was assessed. To achieve this objective, the human breast cancer cell-line T47D (Keydar et al., 1979) was used to examine whether human endotrophin exerts a similar effect on human cancer cells as it does in rodents; whereby the latter effectively triggers epithelial-to-mesenchymal transition (EMT) (Park et al., 2013). After examining the transcriptional alterations that occur in response to endotrophin exposure, a significant two-fold upregulation was observed in the EMT markers Twist and Snail, with a significant but less profound increase in N-Cadherin (Cdh2) (Sciacovelli & Frezza, 2017); this was paralleled with a marked downregulation in epithelial cell marker E-cadherin (Cdh1) (FIG. 2A). In conjunction with this, primary human mesothelial cells were used to probe for the same effects (Gupta & Gupta, 2015). Consistent with what was observed for T47D cells, an upregulation of mesenchymal cell markers, along with a downregulation in Cdh1 gene expression levels, in an endotrophin dose-dependent fashion was observed (FIG. 2B).

Figure 2C:
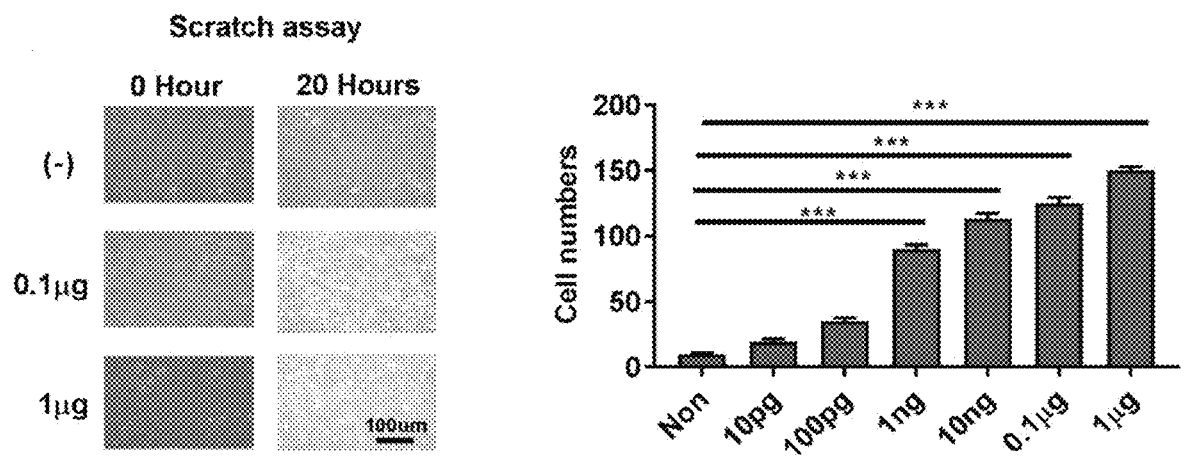
Figure 2D:
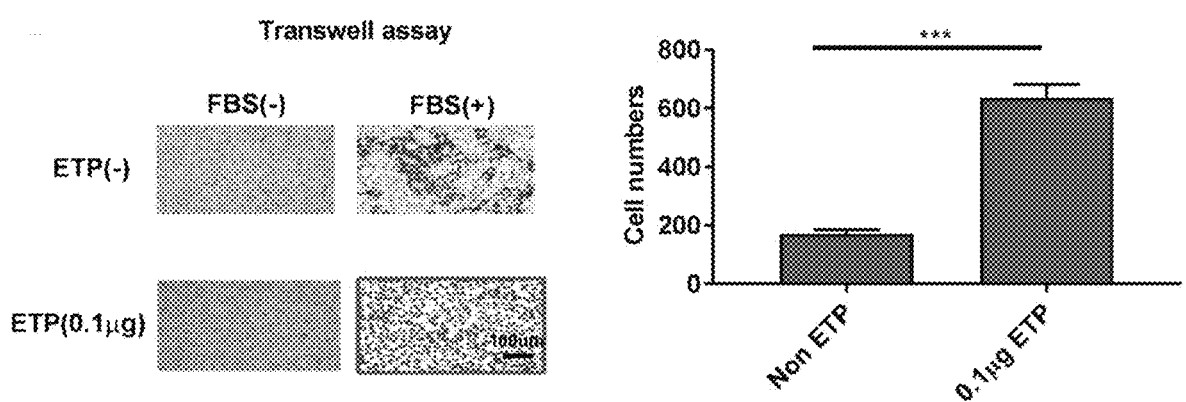

With these effects on epithelial cells validated, the impact of endotrophin on human endothelial cells was examined. For this purpose, a preparation of human umbilical vein endothelial cells (HUVECs) (15), grown in a dish to near confluence, was used. A gap was then introduced across the plate by removing cells with a cell scraper (Herren et al., 1997). Using this scratch assay, it was examined whether endotrophin in the tissue culture supernatant, could enhance the migration of HUVECs into the open space. This was the case, as judged by the quantitation of the number of cells occupying the gap, as a function of the added endotrophin concentration. In the presence of endotrophin in the medium, there was a significant enhancement in the migration of tumor cells into the existing gap (FIG. 2C). This was further corroborated in a trans-well assay with HUVECs seeded into the top chamber, and an assessment of the migratory behavior of these cells to the lower chamber, as a function of the presence or absence of recombinant endotrophin (Sakata et al., 1988). The presence of endotrophin in the lower chamber indeed significantly enhanced the trans-well migratory behavior of the HUVECs (FIG. 2D).

Figure 2E:
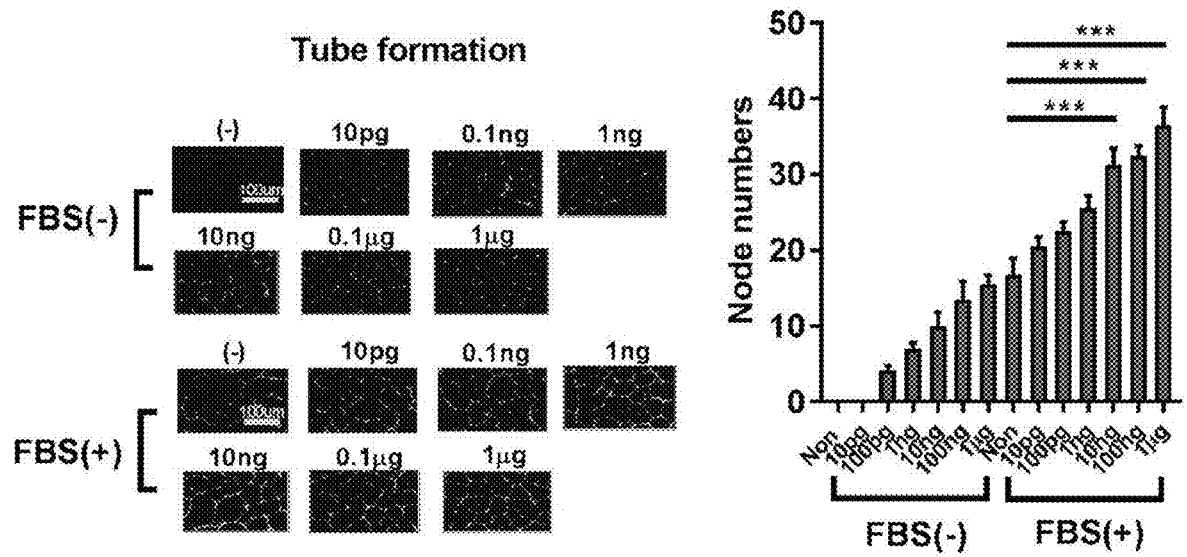

Next, an additional test with the HUVEC cells was performed. Endothelial cells, when exposed to an appropriate stimulus, form structures in vitro that reflect the pro-angiogenic properties of the system in vivo. These tube formation assays can also be performed with HUVECs (Maheshwari et al., 1991). Compared to the absence of serum, or the presence of serum containing low levels of endogenous endotrophin, serum supplemented with exogenous recombinant endotrophin showed a potent stimulatory effect on tube formation in a dose-dependent fashion (FIG. 2E) in strong support of a pro-angiogenic role of endotrophin in vivo.

Figure 2F:
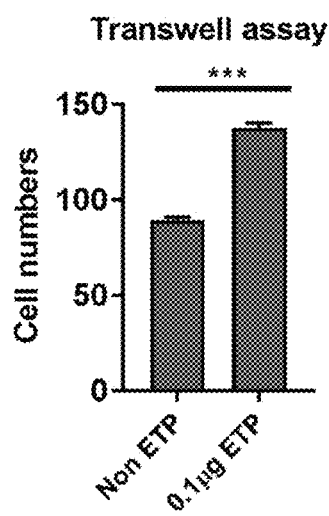

A chemoattractant effect of endotrophin on monocytes and macrophages that are recruited to tumor lesions in mice was observed. The chemoattractant properties of human endotrophin on human macrophages was assayed. Similar to the approach with HUVECs, human SC macrophages (Treves, 1985) were seeded in the top chamber, and assayed the migratory procedure of the macrophages across the well towards the bottom chamber. The presence of recombinant endotrophin in the bottom chamber strongly stimulated the migration the macrophages towards endotrophin (FIG. 2F).

Example 3—Generation and Screening of Anti-Human Endotrophin Antibodies

Using the recombinant endotrophin employed for the assays described above, monoclonal antibodies were raised in rabbits. Peripheral blood samples were collected from the immunized rabbits for B cell (CD45+CD5-CD19+) isolation from freshly prepared peripheral blood mononuclear cells (PBMCs) using a fluorescence assisted cell sorting (FACS) (BD FACSAria™ III, BD Biosciences). Single B cells were sorted into 96-well cell culture plates (Fisher Scientific) and cultured for 7-10 days. The antibodies in the culture supernatants were assayed for endotrophin binding. Cells from the positives wells were lysed, total RNA was isolated, and cDNA was synthesized using a superscript reverse transcriptase II (Invitrogen) according to the manufacturer's instructions. DNA sequences of antibody variable regions from both heavy chains and light chains were amplified by polymerase chain reaction (PCR) using a set of designed primers and cloned into a plasmid for sequencing. DNA and amino acid variable sequences are listed in the Tables 5 and 6, respectively. CDRs of the anti-endotrophin monoclonal antibodies were identified using the IMGT program (available on the world wide web at IMGT.org) and are listed in Tables 1 and 2.

Selected endotrophin binding hits were expressed as rabbit or rabbit/human chimeric IgGs using a mammalian expression vector system in human embryonic kidney (HEK293) cells (Invitrogen). Antibodies were purified using a column with protein A resin by a fast protein liquid chromatography (FPLC) separation unit. Purified endotrophin binding antibodies were characterized for their biological properties.

Figure 10:
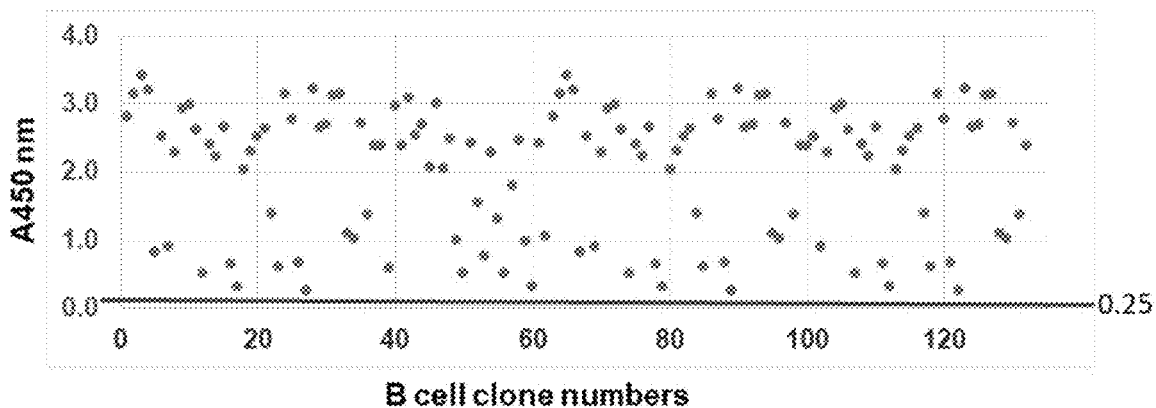
FIG. 10. Selection of endotrophin antibodies by ELISA. Human or mouse endotrophin protein (Sino Biologicals) was coated on a 96-well high binding plate over night at 4° C. in PBS. B cell culture supernatants (5 μL medium and 95 μL of PBS) were added at for binding to endotrophin antigen coated on the plate. Bound antibody was detected using a secondary antibody against rabbit IgG conjugated with HRP and TMB substrate. Experiments were repeated 2 times for confirmation.
Figure 11:
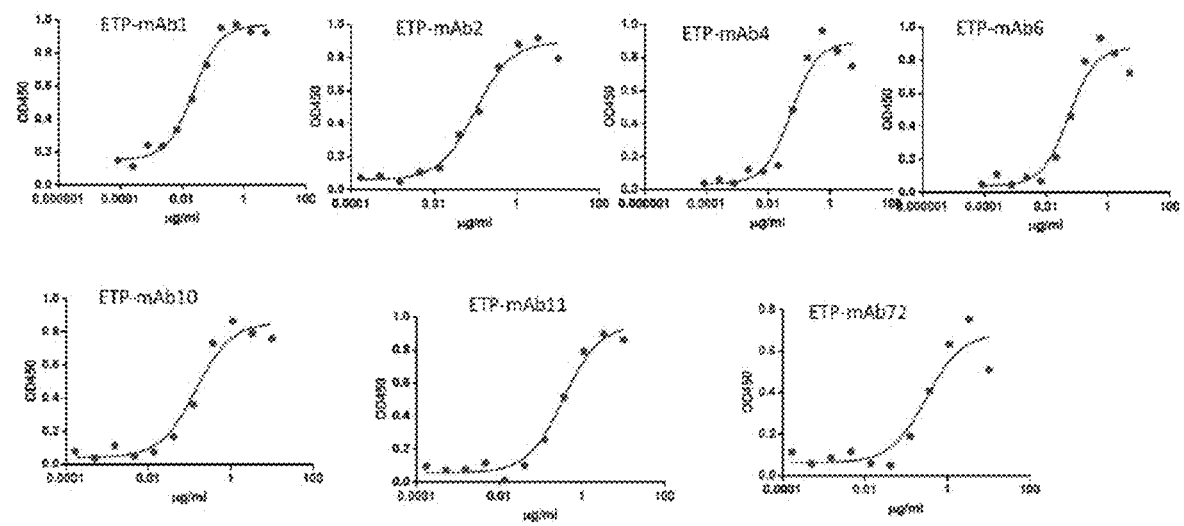
FIG. 11. Determination of binding affinities of endotrophin antibodies in ELISA. A series of antibody concentrations was assayed in ELISA and 4-parameter fitting was used to calculate binding affinity of the antibodies. Experiments have 3 repeats and error bars indicate standard deviation.

Binding of endotrophin by monoclonal antibodies was first screened by ELISA using supernatants collected from the B cell cultures (FIG. 10). ELISA titration was used to determine the binding affinity of a panel of monoclonal antibodies to endotrophin antigen (FIG. 11). Binding constants (EC50) of a panel of monoclonal antibodies were estimated using four-parameter curve fitting with Prism GraphPad (Table 3).

Figure 12A:
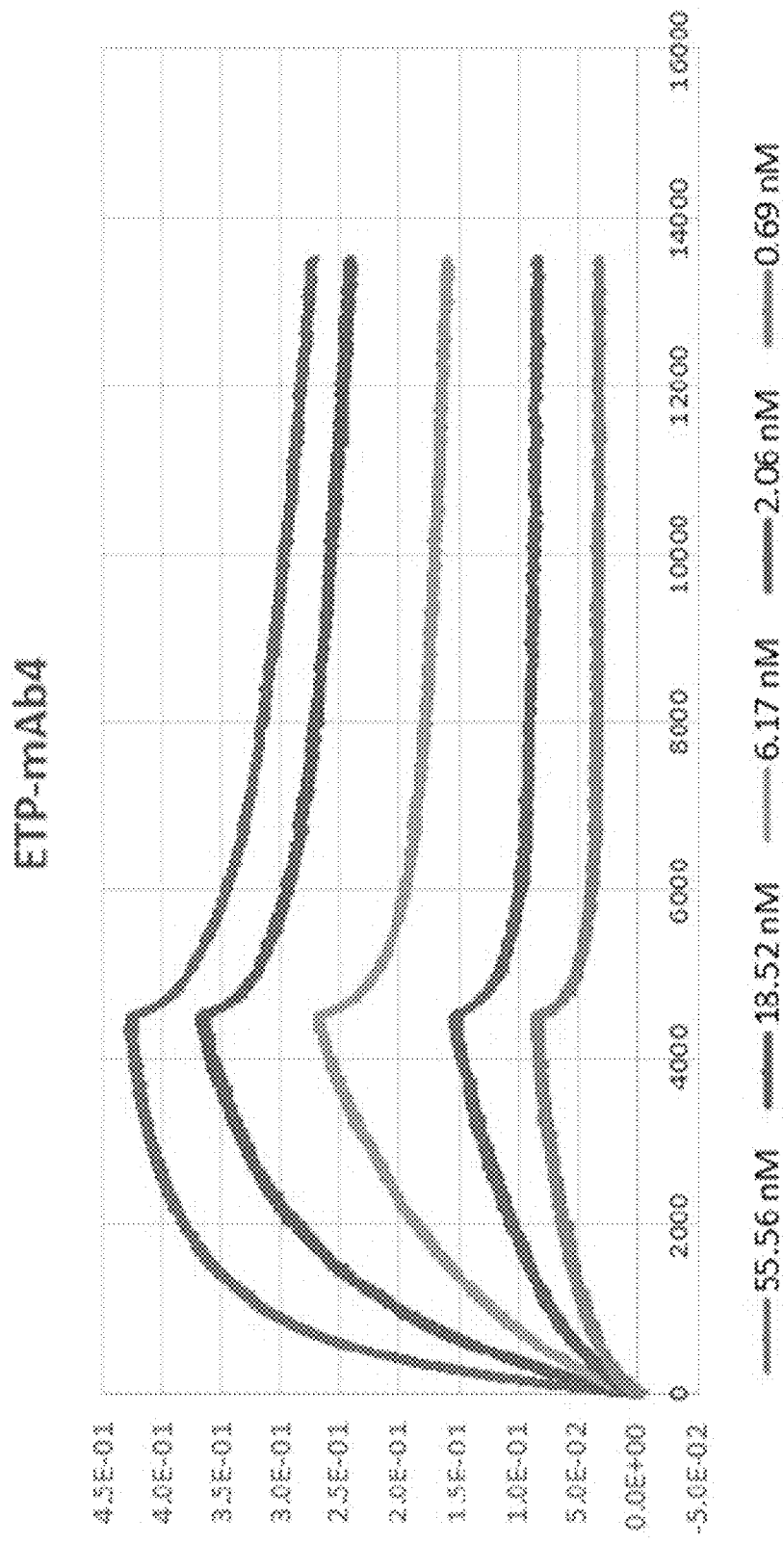
FIGS. 12A-B. Kinetic sensorgrams for ETP-mAb4 (FIG. 12A) and each of the humanized antibodies (FIG. 12B).
Figure 12B:
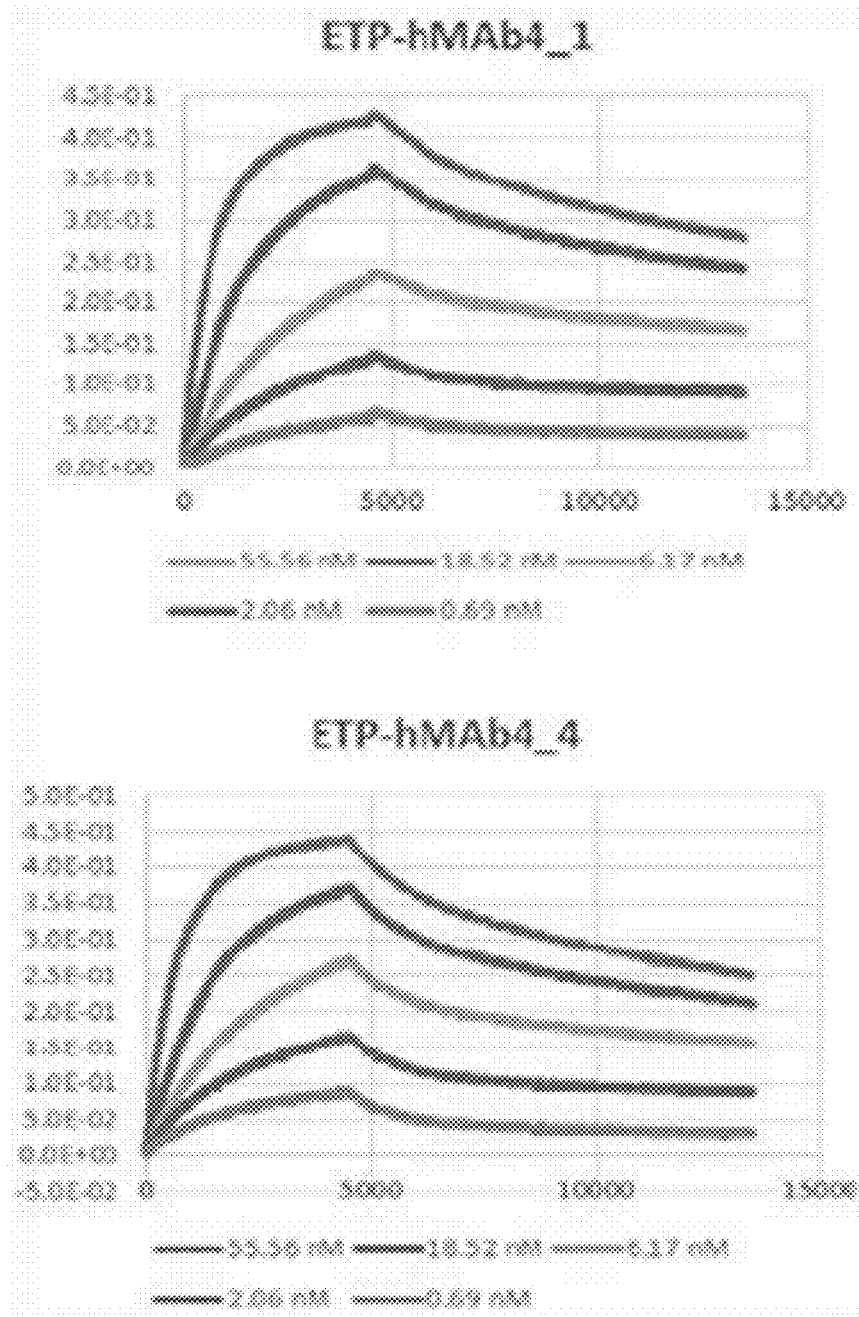

For antibody affinity measurement, antibody (30 µg/mL) was loaded onto the protein A biosensors for 4 min. Following a short baseline in kinetics buffer, the loaded biosensors were exposed to a series of recombinant endotrophin protein at 0.1-200 nM and background subtraction was used to correct for sensor drifting. All experiments were performed with shaking at 1,000 rpm. Background wavelength shifts were measured from reference biosensors that were loaded only with antibody. Kinetic sensorgrams for each antibody are shown in FIGS. 12A&B. ForteBio's data analysis software was used to fit the data to a 1:1 binding model to extract an association rate and dissociation rate. The Kd was calculated using the ratio of koff/kon and the estimated values of Kp for endotrophin ETP-mAb4 and 4 humanized ETP-hMab4 antibodies are listed in Table 4.

TABLE 1

CDRs of light chain variable sequences of ENDOTROPHIN antibodies

| Antibody Name | CDR1 (SEQ ID NO:) | CDR2 (SEQ ID NO:) | CDR3 (SEQ ID NO:) |
|---|---|---|---|
| ETP-mAb1 | QSIGSN (SEQ ID NO: 1) | DAS (SEQ ID NO: 2) | QQGYSDNYLDNA (SEQ ID NO: 3) |
| ETP-mAb2 | QSINSY (SEQ ID NO: 4) | QAS (SEQ ID NO: 5) | QSYDYRISGSDGNV (SEQ ID NO: 6) |

TABLE 1-continued

CDRs of light chain variable sequences of ENDOTROPHIN antibodies

| Antibody Name | CDR1 (SEQ ID NO:) | CDR2 (SEQ ID NO:) | CDR3 (SEQ ID NO:) |
|---|---|---|---|
| ETP-mAb4 | QSISSSY (SEQ ID NO: 7) | KAS (SEQ ID NO: 8) | QYSDWANSYGNA (SEQ ID NO: 9) |
| ETP-mAb6 | QNINSW (SEQ ID NO: 10) | QAS (SEQ ID NO: 11) | QSHDYRTTGSYGNV (SEQ ID NO: 12) |
| ETP-mAb10 | QNINSW (SEQ ID NO: 13) | QAS (SEQ ID NO: 14) | QSYDYRSSGNGGNV (SEQ ID NO: 15) |
| ETP-mAb11 | HRIKTY (SEQ ID NO: 16) | GAS (SEQ ID NO: 17) | QQGYSDGNVDNV (SEQ ID NO: 18) |
| ETP-mAb29 | QNIYSG (SEQ ID NO: 19) | GAS (SEQ ID NO: 20) | QTGYWTGSSDYIG (SEQ ID NO: 21) |
| ETP-mAb30 | KNAYLSYY (SEQ ID NO: 22) | WAS (SEQ ID NO: 23) | AAEYSNDSDNG (SEQ ID NO: 24) |
| ETP-mAb31 | KSVYNNNA (SEQ ID NO: 25) | SAS (SEQ ID NO: 26) | ACGYSIISDNG (SEQ ID NO: 27) |
| ETP-mAb32 | QSISSSY (SEQ ID NO: 28) | YAS (SEQ ID NO: 29) | QGGYSGYINS (SEQ ID NO: 30) |
| ETP-mAb47 | KSVYNNNA (SEQ ID NO: 31) | SAS (SEQ ID NO: 32) | AGGYSIISDNG (SEQ ID NO: 33) |
| ETP-mAb64 | QSVYSNNR (SEQ ID NO: 34) | YAA (SEQ ID NO: 35) | AGYKTADSDGIA (SEQ ID NO: 36) |
| ETP-mAb68 | KSVYNNNA (SEQ ID NO: 37) | SAS (SEQ ID NO: 38) | AGGYSIISDNG (SEQ ID NO: 39) |
| ETP-mAb70 | QSINSW (SEQ ID NO: 40) | EAS (SEQ ID NO: 41) | QQGYSYSNVDNNI (SEQ ID NO: 42) |
| ETP-mAb72 | ESISIY (SEQ ID NO: 43) | QAS (SEQ ID NO: 44) | QSHDYRIGRSDCNV (SEQ ID NO: 45) |

TABLE 2

CDRs of heavy chain variable sequences of ENDOTROPHIN antibodies

| Antibody Name | CDR1 (SEQ ID NO:) | CDR2 (SEQ ID NO:) | CDR3 (SEQ ID NO:) |
|---|---|---|---|
| ETP-mAb1 | GIDFSAGYY (SEQ ID NO: 46) | IYAGRSLNT (SEQ ID NO: 47) | ARDGASSGYYFKL (SEQ ID NO: 48) |
| ETP-mAb2 | GFSFSRSDY (SEQ ID NO: 49) | IDPGYSD (SEQ ID NO: 50) | ARDLGFDSNL (SEQ ID NO: 51) |
| ETP-mAb4 | GFSFSSGYY (SEQ ID NO: 52) | IYGGNNNP (SEQ ID NO: 53) | RKDINIGGAYEL (SEQ ID NO: 54) |
| ETP-mAb6 | GFSFSNSDY (SEQ ID NO: 55) | IDLVGNTNS (SEQ ID NO: 56) | ARDLGFDTNL (SEQ ID NO: 57) |
| ETP-mAb10 | GFSFSRGDY (SEQ ID NO: 58) | IDVGRDNDS SEQ ID NO: 59) | ARDLGFDTNL (SEQ ID NO: 60) |
| ETP-mAb11 | GFSFSSSYY (SEQ ID NO: 61) | IYLGNNENT (SEQ ID NO: 62) | ARDTSGGSDYYFGL (SEQ ID NO: 63) |
| ETP-mAb29 | GFSFSSRDY (SEQ ID NO: 64) | IDVGYTD (SEQ ID NO: 65) | ARDLGFDSNL (SEQ ID NO: 66) |
| ETP-mAb30 | GFSFSRSDY (SEQ ID NO: 67) | IDPGYSD (SEQ ID NO: 68) | ARDLGFDSNL (SEQ ID NO: 69) |

TABLE 2-continued

CDRs of heavy chain variable sequences of ENDOTROPHIN antibodies

| Antibody Name | CDR1 (SEQ ID NO:) | CDR2 (SEQ ID NO:) | CDR3 (SEQ ID NO:) |
|---|---|---|---|
| ETP-mAb31 | GFSFSRGDY (SEQ ID NO: 70) | IDAGSGSKG (SEQ ID NO: 71) | ARDLGFDTNL (SEQ ID NO: 72) |
| ETP-mAb32 | GFSFSRSDY (SEQ ID NO: 73) | IDPGYSD (SEQ ID NO: 74) | ARDLGFDSNL (SEQ ID NO: 75) |
| ETP-mAb47 | GFSFSDNYW (SEQ ID NO: 76) | IYTGSGS (SEQ ID NO: 77) | VRDLYGDIEHVPF (SEQ ID NO: 78) |
| ETP-mAb64 | GIDFSAGYY (SEQ ID NO: 79) | IYAGRSLNT (SEQ ID NO: 80) | ARDGASSGYYFKL (SEQ ID NO: 81) |
| ETP-mAb68 | GIDFSAGYY (SEQ ID NO: 82) | IYAGRSLNT (SEQ ID NO: 83) | ARDGASSGYYFK (SEQ ID NO: 84) |
| ETP-mAb70 | GFSFSRSDY (SEQ ID NO: 85) | IDPGYSD (SEQ ID NO: 86) | ARDLGFDSNL (SEQ ID NO: 87) |
| ETP-mAb72 | GFSFSRGDY (SEQ ID NO: 88) | IDVGSVIES (SEQ ID NO: 89) | ARDLGFDTN (SEQ ID NO: 90) |

TABLE 3

ENDOTROPHIN antibody binding affinities ($EC_{50}$) determined by ELISA titration

| Antibody name | EC50 (ng/ml) |
|---|---|
| ETP-mAb1 | 0.023 |
| ETP-mAb2 | 0.100 |
| ETP-mAb4 | 0.054 |
| ETP-mAb6 | 0.053 |
| ETP-mAb10 | 0.142 |
| ETP-mAb11 | 0.359 |
| ETP-mAb72 | 0.306 |

TABLE 4

Estimated kinetic binding constant ($K_D$) of ETP-mAb4 and four humanized antibodies (ETP-hMab4) determined using Octet (96-Red) instrument

| Antibody | $K_D$ (M) | $k_{on}$ (1/Ms) | $k_{dis}$ (1/s) | Full $X^2$ | Full $R^2$ |
|---|---|---|---|---|---|
| ETP-mAb4   | 1.75 E−09 | 1.42 E+05 | 2.49 E−04 | 0.5983 | 0.9437 |
| ETP-mAb4.1 | 2.03 E−09 | 1.16 E+05 | 2.35 E−04 | 0.1393 | 0.9873 |
| ETP-mAb4.2 | 2.48 E−09 | 1.23 E+05 | 3.05 E−04 | 0.4300 | 0.9669 |
| ETP-mAb4.4 | 2.53 E−09 | 1.30 E+05 | 3.28 E−04 | 0.3658 | 0.9745 |
| ETP-mAb4.5 | 1.92 E−09 | 1.16 E+05 | 2.23 E−04 | 0.2221 | 0.9787 |

TABLE 5

Nucleotide sequences for antibody variable regions

| Antibody Name | Chain | Variable Sequence (5' to 3') | SEQ ID NO: |
|---|---|---|---|
| ETP-mAb1 | Heavy | CAGTCGGTGAAGGAGTCCGGGGGAGACCTGGTCAAGCCTGGGGCTTCCCTGACACTCACCTGCACAGCCTCTGGAATCGACTTCAGTGCCGGCTACTACATGTGCTGGGTCCGCCAGGCTCCAGGGAAGGGGCTGGAGTTGATCGCATGCATTTATGCTGGTCGTAGTCTTAACACTTTCTACGCGAGCTGGGCGAAAGGCCGATTCACCATCTCCAGAGCCTCGTCGACCACGGTGACTCTGGCGATGACCAGTCTGACAGCCGCGGACACGGCCACCTATTTCTGTGCGAGAGATGGGGCTAGCAGTGGCTACTACTTTAAGTIGTGGGGCCCAGGCACCCTGGTCACCATCTCTTCA | 91 |
| | Light | GAGCTCGATATGACCCAGACTCCAGCCTCTGTGGAGGTAGCTGTGGGAGGCACAGTCACCATCAAGTGCCAGGCCAGTCAGAGCATTGGTAGTAATTTAGCCTGGTATCAGCAGAAACCAGGGCAGCGTCCCAATGTCCTGATCTACGATGCATCGAATCTGGCATCTGGGGTCTCATCGCGGTTCAAAGGCAGTGGATCTGGGACACAGTTCACTCTCACCATCAGCGGCGGGAGTGTGCCGATGCTGCCACTTACTACTGTCAACAGGGTTATAGTGATAATTATCTTGATAATGCTTTCGGCGGAGGGACCGAGGTGGTGGTCAAA | 92 |
| ETP-mAb2 | Heavy | GAGCAGTCGTTGGAGGAGTCCGAGGGAGGCCTGGTCCAGCCTGAGGGATCCCTGACACTCACCTGCACAGCTTCTGGATTCTCCTTCAGTAGAAGCGACTACATGTGTTGGGTCCGCCAGGCTCCAGGGAAGGGACTGGAGTGGATCGGATGGATTGATCCTGGTTATAGTGACACTTACTACGCGAGCTGGGCGAAGGCCGAACCACCATCTCCAAAGCCTCGTCGACCACGGTGACTCTGCAGATGACCAGTCTGACAGTCGCGGACACGGCCACCTATTTCTGTGCGAGAGATTTGGGGTTTGATAGTAATTTGTGGGGCCCAGGCACCCTGGTCACCATCTCCTCA | 93 |

TABLE 5-continued

Nucleotide sequences for antibody variable regions

| Antibody Name | Chain | Variable Sequence (5' to 3') | SEQ ID NO: |
|---|---|---|---|
| | Light | GAGCTCGATCTGACCCAGACTCCAGCCTCCGTGTCTGAACCTG<br>TGGGAGGCACAGTCACCATCAAGTGCCAGGCCAGTCAGAGTAT<br>TAATAGTTACTTATCCTGGTATCAGCAGAAACCAGGGCAGCCT<br>CCCAAGCTCCTGATTTACCAGGCATCGAAACTGGCATCTGGGG<br>TCCCATCGCGGTTCAAAGGCAGTGGATCTGGGACACAGTTCAC<br>TCTCACCATCAGCGACCTGGAGTGTGCCGATGCTGCCACTTAC<br>TACTGTCAAAGCTATGATTATCGTATTAGTGGTAGCGATGGTA<br>ATGTTTTCGGCGGAGGGACCAATGTGGAAATCAAA | 94 |
| ETP-mAb4 | Heavy | AGCAGTCGGGTGAAGGAGTCCGGGGGAGACCTGGTCAAGCCTG<br>GGGCATCCCTGACACTCACCTGCAAAGCCTCTGGATTCTCCTT<br>CAGTAGCGGCTACTACATATGTTGGGTCCGCCAGGCTCCAGGG<br>AAGGGGCTGGAGTGGATCGCGTGCATTTATGGTGGTAATAATA<br>ACCCATATTACGCGAACTGGGTGAATGGTCGATTCACCACCTC<br>CAAAACCTCGTCGACCACGGTGACTCTGCAAATGACCAATCTG<br>ACAGGCGCGGACACGGCCACCTATTTCTGTGCGAGAAAAGATA<br>TTAATATTGGTGGTGCTTATGAGTTGTGGGGCCCAGGCACCCT<br>GGTCACCATCTCCTCA | 95 |
| | Light | GAGCTCGTGATGACCCAGACTCCAGCCTCCGTGTCTGAACCTG<br>TGGGAGGCACAGTCACCATCAACTGCCAGGCCAGTCAGAGTAT<br>TAGTAGTAGCTACTTATCCTGGTATCAGCAGAAACCAGGGCAG<br>CCTCCCAAGCTCCTGATTTACAAGGCATCCACTCTGGCATCTG<br>GGGTCCCATCGCGGTTCAAAGGCAGTGGATCTGGGACACAGTT<br>CAGTCTCACCATCAGCGACCTGGAGTGTGCCGATGCTGCCACT<br>TACTATTGTCAATATAGTGATTGGGCTAATAGTTATGGGAATG<br>CTTTCGGCGGGGGGACCGAGGTGGTGGTCAAA | 96 |
| ETP-mAb6 | Heavy | CAGTCGGTGAAGGAGTCCGAGGGAGGCCTGGTCCAGCCTGAGG<br>GATCCCTGACACTCACCTGCACAGCTTCTGGATTCTCCTTCAG<br>TAACAGCGACTACATGTGCTGGGTCCGCCAGGCTCCAGGGAAG<br>GGACTGGAGTGGATCGGATGGATAGATCTTGTTGGTAATACTA<br>ATTCTTACTACGCGAGTTGGGCGAAAGGCCGATTCACCATCTC<br>CAAAACCTCGTCGACCACGGTGGCTCTGCAAATGACCAGTCTG<br>ACAGTCGCGGACACGGCCACCTATTTCTGTGCGAGAGATTTGG<br>GTTTTGATACTAATTTGTGGGGCCCAGGCACCCTGGTCACCGT<br>CTCCTCA | 97 |
| | Light | GAGCTCGATCTGACCCAGACTCCAGCCTCCGTGTCTGCAGCTG<br>TGGGAGGCACAGTCACCATCAATTGCCAGGCCAGTCAGAACAT<br>TAATAGTTGGTTATCCTGGTATCAGCAGAAACCAGGGCAGCGT<br>CCCAAGCTCCTGATTTACCAGGCATCGAAACTGCCATCTGGGG<br>TCCCATCGCGGTTCAAGGGCAGTGGATCTGGGACACAGTTCAC<br>TCTCACCATCAGCGACCTGGAGTGTGCCGATGCTGCCACTTAC<br>TACTGTCAAAGCCATGATTATCGTACTACTGGTAGTTATGGTA<br>ATGTTTTCGGCGGAGGGACTGAGGTGGAAATCAAA | 98 |
| ETP-mAb10 | Heavy | CAGTCGTTGGAGGAGTCCGGGGGAGGCCTGGTCCAGCCTGAGG<br>GATCCCTGACACTCACCTGCACAGCTTCTGGATTCTCCTTCAG<br>TAGGGGCGACTACATGTGCTGGGTCCGCCAGGCTCCAGGGAAG<br>GGACTGGAGTGGATCGGATGGATAGATGTTGGTCGTGATAATG<br>ATTCTTACTACGCGACTTGGGCGAAAGGCCGATTCAGCATCTC<br>CAAAACCTCGTCGACTACGGTGACTCTGCAAATGACCAGTCTG<br>ACAGTCGCGGACACGGCCACCTATTTCTGTGCGAGAGATTTGG<br>GTTTTGATACTAATTTGTGGGGCCCAGGCACCCTGGTCACCGT<br>CTCTTCA | 99 |
| | Light | GAGCTCGATATGACCCAGACTCCAGCCTCGGTGTCTGCAGCTG<br>TGGGAGGCACAGTCACCATCAACTGCCAGGCCAGTCAGAACAT<br>TAATAGTTGGTTATCCTGGTATCAGCAGAAACCAGGGCAGCCT<br>CCCAAGCTCCTGATTTATCAGGCATCGAAACTGGCATCTGGGG<br>TCCCATCGCGGTTGAAAGGCAGTGGATCTGGGACACAGTTCAG<br>TCTCACCATCAGCGACCTGGAGTGTGCCGATGTGCCACTTAC<br>TACTGTCAAAGCTATGATTATCGTAGTAGTGGTAACGGTGGTA<br>ATGTTTTCGGCGGAGGGACCGAGGTGGAAATCAAA | 100 |
| ETP-mAb11 | Heavy | CAGTCGGTGAAGGAGTCCGAGGGAGGCCTGGTCCAGCCTGAGG<br>GATCCCTGACACTCACCTGCACAGCTTCTGGATTCTCCTTCAG<br>TAGCAGCTACATGTGCTGGGTCCGCCAGGCTCCAGGGAAG<br>GGGCTGGAGTGGATCGGATGCATTTATCTTGGTAATAACGAAA<br>ATACTGCCTACACGAGCTGGGCGAAAGGCCGATTCACCATCTC<br>CAAAACCTCGTCGACCACGGTGACTCTGCAAATGACCAGTCTG<br>ACAGCCGCGGACACGGACCACCTATTTCTGTGCGAGAGATACTA<br>GTGGTGGTAGTGATTATTATTTTGGCTTGTGGGGCCCAGGCAC<br>CCTGGTCACCATCTCCTCA | 101 |
| | Light | GAGCTCGATCTGACCCAGACTCCAGCCTCTGTGGAGGTAGCTG<br>TGGGAGGCACAGTCACCATCAAGTGCCAGGCCAGTCATCGCAT<br>TAAAACCTACTTAGCCTGGTATCAGCAGAAACCAGGGCAGCCT | 102 |

TABLE 5-continued

Nucleotide sequences for antibody variable regions

| Antibody Name | Chain | Variable Sequence (5' to 3') | SEQ ID NO: |
|---|---|---|---|
| | | CCCAAGCTCCTGATCTATGGTGCATCCACTCTGGCATCTGGGG TCCCATCGCGGTTCAAAGGCAGTGGATCTGGGACACAGTTTAC TCTCACCATCAGCGGCGTGGAGTGTGCCGATGCTGCCACTTAT TATTGTCAACAGGGTTATAGTGACGGGAACGTTGATAATGTTT TCGGCGGAGGGACCGAGGTGGAAATCAAA | |
| ETP-mAb29 | Heavy | GAGCAGTCGGTGGAGGAGTCCGGGGGAGGCCTGGTCCAGCCTG AGGGATCCCTGACACTCACCTGCACAGCTTCTGGATTCTCCTT CAGTAGCAGGGACTACATGTGTTGGGTCCGCCAGGCTCCAGGG AAGGGACTGGAGTGGATCGGATGGATTGATGTTGGTTATACTG ACGCTTACTACGCGAGCTGGGCGAAAGGCCGATTCACCATCTC CAGAACCTCGTCGACCACGGTGACTCTGCAAATGACCAGTCTG ACAGTCGCGGACACGGCCACCTATTTCTGTGCGAGAGATTTGG GTTTTGATAGTAATTTGTGGGGCCCAGGCACCCTGGTCACCAT CTCTTCA | 103 |
| | Light | GAGCTCGTGCTGACCCAGACACCAGCCTCCGTGTCTGCAGCTG TGGGAGGCACAGTCAGCATCAATTGCCAGTCCAGTCAAAACAT TTATAGTGGTTTGGCCTGGTATCAGCAGAAACCAGGGCAGCCT CCCAAGCTCCTGATCTATGGTGCATCCACTCTGGCATCTGGGG TCTCATCGCGGTTCAAAGGCAGTGGATCTGGGACAGAGTTCAC TCTCACCATCAGCGACCTGGAGTGTGCCGATGCTGCCACTTAC TACTGTCAAACCGGTTATTGGACTGGTAGTAGTGATTATATTG GTTTTGGCGGAGGGACCAATGTGGAAATCAAA | 104 |
| ETP-mAb30 | Heavy | GAGCAGTCGGTGAAGGGGTCCGAGGGAGGCCTGGTCCAGCCTG AGGGATCCCTGACACTCACCTGCACAGCTTCTGGATTCTCCTT CAGTAGAAGCGACTACATGTGTTGGGTCCGCCAGGCTCCAGGG AAGGGACTGGAGTGGATCGGATGGATTGATCCTGGTTATAGTG ACACTTACTACGCGAGCTGGGCGCAAGGCCGAACCACCATCTC CAAAGCCTCGTCGACCACGGTGACTCTGCAGATGACCAGTCTG ACAGTCGCGGACACGGCCACCTATTTCTGTGCGAGAGATTTGG GGTTTGATAGTAATTTGTGGGGCCCAGGCACCCTGGTCACCGT CTCTTCA | 105 |
| | Light | ACCCAGACACCAGCCTCCGTGTCTGCAGCTGTGGGAGGCACAG TCAGCATCAATTGCCAGTCCAGTCAGAGTGTTTATAAGAACGC CTATTTATCCTACTACTTAGCCTGGTATCAGCAGAAACCAGGG CAGCCTCCCAAGCTCCTGATCTACTGGGCTTCCACTCTGGCAT CTGGGGTCCCATCGCGGTTCAAAGGCAGTGGATCTGGGACACA GTTCACTCTCACCATCAGCGACGTGCAGTGTGACGATGCTGCC ACTTACTACTGTGCAGCCGAATATAGTAATGATAGTGATAATG GTTTCGGCGGAGGGACCAATGTGGAAATCAAA | 106 |
| ETP-mAb31 | Heavy | CAGTCGTTGGAGGAGTCCGGGGGAGGCCTGGTCAAGCCTGGAG GAACCCCGACACTCACCTGCACAGCCTCTGGATTCTCCTTCAG CCGTGGCGACTACATGTGCTGGGTCCGCCAGGCTCCAGGGAAG GGACTGGAGTGGATCGGATGGATTGATGCTGGTAGTGGTAGTA AAGGTTACTACGCGAGGTGGGCGAAAGGCCGATTCACCATCTC CAAAACCTCGTCCACCACGGTGACTTTACAAATGACTAGTGTG ACAGTCGCGGACACGGCCACTTATTTCTGTGCGAGAGATTTGG GTTTTGATACTAATTTGTGGGGCCCAGGCACCCTGGTCACCAT CTCTTCA | 107 |
| | Light | GAGCTCGTGATGACCCAGACTCCATCTCCCGTGTCTGCAGCTG TGGGAGGCACAGTCAGCATCAGTTGCCAGGCCAGTAAGAGTGT TTATAATAACAATGCCTTATCCTGGTATCAGCAGAAACCAGGG CAGCCTCCCAAACTCCTGATCTATTCTGCATCCACTCTGGCAT CTGGGGTCCCATCGCGGTTCAGCGGCAGTGGTTCTGGGACAGA GTTCACTCTCACCATCAGCGGCGTGCAGTGTGACGATGCTGCC ACTTACTATTGTGCATGCGGTTATAGTATTATTAGTGATAATG GTTTCGGCGGAGGGACCAATGTGGAAATCAAA | 108 |
| ETP-mAb32 | Heavy | GAGCAGTCGGTGGAGGAGTCCGGGGGAGGCCTGGTCCAGCCTG AGGGATCCCTGACACTCACCTGCACAGCTTCTGGATTCTCCTT CAGTAGAAGCGACTACATGTGTTGGGTCCGCCAGGCTCCAGGG AAGGGACTGGAGTGGATCGGATGGATTGATCCTGGTTATAGTG ACACTTACTACGCGAGCTGGGCGCAAGGCCGAACCACCATCTC CAAAGCCTCGTCGACCACGGTGACTCTGCAGATGACCAGTCTG ACAGTCGCGGACACGGCCACCTATTTCTGTGCGAGAGATTTGG GTTTGATAGTAATTTGTGGGGCCCAGGCACCCTGGTCACCGT CTCTTCA | 109 |
| | Light | GAGCTCGATATGACCCAGACTCCAGCCTCCGTGTCTGAACCTG TGGGAGGCACAGTCACCATCAACTGCCAGGCCAGTCAGAGTAT TAGTAGTAGCTACTTATCCTGGTATCAGCAGAAACCAGGGCAG CCTCCCAAGCTCCTGATCTATTATGCATCCACTCTGGCATCTG GGTCTCATCGCGGTTCAAAGGCAGTGGATCTGGGACACAGTT CACTCTCACCATCAGCGACCTGGAGTGTGACGATGCTGCCACT | 110 |

TABLE 5-continued

Nucleotide sequences for antibody variable regions

| Antibody Name | Chain | Variable Sequence (5' to 3') | SEQ ID NO: |
|---|---|---|---|
| | | TACTACTGTCAGGGCGGTTATAGTGGATATATCAATTCTTTCG GCGGAGGGACCGAGGTGGTCGTCAAA | |
| ETP-mAb47 | Heavy | GAGCAGTCGGTGGAGGAGTCCGGGGGAGGCCTGGTCAAGCCTG GGGCATCCCTGACACTCACCTGCAAAGCCTCTGGATTCTCCTT CAGTGACAACTACTGGATATACTGGGTCCGCCAGGCTCCAGGG AAGGGGCTGGAGTGGATCGGATATATTTATACTGGTAGTGGTA GCACTTACTACGCGAGCTGGGCGAAAGGCCGAAGCACCATCTC CAAAACCTCGTCGACCACGGTGACTCTACAAATGACCAGTCTG ACAGCCGCGGACACGGCCACCTATTTCTGTGTGAGAGATCTTT ATGGTGATATTGAGCATGTGCCCTTCTGGGGCCCAGGCACCCT GGTCACCGTCTCTTCA | 111 |
| | Light | GAGCTCGTGATGACCCAGACTCCATCTCCCGTGTCTGCAGCTG TGGGAGGCACAGTCAGCATCAGTTGCCAGGCCAGTAAGAGTGT TTATAATAACAATGCCTTATCCTGGTATCAGCAGAAACCAGGG CAGCCTCCCAAACTCCTGATCTATTCTGCATCCACTCTGGCAT CTGGGGTCCCATCGCGGTTCAGCGGCAGTGGTTCTGGGACAGA GTTCACTCTCACCATCAGCGGCGTGCAGTGTGACGATGCTGCC ACTTACTATTGTGCAGGCGGTTATAGTATTATTAGTGATAATG GTTTCGGCGAAGGGACCGAGCTGGAAATCAAA | 112 |
| ETP-mAb64 | Heavy | CAGTCGGTGGAGGAGTCCGGGGGAGACCTGGTCAAGCCTGGGG CTTCCCTGACACTCACCTGCACAGCCTCTGGAATCGACTTCAG TGCCGGCTACTACATGTGCTGGGTCCGCCAGGCTCCAGGGAAG GGGCTGGAGTTGATCGCATGCATTTATGCTGGTCGTAGTCTTA ACACTTTCTACGCGAGCTGGGCGAAAGGCCGATTCACCATCTC CAGAGCCTCGTCGACCACGGTGACTCTGGCGATGACCAGTCTG ACAGCCGCGGACACGGCCACCTATTTCTGTGCGAGAGATGGGG CTAGCAGTGGCTACTACTTTAAGTIGTGGGGCCCAGGCACCCT GGTCACCATCTCCTCA | 113 |
| | Light | GAGCTCGTGATGACCCAGACTCCATCCCCGTGTCTGCAGCTG TGGGAGGCACAGTCACCATCAACTGCCAGTCCAGTCAGAGTGT TTATAGTAACAACCGCTTAGCCTGGTATCAGCAGAAACCAGGG CAGCCTCCCAAGCTCCTGGTCTATTATGCAGCCACTCTGGCAT CTGGGGTCCCGTCGCGGTTCAAAGGCAGTGGATATGGGACACA GTCCACTCTCACCATCGCCGATGTGGTGTGTGACGATGCTGCC ACTTACTACTGTGCAGGATATAAAACTGCTGATTCTGATGGTA TTGCTTTCGGCGGAGGGACCGAGGTGGTGGTCAAA | 114 |
| ETP-mAb68 | Heavy | CAGTCGGTGAAGGAGTCCGAGGGAGACCTGGTCAAGCCTGGGG CTTCCCTGACACTCACCTGCACAGCCTCTGGAATCGACTTCAG TGCCGGCTACTACATGTGCTGGGTCCGCCAGGCTCCAGGGAAG GGGCTGGAGTTGATCGCATGCATTTATGCTGGTCGTAGTCTTA ACACTTTCTACGCGAGCTGGGCGAAAGGCCGATTCACCATCTC CAGAGCCTCGTCGACCACGGTGACTCTGGCGATGACCAGTCTG ACAGCCGCGGACACGGCCACCTATTTCTGTGCGAGAGATGGGG CTAGCAGTGGCTACTACTTTAAGTTGTGGGGCCCAGGCACCCT GGTCACCGTCTCTTCA | 115 |
| | Light | GAGCTCGTGATGACCCAGACTCCATCTCCCGTGTCTGCAGCTG TGGGAGGCACAGTCAGCATCAGTTGCCAGGCCAGTAAGAGTGT TTATAATAACAATGCCTTATCCTGGTACCAGCAGAAACCAGGG CAGCCTCCCAAACTCCTGATCTATTCTGCATCCACTCTGGCAT CTGGGGTCCCATCGCGGTTCAGCGGCAGTGGTTCTGGGACAGA GTTCACTCTCACCATCAGCGGCGTGCAGTGTGACGATGCTGCC ACTTACTATTGTGCAGGCGGTTATAGTATTATTAGTGATAATG GTTTCGGCGGAGGGACCGAGGTGGTGGTCAAA | 116 |
| ETP-mAb70 | Heavy | CGAGCAGTCGGGAAGGAGTCCGAGGGAGGCCTGGTCCAGCCTG AGGGATCCCTGACACTCACCTGCACAGCTTCTGGATTCTCCTT CAGTAGAAGCGACTACATGTGTTGGGTCCGCCAGGCTCCAGGG AAGGGACTGGAGTGGATCGGATGGATTGATCCTGGTTATAGTG ACACTTACTACGCGAGCTGGGCGCAAGGCCGAACCACCATCTC CAAAGCCTCGTCGACCACGGTGACTCTGCAGATGACCAGTCTG ACAGTCGCGGACACGGCCACCTATTTCTGTGCGAGAGATTTGG GGTTTGATAGTAATTTGTGGGGCCCAGGCACCCTGGTCACCAT CTCCTCA | 117 |
| | Light | GAGCTCGATCTGACCCAGACTCCAGCCTCCGTGGAGGCAGCTG TGGGAGGCACAGTCACCATCAATTGCCAGGCCAGTCAGAGCAT TAATAGTTGGTTATCCTGGTATCAGCAGAAACCAGGGCAGCGT CCCAAACTCCTGATCTACGAAGCATCCACTCTGGCATCTGGGG TCTCATCGCGGTTCAGTGGCAGTGGATCTGGGACACAGTTCAC TCTCACCATCAGCGGCGTGCAGTGTGACGATGCTGCCACTTAC TACTGTCAACAGGGTTATAGTTATAGTAATGTTGATAATAATA TTTTCGGCGGAGGGACCGAGGTGGTGGTCAAA | 118 |

TABLE 5-continued

Nucleotide sequences for antibody variable regions

| Antibody Name | Chain | Variable Sequence (5' to 3') | SEQ ID NO: |
|---|---|---|---|
| ETP-mAb72 | Heavy | CAGTCGCTGGAGGAGTCCGGGGGAGGCCTGGTCCAGCCTGAGG GATCCCTGACACTCACCTGCACAGCTTCTGGATTCTCCTTCAG TCGTGGCGACTACGTGTGCTGGGTCCGCCAGGCTCCAGGGAAG GGACTGGAGTGGATCGGATGGATTGATGTTGGTAGTGTTATTG AAAGTTACTACGCGACCTGGGCGAAAGGCCGATTCACCATCTC CAAAACCTCGTCGACCACGGTGACTCTGCAAATGACTAGTCTG ACAGTCGCGGACACGGCCACTTATTTCTGTGCGAGAGATTTGG GTTTTGATACTAATTTGTGGGGCCCAGGCACCCTGGTCACCGT CTCCTCA | 119 |
| | Light | GAGCTCGTGATGACCCAGACTCCAGCCTCCGTGGAGGCAGCTG TGGGAGGCACAGTCACCATCAATTGCCAGGCCAGTGAGAGCAT TAGTATCTATTTAAACTGGTATCAGCAGAAACCAGGGCAGCCT CCCAAGCTCCTGATTTATCAGGCATCGAAACTGGCATCTGGGG TCCCATCGCGGTTCAAAGGCAGTGGATCTGGGACAGAGTTCAC TCTCACCATCAGCGACCTGGAGTGTGCCGATGCTGCCACTTAC TACTGTCAAAGCCATGATTATCGTATTGGTCGTAGTGATTGTA ATGTTTTCGGCGGAGGGACCAATGTGGAAATCAAA | 120 |

TABLE 6

Protein sequences for antibody variable regions

| Antibody Name | Chain | Variable Sequence | SEQ ID NO: |
|---|---|---|---|
| ETP-mAb1 | Heavy | QSVKESGGDLVKPGASLTLTCTASGIDESAGYYMCWVRQAPGK GLELIACIYAGRSLNTFYASWAKGRFTISRASSTTVTLAMTSL TAADTATYFCARDGASSGYYFKLWGPGTLVTISS | 121 |
| | Light | ELDMTQTPASVEVAVGGTVTIKCQASQSIGSNLAWYQQKPGQR PNVLIYDASNLASGVSSRFKGSGSGTQFTLTISGGECADAATY YCQQGYSDNYLDNAFGGGTEVVVK | 122 |
| ETP-mAb2 | Heavy | EQSLEESGGGLVQPEGSLTLTCTASGFSFSRSDYMCWVRQAPG KGLEWIGWIDPGYSDTYYASWAQGRTTISKASSTTVTLQMTSL TVADTATYFCARDLGFDSNLWGPGTLVTISS | 123 |
| | Light | ELDLTQTPASVSEPVGGTVTIKCQASQSINSYLSWYQQKPGQP PKLLIYQASKLASGVPSRFKGSGSGTQFTLTISDLECADAATY YCQSYDYRISGSDGNVFGGGTNVEIK | 124 |
| ETP-mAb4 | Heavy | SSRVKESGGDLVKPGASLTLTCKASGFSFSSGYYICWVRQAPG KGLEWIACIYGGNNNPYYANWVNGRFTTSKTSSTTVTLQMTNL TGADTATYFCARKDINIGGAYELWGPGTLVTISS | 125 |
| | Light | ELVMTQTPASVSEPVGGTVTINCQASQSISSSYLSWYQQKPGQ PPKLLIYKASTLASGVPSRFKGSGSGTQFSLTISDLECADAAT YYCQYSDWANSYGNAFGGGTEVVVK | 126 |
| ETP-mAb6 | Heavy | QSVKESEGGLVQPEGSLTLTCTASGFSFSNSDYMCWVRQAPGK GLEWIGWIDLVGNTNSYYASWAKGRFTISKTSSTTVALQMTSL TVADTATYFCARDLGFDTNLWGPGTLVTVSS | 127 |
| | Light | ELDTQTPASVSAAVGGTVTINCQASQNINSWLSWYQQKPGQR PKLLIYQASKLPSGVPSRFKGSGSGTQFTLTISDLECADAATY YCQSHDYRTTGSYGNVEGGGTEVEIK | 128 |
| ETP-mAb10 | Heavy | QSLEESGGGLVQPEGSLTLTCTASGFSFSRGDYMCWVRQAPGK GLEWIGWIDVGRDNDSYYATWAKGRESISKTSSTTVTLQMTSL TVADTATYFCARDLGFDTNLWGPGTLVTVSS | 129 |
| | Light | ELDMTQTPASVSAAVGGTVTINCQASQNINSWLSWYQQKPGQP PKLLIYQASKLASGVPSRLKGSGSGTQFSLTISDLECADGATY YCQSYDYRSSGNGGNVEGGGTEVEIK | 130 |
| ETP-mAb11 | Heavy | QSVKESEGGLVQPEGSLTLTCTASGFSFSSSYYMCWVRQAPGK GLEWIGCIYLGNNENTAYTSWAKGRFTISKTSSTTVTLQMTSL TAADTTTYFCARDTSGGSDYYFGLWGPGTLVTISS | 131 |
| | Light | ELDLTQTPASVEVAVGGTVTIKCQASHRIKTYLAWYQQKPGQP PKLLIYGASTLASGVPSRFKGSGSGTQFTLTISGVECADAATY YCQQGYSDGNVDNVEGGGTEVEIK | 132 |

TABLE 6-continued

Protein sequences for antibody variable regions

| Antibody Name | Chain | Variable Sequence | SEQ ID NO: |
|---|---|---|---|
| ETP-mAb29 | Heavy | EQSVEESGGGLVQPEGSLTLTCTASGFSFSSRDYMCWVRQAPG KGLEWIGWIDVGYTDAYYASWAKGRFTISRTSSTTVTLQMTSL TVADTATYFCARDLGFDSNLWGPGTLVTISS | 133 |
| | Light | ELVLTQTPASVSAAVGGTVSINCQSSQNIYSGLAWYQQKPGQP PKLLIYGASTLASGVSSRFKGSGSGTEFTLTISDLECADAATY YCQTGYWTGSSDYIGFGGGTNVEIK | 134 |
| ETP-mAb30 | Heavy | EQSVKGSEGGGLVQPEGSLTLTCTASGFSFSRSDYMCWVRQAPG KGLEWIGWIDPGYSDTYYASWAQGRTTISKASSTTVTLQMTSL TVADTATYFCARDLGFDSNLWGPGTLVTVSS | 135 |
| | Light | TQTPASVSAAVGGTVSINCQSSQSVYKNAYLSYYLAWYQQKPG QPPKLLIYWASTLASGVPSRFKGSGSGTQFTLTISDVQCDDAA TYYCAAEYSNDSDNGFGGGTNVEIK | 136 |
| ETP-mAb31 | Heavy | QSLEESGGGLVKPGGTPTLTCTASGFSFSRGDYMCWVRQAPGK GLEWIGWIDAGSGSKGYYARWAKGRFTISKTSSTTVTLQMTSV TVADTATYFCARDLGFDTNLWGPGTLVTISS | 137 |
| | Light | ELVMTQTPSPVSAAVGGTVSISCQASKSVYNNNALSWYQQKPG QPPKLLIYSASTLASGVPSRFSGSGSGTEFTLTISGVQCDDAA TYYCACGYSIISDNGFGGGTNVEIK | 138 |
| ETP-mAb32 | Heavy | EQSVEESGGGLVQPEGSLTLTCTASGFSFSRSDYMCWVRQAPG KGLEWIGWIDPGYSDTYYASWAQGRTTISKASSTTVTLQMTSL TVADTATYFCARDLGFDSNLWGPGTLVTVSS | 139 |
| | Light | ELDMTQTPASVSEPVGGTVTINCQASQSISSSYLSWYQQKPGQ PPKLLIYYASTLASGVSSRFKGSGSGTQFTLTISDLECDDAAT YYCQGGYSGYINSFGGGTEVVVK | 140 |
| ETP-mAb47 | Heavy | EQSVEESGGGLVKPGASLTLTCKASGFSFSDNYWIYWVRQAPG KGLEWIGYIYTGSGSTYYASWAKGRSTISKTSSTTVTLQMTSI TAADTATYFCVRDLYGDIEHVPFWGPGTLVTVSS | 141 |
| | Light | ELVMTQTPSPVSAAVGGTVSISCQASKSVYNNNALSWYQQKPG QPPKLLIYSASTLASGVPSRFSGSGSGTEFTLTISGVQCDDAA TYYCAGGYSIISDNGFGEGTELEIK | 142 |
| ETP-mAb64 | Heavy | QSVEESGGDLVKPGASLTLTCTASGIDESAGYYMCWVRQAPGK GLELIACIYAGRSLNTFYASWAKGRFTISRASSTTVTLAMTSL TAADTATYFCARDGASSGYYFKLWGPGTLVTISS | 143 |
| | Light | ELVMTQTPSPVSAAVGGTVTINCQSSQSVYSNNRLAWYQQKPG QPPKLLVYYAATLASGVPSRFKGSGYGTQSTLTIADVVCDDAA TYYCAGYKTADSDGIAFGGGTEVVVK | 144 |
| ETP-mAb68 | Heavy | QSVKESEGDLVKPGASLTLTCTASGIDESAGYYMCWVRQAPGK GLELIACIYAGRSLNTFYASWAKGRFTISRASSTTVTLAMTSL TAADTATYFCARDGASSGYYFKLWGPGTLVTVSS | 145 |
| | Light | ELVMTQTPSPVSAAVGGTVSISCQASKSVYNNNALSWYQQKPG QPPKLLIYSASTLASGVPSRFSGSGSGTEFTLTISGVQCDDAA TYYCAGGYSIISDNGFGGGTEVVVK | 146 |
| ETP-mAb70 | Heavy | RAVGKESEGGGLVQPEGSLTLTCTASGESESRSDYMCWVRQAPG KGLEWIGWIDPGYSDTYYASWAQGRTTISKASSTTVTLQMTSL TVADTATYFCARDLGFDSNLWGPGTLVTISS | 147 |
| | Light | ELDLTQTPASVEAAVGGTVTINCQASQSINSWLSWYQQKPGQR PKLLIYEASTLASGVSSRFSGSGSGTQFTLTISGVQCDDAATY YCQQGYSYSNVDNNIFGGGTEVVVK | 148 |
| ETP-mAb72 | Heavy | QSLEESGGGLVQPEGSLTLTCTASGFSFSRGDYVCWVRQAPGK GLEWIGWIDVGSVIESYYATWAKGRFTISKTSSTTVTLQMTSL TVADTATYFCARDLGFDTNLWGPGTLVTVSS | 149 |
| | Light | ELVMTQTPASVEAAVGGTVTINCQASESISIYLNWYQQKPGQP PKLLIYQASKLASGVPSRFKGSGSGTEFTLTISDLECADAATY YCQSHDYRIGRSDCNVFGGGTNVEIK | 150 |

Figure 3A:
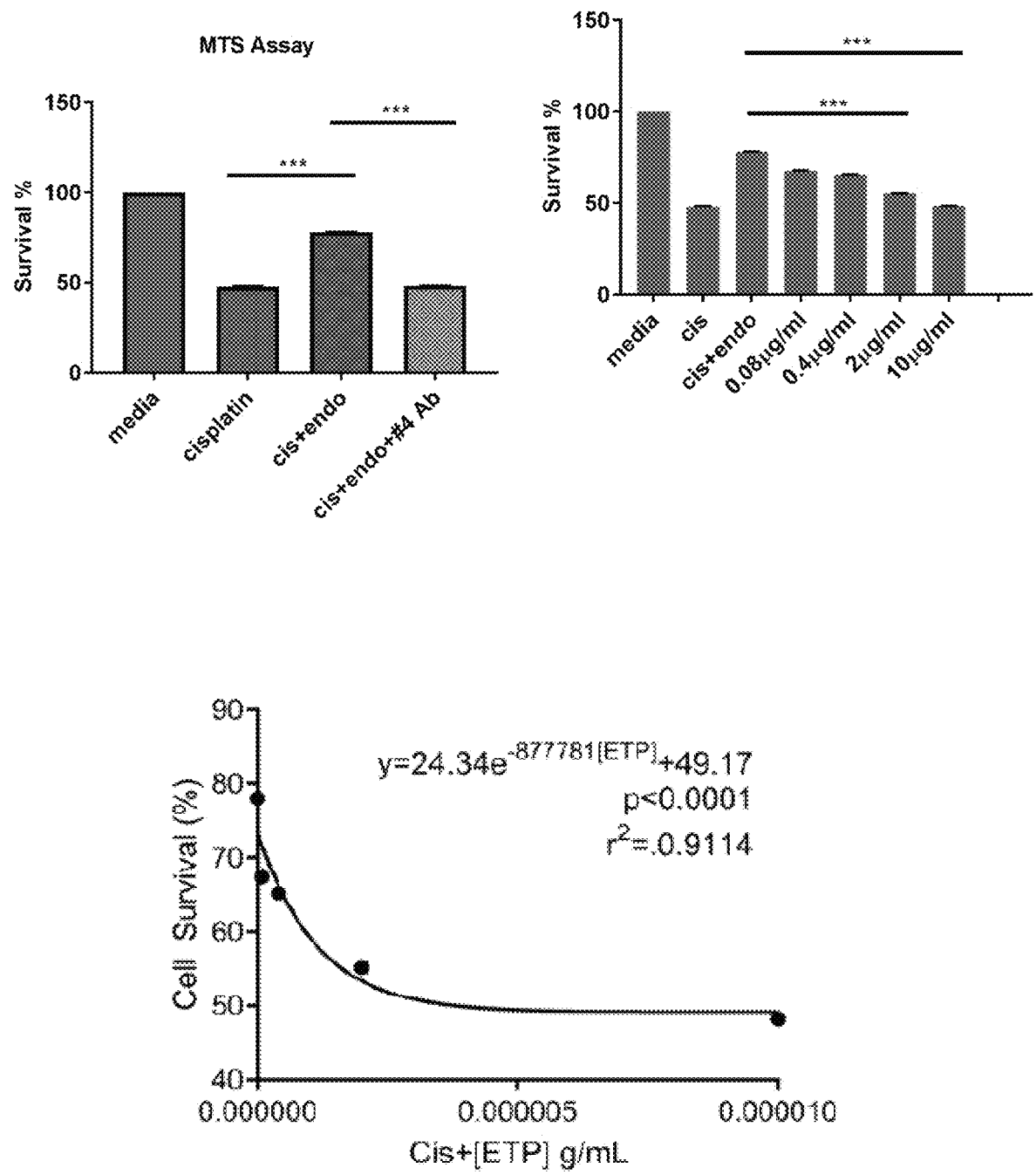
FIGS. 3A-D. Generation and screening of anti-human endotrophin.
Figure 3B:
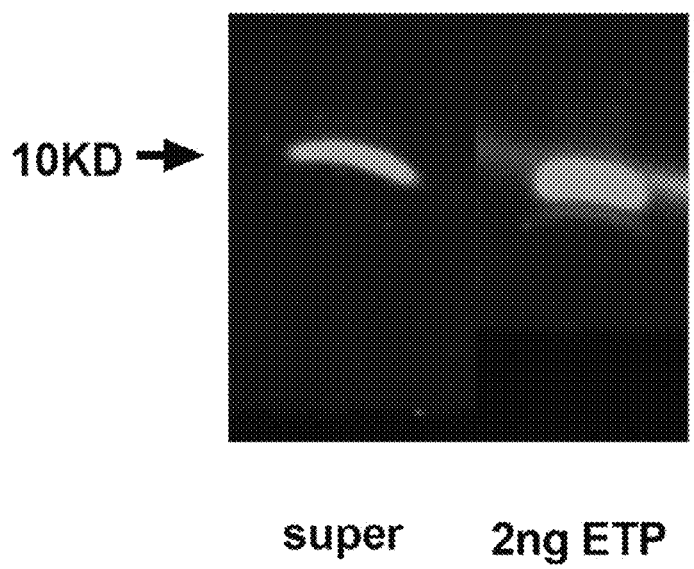
Figure 3C:
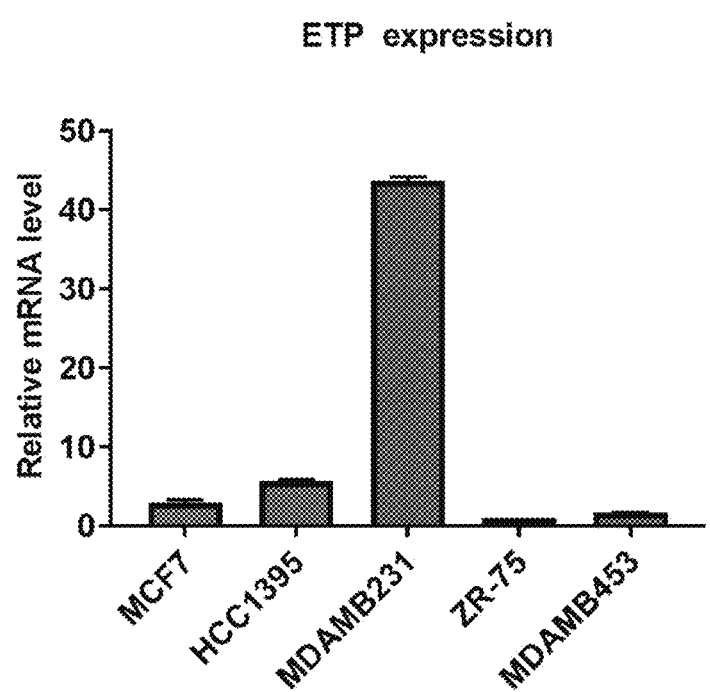
Figure 3D:
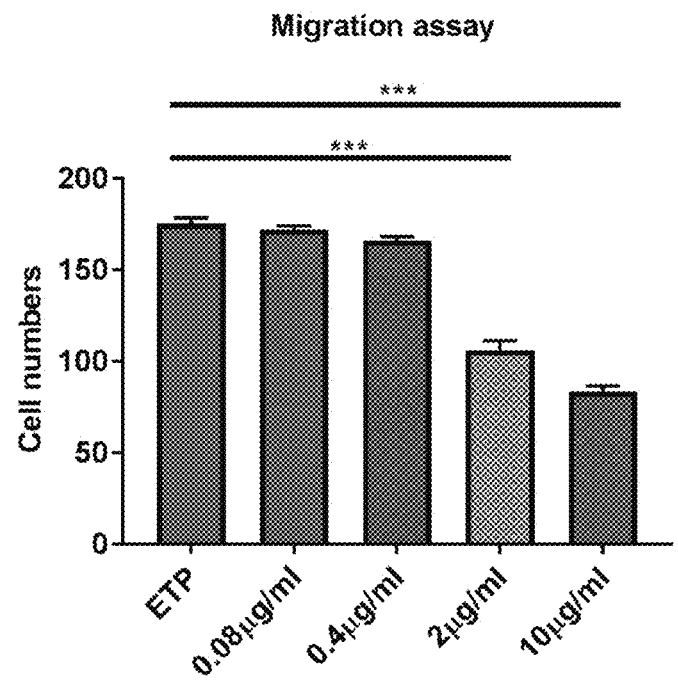
Figure 8:
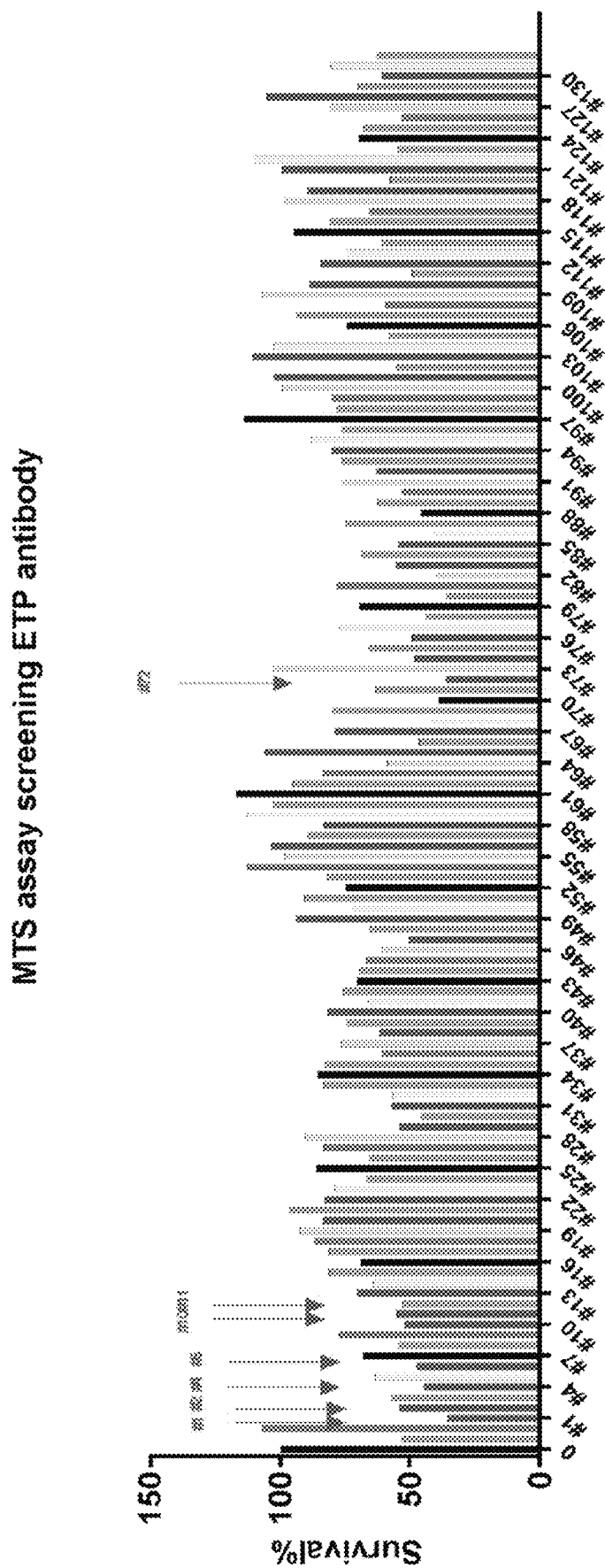
Figure 9:
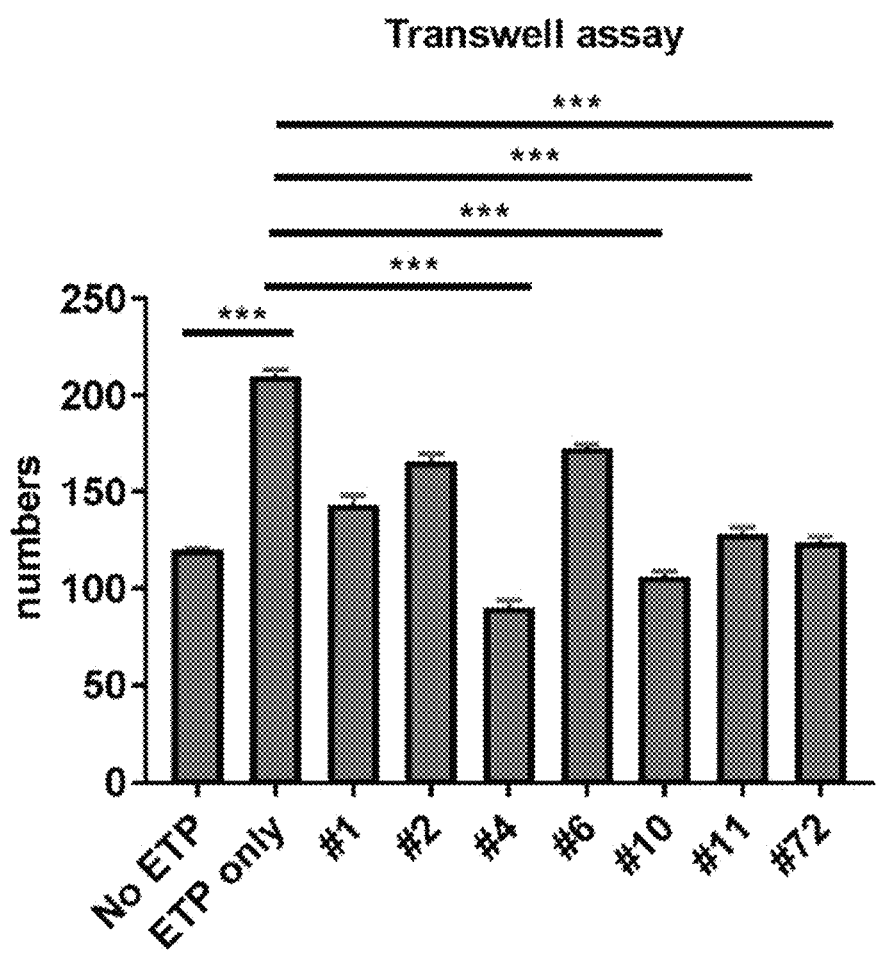
FIG. 9. SC macrophage cells (50,000 cells) were seeded at the top of a chamber. Then 100 ng/ml of endotrophin was added with 1% FBS in the bottom chamber. Next, 10 μg/mL of anti-ETP antibodies (#1, #2, #4, #6, #10, #11 and #72) were added to the bottom chamber and incubated for 2 hr. Migrated cells were counted after 2 hr. Data are represented as mean±SD and statistical significance (*** p<0.0001) was calculated using an unpaired Student's t-test.

A panel of 132 monoclonal antibodies were examined, not only for immune-crossreactivity against human endotrophin, but also for their ability to neutralize endotrophin action. To achieve this, an assay was established with the human breast cancer cell line, MCF-7 (Soule et al., 1973). These cells express very low levels of endotrophin, and as such, this renders them susceptible to the actions of cisplatinum. The presence of recombinant endotrophin results in an increased resistance to cisplatinum. The screening assay aimed to examine the effectiveness of the antibodies to neutralize endotrophin action, thereby making the cells susceptible again to cisplatinum-induced cell death (FIG. 8). Additional screening of 10 a subset of antibodies was performed with trans-well assays, with SC macrophage cells migrating towards endotrophin; this helped to corroborate the initial findings (FIG. 9). Based on these screening experiments one rabbit monoclonal antibody, which was named ETPmAb4, was selected for further study. These assays were repeated with ETPmAb4, and ETPmAb4 was found to completely neutralize endotrophin-mediated MCF-7 cell survival (FIG. 3A). Furthermore, MCF-7 cells exposed to endotrophin became cisplatinum resistant, whereas treatment with antibody ETPmAb4 forced the cells to become susceptible to cisplatinum, in a dose-dependent manner. The inventors generated MCF-7 cells that were stably transfected with a control vector, or isolated a MCF-7 clone that was transfected with a plasmid, enabling the expression of endotrophin under the control of a signal sequence, which effectively enabled these cells to secrete endotrophin into the tissue culture supernatant (FIG. 3B). Of note, is the fact that MCF-7 cells express very low levels of endogenous endotrophin (FIG. 3C). Using these stable endotrophin expressing MCF-7 transfectants, macrophages were seeded in the top chamber of a trans-well plate, and endotrophin overexpressing MCF-7 cells were seeded at the bottom. The inclusion of ETPmAb4 along with the MCF-7 overexpressing cells, effectively prevented the migration of the SC macrophages into the bottom chamber, and the neutralizing activity of ETPmAb4 was dose-responsive (FIG. 3D).

Example 4—In Vivo Effects of Endotrophin Overexpressing MCF7 Cells

Figure 4A:
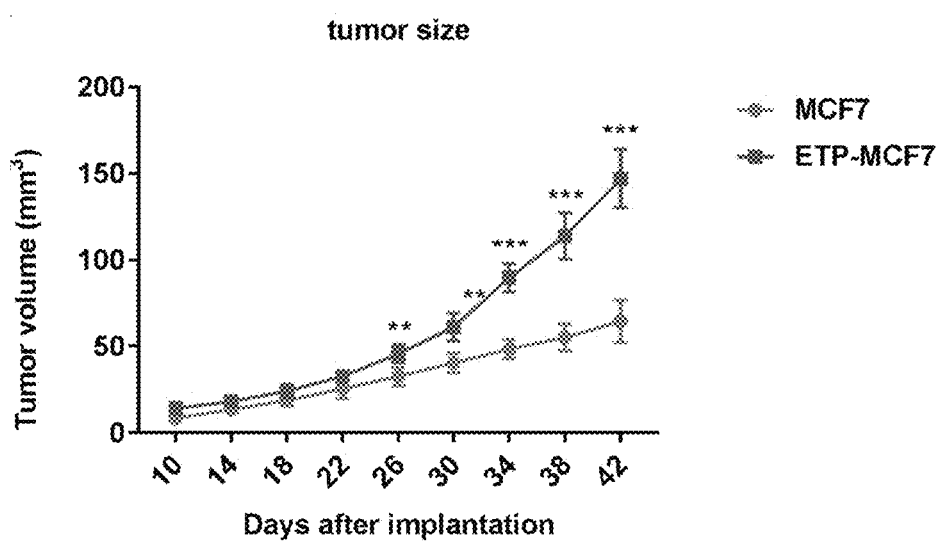
FIGS. 4A-C. The in vivo effects of endotrophin overexpressing MCF7 cells.
Figure 4B:
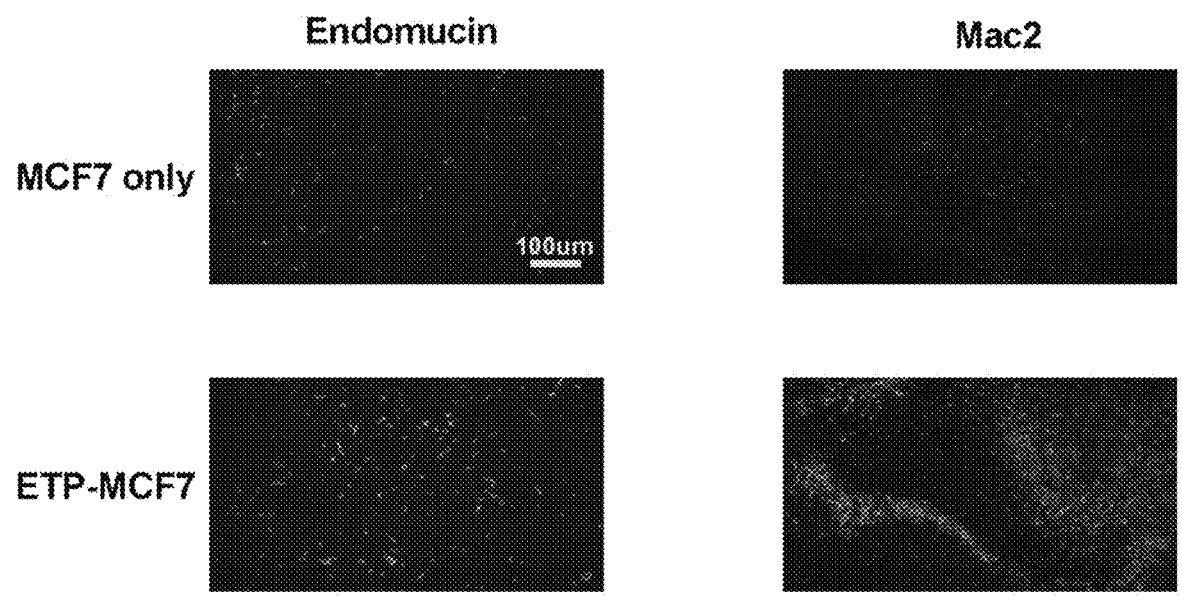

To establish the system in vivo, the relative rate of tumor growth was compared between MCF-7 cells that were stably transfected with a control vector and the MCF-7 clone that was transfected with a plasmid enabling the expression and secretion of endotrophin. Two million cells were injected into the flank of nude mice. Control MCF-7 cells were injected into one side of mice, and MCF-7 cells overexpressing endotrophin were injected into the other side of mice. Lesion growth was subsequently monitored (FIG. 4A). MCF-7 cells that overexpress endotrophin showed a significantly faster rate of tumor growth than control cells, further supporting the strong pro-mitogenic effect that endotrophin exerts on tumor cells. MCF-7 tumor lesions with higher levels of endotrophin showed higher vascular density (as judged by the higher density of endomucin staining), and an increased rate of tumor-associated macrophage infiltration (as judged by the higher density of Mac2 staining) (FIG. 4B).

Example 5—Use of a Novel Mass Spectroscopy-Based Methodology to Determine the In Vivo Half-Life of the Monoclonal Anti-Endotrophin ETPmAb4

Figure 4C:
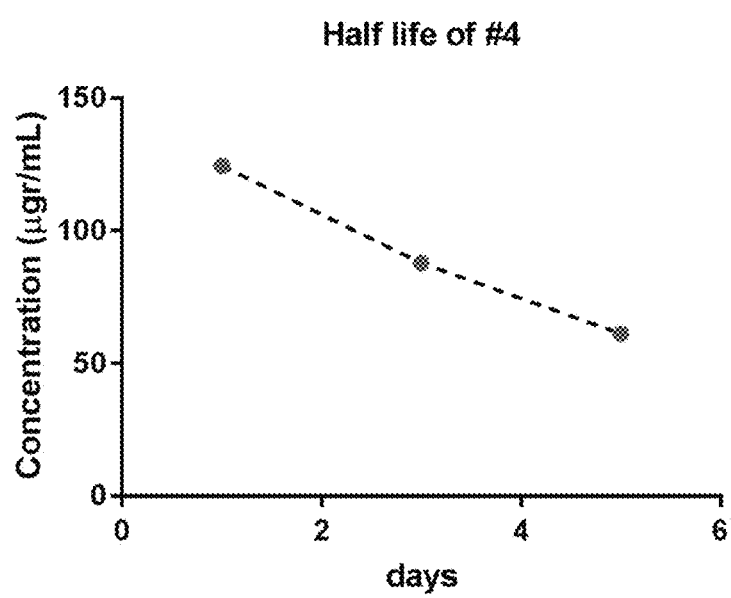

To acquire a better sense of the plasma half-life of ETPmAb4 in vivo, a nude mouse was injected with 200 μg of antibody, and then novel state-of-the-art mass spectrometry-based quantitation method was used to determine the injection schedule for future experiments. The methodology relies on a partial trypsin digest step that generates a unique fingerprint of cleavage products; this consequently allows for the identification of the relative amounts of a unique antibody population amongst plasma, which contains a large number of different endogenous antibodies (nSMOL™ Shimadzu Corporation Kyoto, Japan). FIG. 4C shows that the half-life of antibody ETPmAb4 in the nude mouse is approximately five days.

Figure 5A:
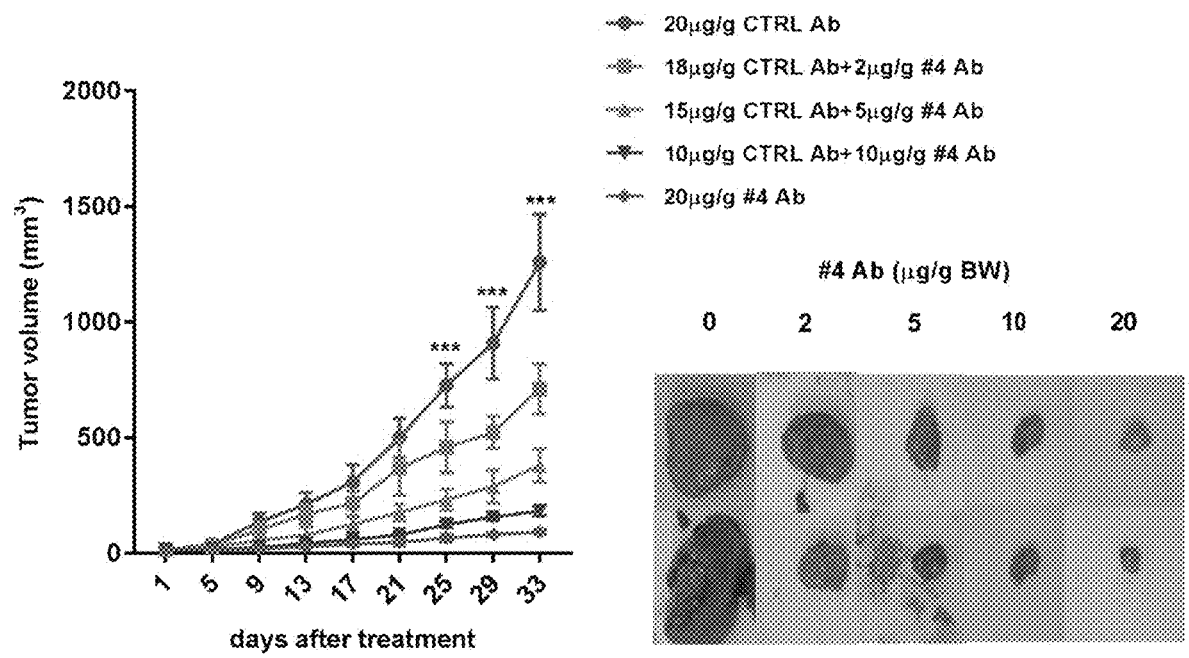
FIGS. 5A-C. Antibody effects on ETP-MCF7 cells in vivo.
Figure 5B:
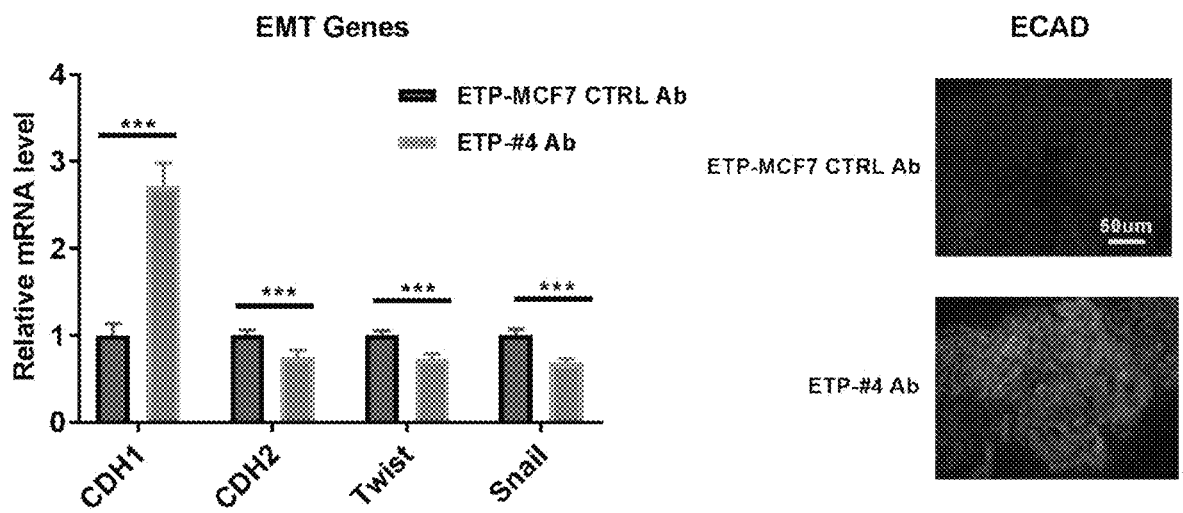

Example 6-Anti-Endotrophin Antibodies Significantly Curb Lesion Growth of MCF7-ETP Cells In Vivo As a next step, whether the anti-endotrophin antibodies effectively curb the aggressive tumor growth observed in endotrophin overexpressing MCF-7 cells was examined. To boost the growth rate of the tumor cells, these assays were performed in the presence of estradiol pellets. Cells ($2\times10^6$ cells) were injected into nude mice and their tumor growth was monitored over time, based on a twice weekly injection of either a control monoclonal preparation, or ETPmAb4; in all cases, a total of 20 mg/kg of antibody was used. The dose dependence was tested by either injecting 20 mg/kg of control antibody, 20 mg/kg of ETPmAb4, or a mixture of the two with decreasing levels of control antibody mixed with increasing levels of ETPmAb4. As observed in FIG. 5A, the presence of neutralizing endotrophin antibody significantly reduced in a dose-dependent fashion the rate of tumor growth over time; with the highest dose of ETPmAb4 almost completely curbing the aggressive tumor growth observed in the presence of control antibody alone. Consistent with this, real-time qPCR analyses revealed a reduced EMT signature, with a significant upregulation in Cdh 1 (E-cadherin) gene expression levels, with a concomitant downregulation in Cdh2 (N-cadherin), Twist and Snail expression levels (FIG. 5B). The increased Cdh1 (E-cadherin) gene expression levels in the antibody-treated group are also apparent at the protein level, as judged by the markedly enhanced staining intensity with E-cadherin antibodies (FIG. 5B). This indicates that neutralization of endotrophin effectively reduces the EMT process, and further suggests that the antibody-treated tumors should be more sensitive to the actions of chemotherapeutic agents.

Figure 5C:
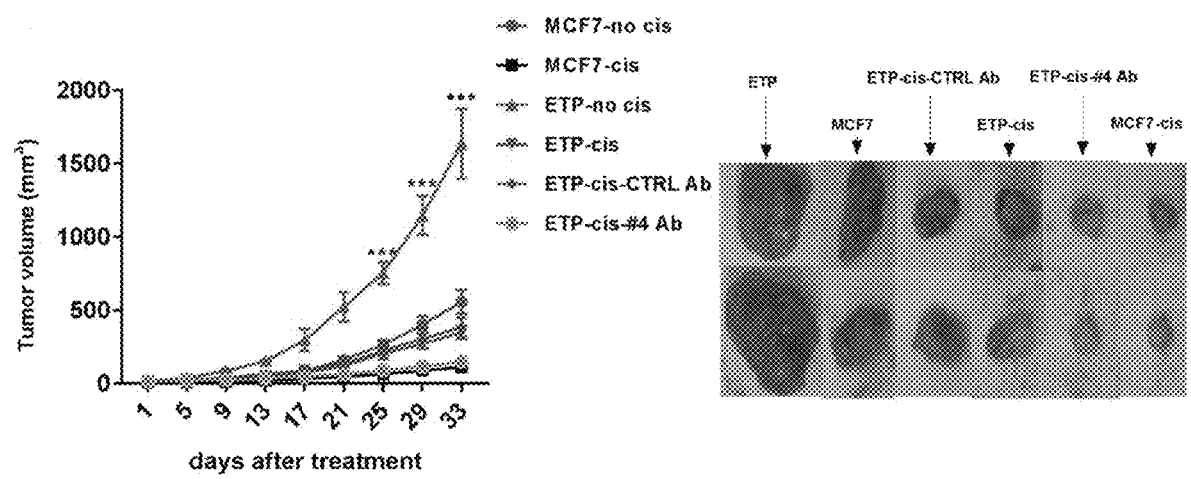

Example 7—Anti-Endotrophin Antibodies Significantly Enhance the Cisplatinum Susceptibility of MCF7-ETP Cells In Vivo Whether the in vitro findings that suggest enhanced susceptibility to cisplatinum upon neutralization of endotrophin would translate to an in vivo situation was tested next. To test this, MCF7 cells were used with or without endotrophin overexpression, and the cells were transplanted into nude mice, in the presence of estradiol pellets (FIG. 5C). While MCF7 cells grew effectively under these conditions (FIG. 5C; green line), cisplatinum significantly curbed lesion growth (FIG. 5C; black line). As expected, MCF7 cells harboring an excess in endotrophin grew very aggressively (FIG. 5C; red line). In the presence of cisplatinum, or in the presence of cisplatinum with control antibody, lesion growth was moderately reduced (FIG. 5C; pink and blue lines). In the presence of cisplatinum and ETPmAb4 (FIG. 5C; orange line), lesion growth was reduced down to essentially baseline; indicating that in the presence of the ETPmAb4, cells become highly susceptible to cisplatinum-induced growth arrest.

Figure 6A:
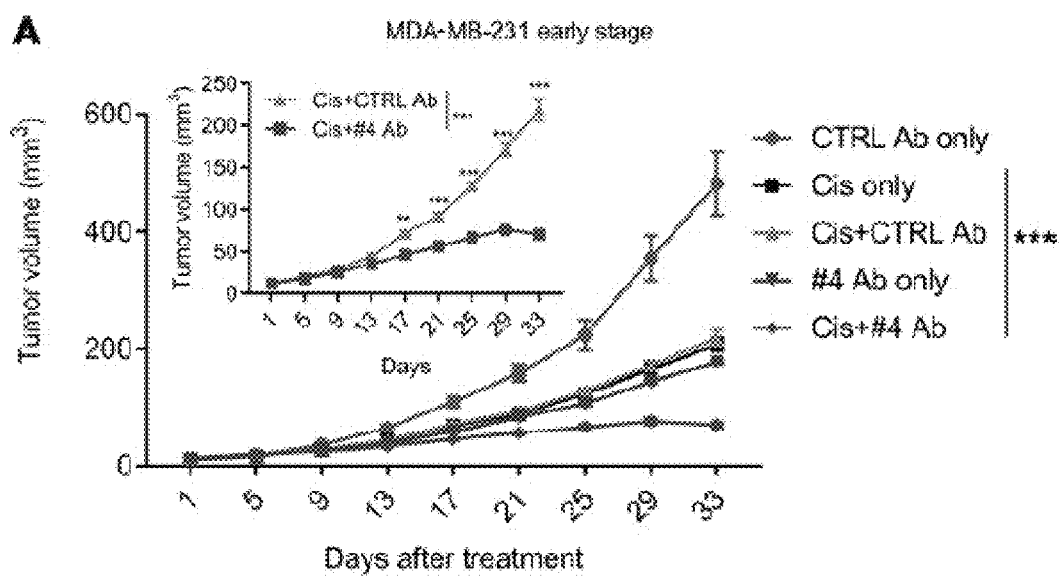
FIGS. 6A-D. The antibody effects on MDA-MB-231 cells in vivo.
Figure 6B:
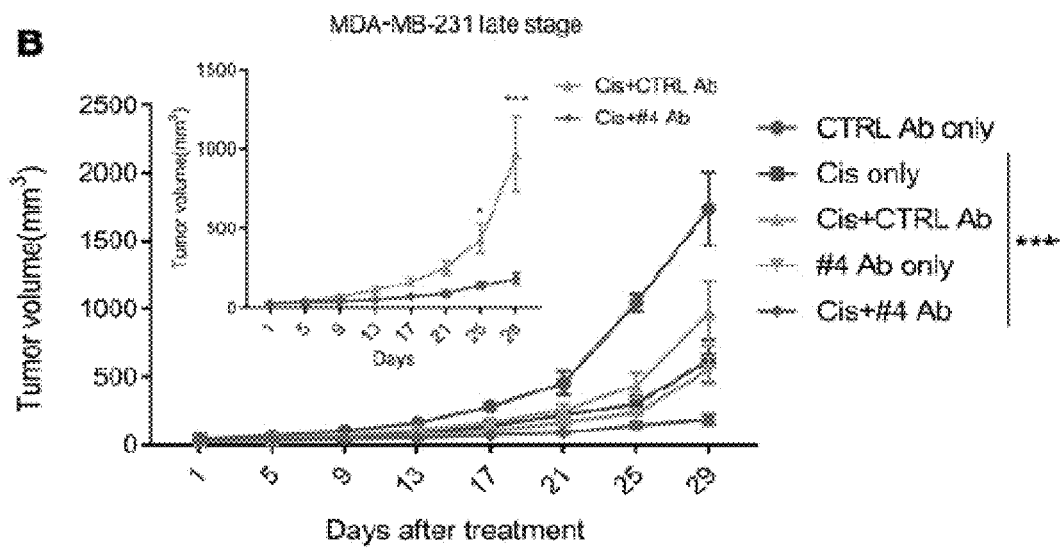
Figure 6C:
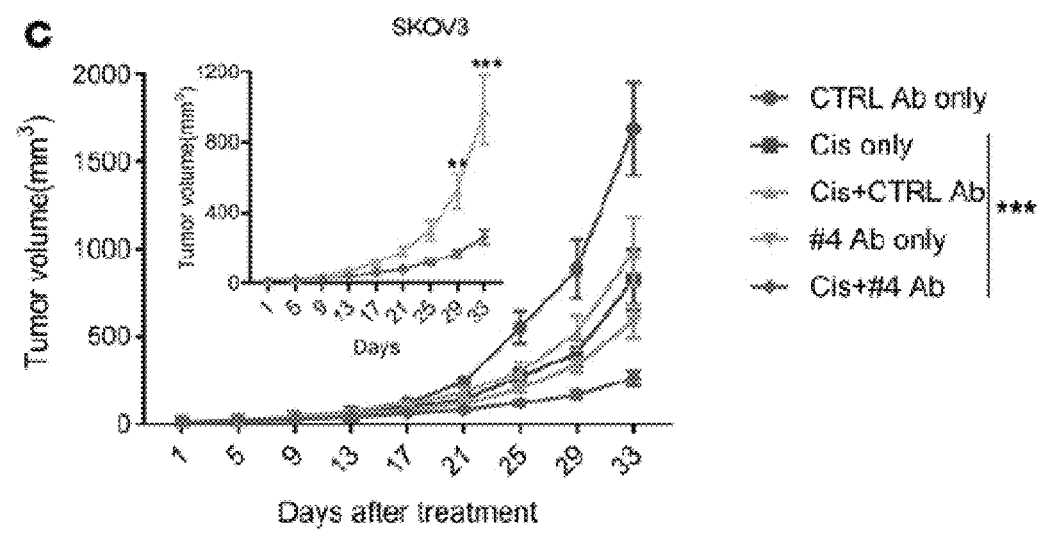

Example 8—Anti-Endotrophin Antibodies Significantly Curb Tumor Growth and Enhance Cisplatinum Susceptibility of MDA-MB23 Cells In Vivo Endotrophin-overexpressing MCF7 cells serve as an excellent tool to establish the basic parameters of the in vivo experiments. To establish the usefulness of endotrophin inhibition, the inventors wanted to establish that this approach works effectively with tumor cells that express endotrophin endogenously at significant levels. For this purpose, the MDA-MB23 breast cancer cell-line was used (FIG. 3C). Injection of these cells into nude mice established an aggressive lesion growth (FIG. 6A; red line), which was reduced in the presence of cisplatinum, or cisplatinum with the control antibodies (20 mg/kg) (FIG. 6A; black and green lines). The mere presence of ETPmAb4 significantly reduced the rate of tumor growth, and the combination of ETPmAb4 with cisplatinum, essentially inhibited lesion growth. This underlines the effective anti-mitogenic effects of ETPmAb4, and its ability to render the cells susceptible to cisplatinum.

Example 9—A Humanized Version of the Anti-Endotrophin Antibody Significantly Curbs Tumor Growth and Enhances Cisplatinum Susceptibility of MDA-MB23 Cells In Vivo For potential clinical development, ETPmAb4 was humanized by designing 5 humanized heavy chain sequences and one humanized light chain sequence (Tables 7 and 8) for generation of humanized IgG1 antibody using a CDR grafting strategy (Zhang & Ho, 2017; Yu et al., 2010). The humanized antibody was named hETPmAb4. The DNA and amino acid variable sequences of the humanized antibodies are provided in Tables 7 and 8, respectively.

Figure 6D:
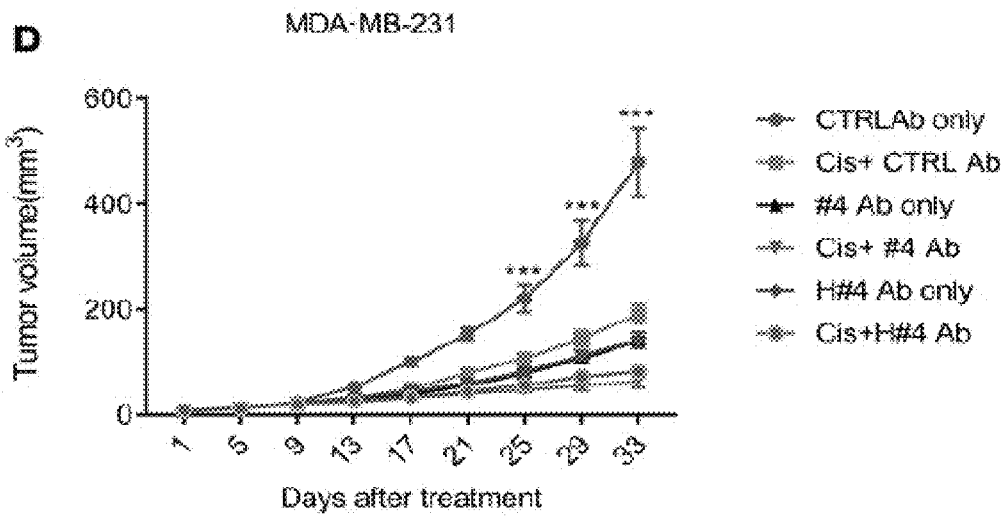
Figure 7:
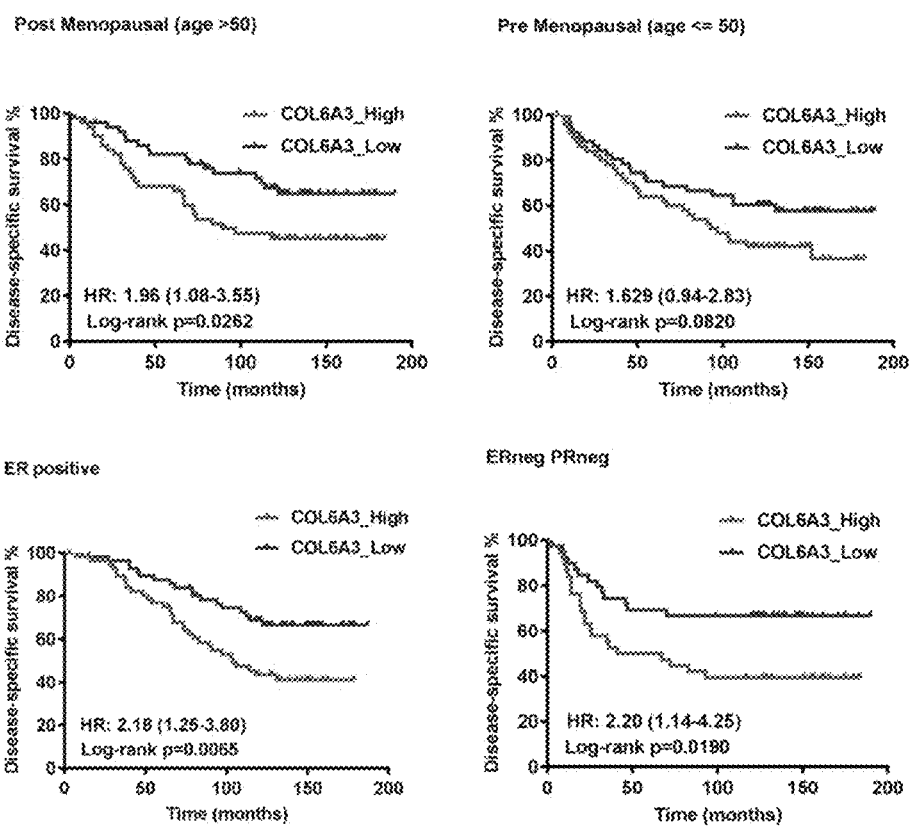
FIG. 7. Col6α3 expression in pre- and post-menopausal tumors, and different tumor subtypes. Data shown in FIG. 1 was subdivided into pre- and post-menopausal breast cancer (top), or into estrogen receptor positive and estrogen receptor negative subpopulations (bottom).

After humanization, the binding affinity of hETPmAb4 to endotrophin was measured in Octet RED96. The $K_d$ of hETPmAb4 binding to endotrophin as measured by Octet RED96 is 1.52 nM which is comparable to the Kd of 1.62 nM for the parental ETPmAb4. These results suggest that hETPmAb4 maintained the binding affinity of the parental rabbit ETPmAb4. The same in vivo experiments that were shown in FIG. 6A were repeated, with the hETPmAb4. As observed in FIG. 6D, the exact same response was observed as in FIG. 6A, indicating that the humanization process did not impact the in vivo efficacy of the parental rabbit monoclonal antibody ETPmAb4.

TABLE 7

Nucleotide sequences for humanized antibody variable regions

| Antibody Name | Chain | Variable Sequence (5' to 3') | SEQ ID NO: |
|---|---|---|---|
| ENT-hMab4.1 | Heavy | GAGGTCCAGCTGCTGGAGAGCGGAGGAGGACTGGTGCAGCCCGGA GGATCTTTAAGACTGAGCTGTGCCGCCAGCGGCTTCAGCTTCAGC AGCGGCTACTACATCTGCTGGGTGAGACAAGCTCCCGGTAAAGGT TTAGAGTGGATCGCTTGTATCTACGGCGGCAACAACAACCCCTAC TACGCCAACTGGGTGAACGGCAGATTCACCATCTCTCGTGACAAC AGCAAGAACACTTTATATTTACAGATGAACTCTTTAAGGGCCGAG GACACCGCCGTGTACTACTGCGCTCGTAAGGACATCAACATCGGC GGCGCCTATGAGCTGTGGGGCCAAGGTACTTTAGTGACCGTGAGC AGC | 151 |
| | Light | GACATCCAGATGACCCAGAGCCCTAGCTCTTTAAGCGCCAGCGTG GGCGACAGAGTGACCATCACTTGTCAAGCTAGCCAGAGCATCAGC AGCAGCTATTTAAGCTGGTACCAGCAGAAGCCCGGCAAGGCCCCC AAGCTGCTGATCTACAAGGCCAGCACACTGGCCAGCGGCGTGCCT TCTCGTTTTAGCGGCAGCGGCAGCGGAACCGACTTCACTTTAACC ATCAGCTCTTTACAGCCCGAGGACTTCGCCACCTACTACTGCCAG TACAGCGACTGGGCCAACAGCTATGGCAACGCCTTCGGCGGCGGC ACCAAGGTGGAGATCAAG | 152 |
| ENT-hMab4.2 | Heavy | GAGGTCCAGCTGCTGGAGAGCGGAGGAGGACTGGTGCAGCCCGGA GGATCTTTAAGACTGAGCTGTGCCGCCAGCGGCTTCAGCTTCAGC AGCGGCTACTACATCTGCTGGGTGAGACAAGCTCCCGGTAAAGGT TTAGAGTGGATCGCTTGTATCTACGGCGGCAACAGCAACCCCTAC TACGCCAACTGGGTGAACGGCAGATTCACCATCTCTCGTGACAAC AGCAAGAACACTTTATATTTACAGATGAACTCTTTAAGGGCCGAG GACACCGCCGTGTACTACTGCGCTCGTAAGGACATCAACATCGGC GGCGCCTATGAGCTGTGGGGCCAAGGTACTTTAGTGACCGTGAGC AGC | 153 |
| | Light | GACATCCAGATGACCCAGAGCCCTAGCTCTTTAAGCGCCAGCGTG GGCGACAGAGTGACCATCACTTGTCAAGCTAGCCAGAGCATCAGC AGCAGCTATTTAAGCTGGTACCAGCAGAAGCCCGGCAAGGCCCCC AAGCTGCTGATCTACAAGGCCAGCACACTGGCCAGCGGCGTGCCT TCTCGTTTTAGCGGCAGCGGCAGCGGAACCGACTTCACTTTAACC ATCAGCTCTTTACAGCCCGAGGACTTCGCCACCTACTACTGCCAG TACAGCGACTGGGCCAACAGCTATGGCAACGCCTTCGGCGGCGGC ACCAAGGTGGAGATCAAG | 152 |
| ENT-hMab4.3 | Heavy | GAGGTCCAGCTGCTGGAGAGCGGAGGAGGACTGGTGCAGCCCGGA GGATCTTTAAGACTGAGCTGTGCCGCCAGCGGCTTCAGCTTCAGC AGCGGCTACTACATCTGCTGGGTGAGACAAGCTCCCGGTAAAGGT TTAGAGTGGATCGCTTGTATCTACGGCGGCAACAGCAACCCCTAC TACGCCAACTGGGTGAACGGCAGATTCACCACCTCTCGTGACAAC AGCAAGAACACTTTATATTTACAGATGAACTCTTTAAGGGCCGAG GACACCGCCGTGTACTACTGCGCTCGTAAGGACATCAACATCGGC GGCGCCTATGAGCTGTGGGGCCAAGGTACTTTAGTGACCGTGAGC AGC | 154 |
| | Light | GACATCCAGATGACCCAGAGCCCTAGCTCTTTAAGCGCCAGCGTG GGCGACAGAGTGACCATCACTTGTCAAGCTAGCCAGAGCATCAGC AGCAGCTATTTAAGCTGGTACCAGCAGAAGCCCGGCAAGGCCCCC | 152 |

TABLE 7-continued

Nucleotide sequences for humanized antibody variable regions

| Antibody Name | Chain | Variable Sequence (5' to 3') | SEQ ID NO: |
|---|---|---|---|
| | | AAGCTGCTGATCTACAAGGCCAGCACACTGGCCAGCGGCGTGCCT TCTCGTTTTAGCGGCAGCGGCAGCGGAACCGACTTCACTTTAACC ATCAGCTCTTTACAGCCCGAGGACTTCGCCACCTACTACTGCCAG TACAGCGACTGGGCCAACAGCTATGGCAACGCCTTCGGCGGCGGC ACCAAGGTGGAGATCAAG | |
| ENT-hMab4.4 | Heavy | GAGGTCCAGCTGCTGGAAAGCGGAGGAGGACTGGTGCAGCCCGGT GGCTCTTTAAGACTGAGCTGCGCTGCCAGCGGCTTCAGCTTCAGC AGCGGCTACTACATCTGCTGGGTGAGACAAGCTCCCGGTAAGGGT TTAGAGTGGATCGCTTGTATCTACGGCGGCAACAACAACCCCTAC TACGCCAACTGGGTGAACGGTCGTTTCACCACCTCTCGTGACAAC AGCAAGAACACTTTATATTTACAGATGAACTCTTTAAGGGCCGAG GACACCGCCGTGTACTACTGCGCTAGGAAGGACATCAACATCGGC GGCGCCTACGAACTGTGGGGACAAGGTACTTTAGTGACCGTGAGC AGC | 155 |
| | Light | GACATCCAGATGACCCAGAGCCCTAGCTCTTTAAGCGCCAGCGTG GGCGACAGAGTGACCATCACTTGTCAAGCTAGCCAGAGCATCAGC AGCAGCTATTTAAGCTGGTACCAGCAGAAGCCCGGCAAGGCCCCC AAGCTGCTGATCTACAAGGCCAGCACACTGGCCAGCGGCGTGCCT TCTCGTTTTAGCGGCAGCGGCAGCGGAACCGACTTCACTTTAACC ATCAGCTCTTTACAGCCCGAGGACTTCGCCACCTACTACTGCCAG TACAGCGACTGGGCCAACAGCTATGGCAACGCCTTCGGCGGCGGC ACCAAGGTGGAGATCAAG | 152 |
| ENT-hMab4.5 | Heavy | GAGGTCCAGCTGCTGGAGAGCGGAGGAGGACTGGTGCAGCCCGGA GGATCTTTAAGACTGAGCTGTGCCGCCAGCGGCTTCACCTTCAGC AGCGGCTACTACATCTGCTGGGTGAGACAAGCTCCCGGTAAAGGT TTAGAGTGGATCGCTTGTATCTACGGCGGCAACAGCAACCCCTAC TACGCCAACTGGGTGAACGGCAGATTCACCATCTCTCGTGACAAC AGCAAGAACACTTTATATTTACAGATGAACTCTTTAAGGGCCGAG GACACCGCCGTGTACTACTGCGCTCGTAAGGACATCAACATCGGC GGCGCCTATGAGCTGTGGGGCCAAGGTACTTTAGTGACCGTGAGC AGC | 156 |
| | Light | GACATCCAGATGACCCAGAGCCCTAGCTCTTTAAGCGCCAGCGTG GGCGACAGAGTGACCATCACTTGTCAAGCTAGCCAGAGCATCAGC AGCAGCTATTTAAGCTGGTACCAGCAGAAGCCCGGCAAGGCCCCC AAGCTGCTGATCTACAAGGCCAGCACACTGGCCAGCGGCGTGCCT TCTCGTTTTAGCGGCAGCGGCAGCGGAACCGACTTCACTTTAACC ATCAGCTCTTTACAGCCCGAGGACTTCGCCACCTACTACTGCCAG TACAGCGACTGGGCCAACAGCTATGGCAACGCCTTCGGCGGCGGC ACCAAGGTGGAGATCAAG | 152 |

TABLE 8

Protein sequences for humanized antibody variable regions

| Antibody Name | Chain | Variable Sequence | SEQ ID NO: |
|---|---|---|---|
| ENT-hMab4.1 | Heavy | EVQLLESGGGLVQPGGSLRLSCAASGFSFSSGYYICWVRQAPGKG LEWIACIYGGNNNPYYANWVNGRFTISRDNSKNTLYLQMNSLRAE DTAVYYCARKDINIGGAYELWGQGTLVTVSS | 157 |
| | Light | DIQMTQSPSSLSASVGDRVTITCQASQSISSSYLSWYQQKPGKAP KLLIYKASTLASGVPSRESGSGSGTDFTLTISSLQPEDFATYYCQ YSDWANSYGNAFGGGTKVEIK | 158 |
| ENT-hMab4.2 | Heavy | EVQLLESGGGLVQPGGSLRLSCAASGFSFSSGYYICWVRQAPGKG LEWIACIYGGNSNPYYANWVNGRFTISRDNSKNTLYLQMNSLRAE DTAVYYCARKDINIGGAYELWGQGTLVTVSS | 159 |
| | Light | DIQMTQSPSSLSASVGDRVTITCQASQSISSSYLSWYQQKPGKAP KLLIYKASTLASGVPSRFSGSGSGTDFTLTISSLQPEDFATYYCQ YSDWANSYGNAFGGGTKVEIK | 158 |
| ENT-hMab4.3 | Heavy | EVQLLESGGGLVQPGGSLRLSCAASGFSFSSGYYICWVRQAPGKG LEWIACIYGGNSNPYYANWVNGRFTTSRDNSKNTLYLQMNSLRAE DTAVYYCARKDINIGGAYELWGQGTLVTVSS | 160 |
| | Light | DIQMTQSPSSLSASVGDRVTITCQASQSISSSYLSWYQQKPGKAP KLLIYKASTLASGVPSRFSGSGSGTDFTLTISSLQPEDFATYYCQ YSDWANSYGNAFGGGTKVEIK | 158 |

TABLE 8-continued

Protein sequences for humanized antibody variable regions

| Antibody Name | Chain | Variable Sequence | SEQ ID NO: |
|---|---|---|---|
| ENT-hMab4.4 | Heavy | EVQLLESGGGLVQPGGSLRLSCAASGFSFSSGYYICWVRQAPGKG LEWIACIYGGNNNPYYANWVNGRFTTSRDNSKNTLYLQMNSLRAE DTAVYYCARKDINIGGAYELWGQGTLVTVSS | 161 |
|  | Light | DIQMTQSPSSLSASVGDRVTITCQASQSISSSYLSWYQQKPGKAP KLLIYKASTLASGVPSRESGSGSGTDFTLTISSLQPEDFATYYCQ YSDWANSYGNAFGGGTKVEIK | 158 |
| ENT-hMab4.5 | Heavy | EVQLLESGGGLVQPGGSLRLSCAASGFTFSSGYYICWVRQAPGKG LEWIACIYGGNSNPYYANWVNGRFTISRDNSKNTLYLQMNSLRAE DTAVYYCARKDINIGGAYELWGQGTLVTVSS | 162 |
|  | Light | DIQMTQSPSSLSASVGDRVTITCQASQSISSSYLSWYQQKPGKAP KLLIYKASTLASGVPSRFSGSGSGTDFTLTISSLQPEDFATYYCQ YSDWANSYGNAFGGGTKVEIK | 158 |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Calle E E, Rodriguez C, Walker-Thurmond K, and Thun M J. Overweight, obesity, and mortality from cancer in a prospectively studied cohort of U.S. adults. N Engl J Med. 2003; 348 (17): 1625-38.

Chrisanthar R, Knappskog S, Lokkevik E, Anker G, Ostenstad B, Lundgren S, et al. Predictive and prognostic impact of TP53 mutations and MDM2 promoter genotype in primary breast cancer patients treated with epirubicin or paclitaxel. PloS one. 2011; 6 (4): e19249.

Fan X, Brezski R J, Fa M, Deng H, Oberholtzer A, Gonzalez A, et al. A single proteolytic cleavage within the lower hinge of trastuzumab reduces immune effector function and in vivo efficacy. Breast Cancer Res. 2012; 14 (4): R116.

Fenton A, Jesky M D, Ferro C J, Sorensen J, Karsdal M A, Cockwell P, et al. Serum endotrophin, a type VI collagen cleavage product, is associated with increased mortality in chronic kidney disease. PloS one. 2017;12 (4): e0175200.

Freed D C, Tang Q, Tang A, Li F, He X, Huang Z, et al. Pentameric complex of viral glycoprotein H is the primary target for potent neutralization by a human cytomegalovirus vaccine. Proc Natl Acad Sci USA. 2013; 110 (51): E4997-5005.

Galdal K S, Evensen S A, Hoglund A S, and Nilsen E. Actin pools and actin microfilament organization in cultured human endothelial cells after exposure to thrombin. Br J Haematol. 1984;58 (4): 617-25.

Gupta O T, and Gupta R K. Visceral Adipose Tissue Mesothelial Cells: Living on the Edge or Just Taking Up Space? Trends Endocrinol Metab. 2015;26 (10): 515-23. Herren B, Raines E W, and Ross R. Expression of a disintegrin-like protein in cultured human vascular cells and in vivo. FASEB J. 1997;11 (2): 173-80.

Iwamoto N, Shimada T, Umino Y, Aoki C, Aoki Y, Sato T A, et al. Selective detection of complementarity-determining regions of monoclonal antibody by limiting protease access to the substrate: nano-surface and molecular-orientation limited proteolysis. Analyst. 2014; 139 (3): 576-80.

Iyengar P, Espina V, Williams T W, Lin Y, Berry D, Jelicks L A, et al. Adipocyte-derived collagen V I affects early mammary tumor progression in vivo, demonstrating a critical interaction in the tumor/stroma microenvironment. J Clin Invest. 2005;115 (5): 1163-76.

Iyengar P, CombsT.P., Shah S J, Gouon-Evans V, Pollard J W, Albanese C, et al. Adipocyte Secreted Factors Synergistically Promote Mammary Tumorigenesis Through Induction of anti-Apoptotic Transcriptional Programs and Proto-Oncogene Stabilization. Oncogene. 2003; 22 (41): 6408-23.

Karsdal M A, Henriksen K, Genovese F, Leeming D J, Nielsen M J, Riis B J, et al. Serum endotrophin identifies optimal responders to PPARgamma agonists in type 2 diabetes. Diabetologia. 2017;60 (1): 50-9.

Keydar I, Chen L, Karby S, Weiss F R, Delarea J, Radu M, et al. Establishment and characterization of a cell line of human breast carcinoma origin. Eur J Cancer. 1979;15 (5): 659-70.

Khan T, Muise E S, Iyengar P, Wang Z V, Chandalia M, Abate N, et al. Metabolic dysregulation and adipose tissue fibrosis: role of collagen V I. Mol Cell Biol. 2009; 29 (6): 1575-91.

Maheshwari R K, Srikantan V, Bhartiya D, Kleinman H K, and Grant D S. Differential effects of interferon gamma and alpha on in vitro model of angiogenesis. J Cell Physiol. 1991;146 (1): 164-9.

Park J, and Scherer P E. Endotrophin-a novel factor linking obesity with aggressive tumor growth. Oncotarget. 2012a;3 (12): 1487-8.

Park J, and Scherer P E. Adipocyte-derived endotrophin promotes malignant tumor progression. J Clin Invest. 2012b;122 (11): 4243-56.

Park J, and Scherer P E. Endotrophin in the tumor stroma: a new therapeutic target for breast cancer? Expert review of anticancer therapy. 2013; 13 (2): 111-3.

Park J, Morley T S, and Scherer P E. Inhibition of endotrophin, a cleavage product of collagen VI, confers cisplatin sensitivity to tumours. EMBO molecular medicine. 2013; 5 (6): 935-48.

Park J, Morley T S, and Scherer P E. Inhibition of endotrophin, a cleavage product of collagen VI, confers cisplatin sensitivity to tumours. EMBO molecular medicine. 2013; 5 (6): 935-48.

Park J, Morley T S, Kim M, Clegg D J, and Scherer P E. Obesity and cancer-mechanisms underlying tumour progression and recurrence. Nature reviews Endocrinology. 2014.

Rasmussen DGK, Fenton A, Jesky M, Ferro C, Boor P, Tepel M, et al. Urinary endotrophin predicts disease progression in patients with chronic kidney disease. Sci Rep. 2017;7 (1): 17328.

Rasmussen DGK, Hansen T W, von Scholten B J, Nielsen S H, Reinhard H, Parving H H, et al. Higher Collagen V I Formation Is Associated With All-Cause Mortality in Patients With Type 2 Diabetes and Microalbuminuria. Diabetes Care. 2018; 41 (7): 1493-500.

Rosivatz E, Becker I, Specht K, Fricke E, Luber B, Busch R, et al. Differential expression of the epithelial-mesenchymal transition regulators snail, SIP1, and twist in gastric cancer. Am J Pathol. 2002; 161 (5): 1881-91.

Sakata Y, Okada M, Noro A, and Matsuda M. Interaction of tissue-type plasminogen activator and plasminogen activator inhibitor 1 on the surface of endothelial cells. J Biol Chem. 1988;263 (4): 1960-9.

Sciacovelli M, and Frezza C. Metabolic reprogramming and epithelial-to-mesenchymal transition in cancer. The FEBS journal. 2017;284 (19): 3132-44.

Soule H D, Vazguez J, Long A, Albert S, and Brennan M. A human cell line from a pleural effusion derived from a breast carcinoma. J Natl Cancer Inst. 1973;51 (5): 1409-16.

Sun K, Park J, Gupta O T, Holland W L, Auerbach P, Zhang N, et al. Endotrophin triggers adipose tissue fibrosis and metabolic dysfunction. Nature communications. 2014; 5:3485.

Sun K, Park J, Kim M, and Scherer P E. Endotrophin, a multifaceted player in metabolic dysregulation and cancer progression, is a predictive biomarker for the response to PPARgamma agonist treatment. Diabetologia. 2017;60 (1): 24-9.

Treves A J. Human monocytes and macrophages: establishment and analysis of cloned populations and functional cell lines. Crit Rev Immunol. 1985;5 (4): 371-85.

Yang D, Singh A, Wu H, and Kroe-Barrett R. Comparison of biosensor platforms in the evaluation of high affinity antibody-antigen binding kinetics. Anal Biochem. 2016; 508:78-96.

Yu Y, Lee P, Ke Y, Zhang Y, Yu Q, Lee J, et al. A humanized anti-VEGF rabbit monoclonal antibody inhibits angiogenesis and blocks tumor growth in xenograft models. PloS one. 2010; 5 (2): e9072.

Zhang N, Deng H, Fan X, Gonzalez A, Zhang S, Brezski R J, et al. Dysfunctional Antibodies in the Tumor Microenvironment Associate with Impaired Anticancer Immunity. Clin Cancer Res. 2015;21 (23): 5380-90.

Zhang YF, and Ho M. Humanization of rabbit monoclonal antibodies via grafting combined Kabat/IMGT/Paratome complementarity-determining regions: Rationale and examples. mAbs. 2017;9 (3): 419-29.

What is claimed is:

1. A monoclonal antibody or an antigen binding fragment thereof, wherein the antibody or antigen binding fragment thereof comprises HCDR1, HCDR2, and HCDR3 amino acid sequences provided in a heavy chain variable domain (VH) amino acid sequence of SEQ ID NO: 157 and LCDR1, LCDR2, and LCDR3 amino acid sequences provided in a light chain variable domain (VL) amino acid sequence of SEQ ID NO: 158.

2. The monoclonal antibody or antigen binding fragment thereof of claim 1, wherein the HCDR1, HCDR2, and HCDR3 comprise the amino acid sequences of SEQ ID NOs: 52, 53, and 54, respectively.

3. The monoclonal antibody or antigen binding fragment thereof of claim 1, wherein the LCDR1, LCDR2, and LCDR3 comprise the amino acid sequences of SEQ ID NOs: 7, 8, and 9, respectively.

4. The monoclonal antibody or antigen binding fragment thereof of claim 1, wherein the antibody or an antigen binding fragment thereof comprises a VH comprising an amino acid sequence at least 95% identical to the amino acid sequence of SEQ ID NO: 157.

5. The monoclonal antibody or antigen binding fragment thereof of claim 1, wherein the antibody or an antigen binding fragment thereof comprises a VL comprising an amino acid sequence at least 95% identical to the amino acid sequence of SEQ ID NO: 158.

6. The monoclonal antibody or antigen binding fragment thereof of claim 4, wherein the VH comprises the amino acid sequence of SEQ ID NO: 157.

7. The monoclonal antibody or antigen binding fragment thereof of claim 5, wherein the VL comprises the amino acid sequence of SEQ ID NO: 158.

8. The monoclonal antibody or antigen binding fragment thereof of claim 1, wherein the antibody or an antigen binding fragment thereof comprises a VH and a VL, wherein the VH comprises an amino acid sequence at least 95% identical to the amino acid sequence of SEQ ID NO: 157 and the VL comprises an amino acid sequence at least 95% identical to the amino acid sequence of SEQ ID NO: 158.

9. The monoclonal antibody or antigen binding fragment thereof of claim 8, wherein the VH comprises the amino acid sequence of SEQ ID NO: 157 and the VL comprises the amino acid sequence of SEQ ID NO: 158.

10. The monoclonal antibody or antigen binding fragment thereof of claim 1, wherein the antibody or antigen binding fragment thereof is a humanized antibody.

11. The monoclonal antibody or antigen binding fragment thereof of claim 1, wherein the antibody fragment is a monovalent scFv (single chain fragment variable) antibody, divalent scFv, Fab fragment, F(ab')$_2$ fragment, F(ab')$_3$ fragment, Fv fragment, or single chain antibody.

12. The monoclonal antibody or antigen binding fragment thereof of claim 1, wherein the antibody is a chimeric antibody or bispecific antibody.

13. The monoclonal antibody or antigen binding fragment thereof of claim 1, wherein the antibody is an IgG antibody or antigen binding fragment thereof or a recombinant IgG antibody or antigen binding fragment thereof.

14. The monoclonal antibody or antigen binding fragment thereof of claim 1, wherein the antibody is conjugated or fused to an imaging agent or a cytotoxic agent.

* * * * *